US008735124B2

(12) United States Patent
Tawfik et al.

(10) Patent No.: US 8,735,124 B2
(45) Date of Patent: May 27, 2014

(54) ISOLATED PON1 POLYPEPTIDES, POLYNUCLEOTIDES ENCODING SAME AND USES THEREOF IN TREATING OR PREVENTING ORGANOPHOSPHATE EXPOSURE ASSOCIATED DAMAGE

(75) Inventors: Dan S. Tawfik, Jerusalem (IL); Rinkoo Devi Gupta, Rehovot (IL); Moshe Goldsmith, Rehovot (IL); Yaacov Ashani, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 43 days.

(21) Appl. No.: 13/420,920

(22) Filed: Mar. 15, 2012

(65) Prior Publication Data

US 2012/0213834 A1 Aug. 23, 2012

Related U.S. Application Data

(63) Continuation-in-part of application No. PCT/IL2010/000754, filed on Sep. 15, 2010.

(60) Provisional application No. 61/272,363, filed on Sep. 17, 2009.

(51) Int. Cl.

| | |
|---|---|
| ***C12N 9/16*** | (2006.01) |
| ***C12N 9/14*** | (2006.01) |
| ***C12P 21/06*** | (2006.01) |
| ***C12P 19/34*** | (2006.01) |
| ***C12N 15/00*** | (2006.01) |
| ***C07H 21/04*** | (2006.01) |
| ***C07K 1/00*** | (2006.01) |
| ***A01N 25/34*** | (2006.01) |
| ***A61K 9/00*** | (2006.01) |
| ***A61K 38/46*** | (2006.01) |

(52) U.S. Cl.

USPC ......... 435/196; 435/195; 435/69.1; 435/91.1; 435/320.1; 536/23.1; 536/23.2; 530/350; 424/402; 424/400; 424/94.6

(58) Field of Classification Search

USPC .................... 435/196, 195, 69.1, 91.1, 320.1; 536/23.1, 23.2; 530/350; 424/402, 400, 424/94.6

See application file for complete search history.

(56) References Cited

U.S. PATENT DOCUMENTS

| | | | | |
|---|---|---|---|---|
| 7,786,071 B2 * | 8/2010 | Tawfik et al. | .............. | 424/94.63 |
| 2006/0205933 A1 * | 9/2006 | Tawfik et al. | ................ | 536/23.2 |
| 2011/0171197 A1 * | 7/2011 | Tawfik et al. | ................ | 424/94.6 |

FOREIGN PATENT DOCUMENTS

| | | |
|---|---|---|
| WO | WO 2004/078991 | 9/2004 |
| WO | WO 2007/105223 | 9/2007 |
| WO | WO 2011/033506 | 3/2011 |
| WO | WO 2013/136335 | 9/2013 |

OTHER PUBLICATIONS

Broun et al., Catalytic plasticity of fatty acid modification enzymes underlying chemical diversity of plant lipids. Science, 1998, vol. 282: 1315-1317.*

Chica et al., Semi-rational approaches to engineering enzyme activity: combining the benefits of directed evolution and rational design. Curr. Opi. Biotechnol., 2005, vol. 16: 378-384.*

Devos et al., Practical limits of function prediction. Proteins: Structure, Function, and Genetics. 2000, vol. 41: 98-107.*

Kisselev L., Polypeptide release factors in prokaryotes and eukaryotes: same function, different structure. Structure, 2002, vol. 10: 8-9.*

Sen et al., Developments in directed evolution for improving enzyme functions. Appl. Biochem. Biotechnol., 2007, vol. 143: 212-223.*

Whisstock et al., Prediction of protein function from protein sequence. Q. Rev. Biophysics., 2003, vol. 36 (3): 307-340.*

Wishart et al., A single mutation converts a novel phosphotyrosine binding domain into a dual-specificity phosphatase. J. Biol. Chem., 1995, vol. 270(45): 26782-26785.*

Witkowski et al., Conversion of b-ketoacyl synthase to a Malonyl Decarboxylase by replacement of the active cysteine with glutamine. Biochemistry, 1999, vol. 38: 11643-11650.*

Communication Relating to the Results of the Partial International Search Dated Mar. 22, 2011 From the International Searching Authority Re. Application No. PCT/IL2010/000754.

International Search Report and the Written Opinion Dated Jun. 7, 2011 From the International Searching Authority Re. Application No. PCT/IL2010/000754.

Aharoni et al. "Directed Evolution of Mammalian Paraoxonases PON1 and PON3 for Bacterial Expression and Catalytic Specialization", Proc. Natl. Acad. Sci. USA, PNAS, XP002438727, 101(2): 482-487, Jan. 13, 2004.

Ashani et al. "Stereo-Specific Synthesis of Analogs of Nerve Agents and Their Utilization for Selection and Characterization of Paraoxonase (PON1) Catalytic Scavengers", Chemico-Biological Interactions, XP027174373, 187(1-3): 362-369, Sep. 6, 2010.

Bajgar "Organophosphates/Nerve Agent Poisoning: Mechanism of Action, Diagnosis, Prophylaxis, and Treatment", Advances in Clinical Chemistry, XP009109278, 38: 151-216, Jan. 1, 2004.

Gupta et al. "Directed Evolution of Hydrolases for Prevention of G-Type Nerve Agent Intoxication", Nature Chemical Biology, XP002627100, 7(2): 120-125, Feb. 2011.

(Continued)

*Primary Examiner* — Ganapathirama Raghu

(57) ABSTRACT

An isolated polypeptide comprising the amino acid sequence of serum paraoxonase (PON1) having catalytic efficiency of $k_{cat}/K_M \approx 10^6$-$5\cdot10^7$ $M^{-1}min^{-1}$ for a G-type organophosphate.

16 Claims, 27 Drawing Sheets
(17 of 27 Drawing Sheet(s) Filed in Color)

(56) References Cited

OTHER PUBLICATIONS

Harel et al. "Structure and Evolution of the Serum Paraoxonase Family of Detoxifying and Anti-Atherosclerosis Enzymes", Nature Structural & Molecular Biology, XP002627099, 11(5): 412-419, May 2004.
Rochu et al. "Human Paraoxonase: A Promising Approach for Pre-Treatment and Therapy of Organophosphorus Poisoning", Toxicology, XP022012211, 233(1-3): 47-59, Mar. 31, 2007. Table 3.
Alcolombri et al. "Directed Evolution of Sulfotransferases and Paraoxonases by Ancestral Libraries", Journal of Molecular Biology, 411: 837-853, 2011.
Ashani et al. "In Vitro Detoxification of Cyclosarin in Human Blood Pre-Incubated Ex Vivo With Recombinant Serum Paraoxonases", Toxicology Letters, 206: 24-28, 2011.
International Preliminary Report on Patentability Dated Apr. 4, 2012 From the International Preliminary Examining Authority Re. Application No. PCT/IL2010/000754.
International Search Report and the Written Opinion Dated May 22, 2013 From the International Searching Authority Re. Application No. PCT/IL2012/050239.
Fairchild et al. "Computational Characterization of How the VX Nerve Agent Binds Human Serum Paraoxonase 1", Journal of Molecular Modeling, XP019856245, 17(1): 97-100, Apr. 9, 2010. Abstract.
Amitai et al. "Asymmetric Fluorogenic Organophosphatases for the Development of Active Organophosphates Hydrolases With Reversed Stereoselectivity", Toxicology, 233: 187-198, 2007.
Ashani et al. "Prophylaxis Against Organophosphate Poisoning by an Enzyme Hydrolysis Organophosphorus Compounds in Mice", Life Sciences, 49: 367-374, 1991.
Blum et al. "Inhibitory Potency Against Human Acetylcholinesterase and Enzymatic Hydrolysis of Fluorogenic Nerve Agent Mimics by Human Paraoxonase 1 and Squid Diisopropyl Fluorophosphatase", Biochemistry, 47(18): 5216-5224, Apr. 9, 2008.
Broomfield "A Purified Recombinant Organophosphorus Acid Anhydrase Protects Mice Against Soman", Pharmacology & Toxicology, 70: 65-66, 1992.
DiTargiani et al. "In Search of a Catalytic Bioscavenger for the Prophylaxis of Nerve Agent Toxicity", Chemo-Biological Interactions, 187: 349-354, 2010.
Ghanem et al. "Detoxification of Organophosphate Nerve Agents by Bacterial Phosphotriesterase", Toxicology and Applied Pharmacology, 207: S459-S470, 2005.
Hill et al. "Enhanced Degradation of Chemical Warfare Agents Thorugh Molecular Engineering of the Phosphotriesterase Active Site", Journal of the American Society, JACS, 125(30): 8990-8991, Jul. 8, 2003.
Kassa et al. "The Influence of Combinations of Oximes on the Reactivating and Therapeutic Efficacy of Antidotal Treatment of Soman Poisoning in Rats and Mice", Toxicology Mechanisms and Methods, 19(9): 547-551, Nov. 2009.
Lenz et al. "Stoichimetric and Catalytic Scavengers as Protection Against Nerve Agent Toxicity: A Mini Review", Toxicology, 233: 31-39, 2007.
Li et al. "Paraoxonase Protects Against Chlorpyrifos Toxicity in Mice", Toxicology Letters, 76: 219-226, 1995.
Li et al. "Stereoselective Detoxification of Chiral Sarin and Soman Analogues by Phosphotriesterase", Bioorganic & Medicinal Chemistry, 9: 2083-2091, 2001.
Luo et al. "Mechanism for Potent Reactivation Ability of H Oximes Analyzed by Reactivation Kinetic Studies With Cholinesterases From Different Species", Chemico-Biological Interactions, 187: 185-190, 2010.
Masson et al. "[Engineering of Catalytic Bioscavengers of Organophosphorus Compounds]", Bulletin de l'Academie Nationale de Medicine, 191(1): 95-111, Jan. 2007. Abstract.
Mastrobattista et al. "High-Througput Screening of Enzyme Libraries: In Vitro Evolution of a Beta-Galactosidase by Fluorescence-Activated Sorting of Double Emulsions", Chemistry & Biology, 12: 1291-1300, Dec. 2005.
Melzer et al. "Reversed Enantioselectivity of Diisopropyl Fluorophosphatase Against Organophosphorus Nerve Agents by Rational Design", Journal of the American Chemical Society, JACS, 131: 17226-17232, 2009.
Segall et al. "Direct Observation and Elucidation of the Structures of Aged and Nonaged Phosphorylated Cholinesterases by 31P NMR Spectroscopy", Biochemistry, 32(40): 13441-13450, 1993.

* cited by examiner

FIG. 7A
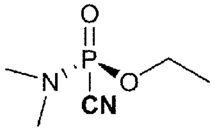
Tabun (GA)
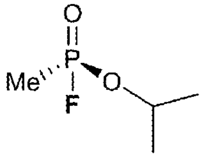
Sarin (GB)
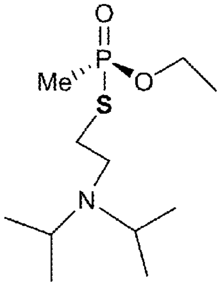
VX
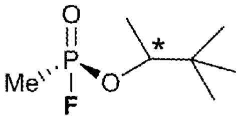
Soman (GD)
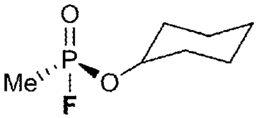
Cyclosarin (GF)
FIG. 7B
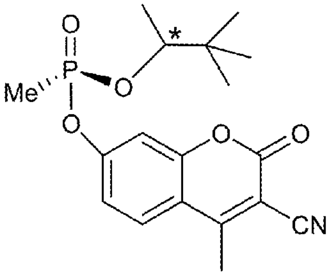
PMP-coumarin
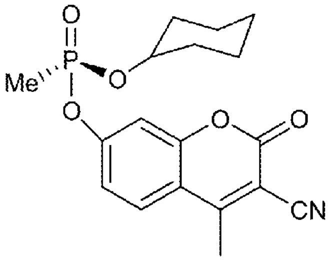
CMP-coumarin

FIG. 8A

| | | | 3.9 | 3.5 | 3.5 | 2 | 1.7 | 1.6 | 1.4 | 1.4 | 1.3 | 1.2 | 1.0 | 1.0 | 0.9 | 0.8 | 0 |
|---|---|---|---|---|---|---|---|---|---|---|---|---|---|---|---|---|---|
| rePON1 | Amino Acid | 2D8 | 9C3 | 4F3 | 5B2 | PIH12 | PD4 | PG3 | PA2 | IG6 | 3D6 | IB3 | 5H8 | 9H3 | JD4 | PG11 | E2B |
| **69** | **L** | G | V | V | V | L | V | V | V | V | V | V | V | V | V | V | V |
| **70** | **K** | K | K | K | K | N | K | K | Q | K | K | Q | K | K | K | K | K |
| **71** | **Y** | Y | Y | F | F | Y | I | I | Y | I | Y | Y | Y | I | Y | Y | Y |
| **82** | **S** | S | S | S | S | S | S | S | S | S | S | S | S | S | S | S | P |
| **115** | **H** | W | W | L | L | L | V | V | L | V | L | L | V | W | L | A | C |
| **134** | **H** | R | R | R | R | R | R | R | N | R | R | N | R | R | N | R | R |
| **196** | **M** | M | M | F | M | M | M | M | M | M | M | M | M | M | L | M | M |
| **222** | **F** | S | S | S | S | S | S | S | S | S | S | S | S | S | S | S | S |
| **240** | **L** | L | L | L | L | L | I | I | L | I | L | L | L | L | L | L | V |
| **292** | **F** | F | F | F | F | F | F | F | F | F | L | F | F | F | F | F | F |
| **332** | **T** | S | S | S | S | S | S | S | S | S | S | S | S | S | S | S | S |

FIG.8B

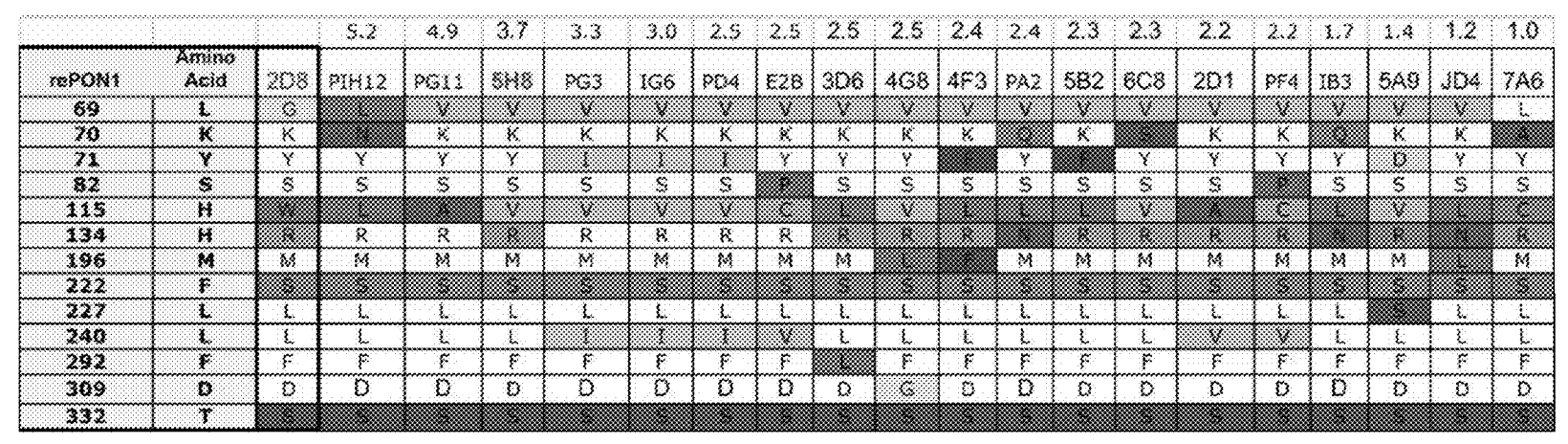

| | | | 5.2 | 4.9 | 3.7 | 3.3 | 3.0 | 2.5 | 2.5 | 2.5 | 2.5 | 2.4 | 2.4 | 2.3 | 2.3 | 2.2 | 2.2 | 1.7 | 1.4 | 1.2 | 1.0 |
|---|---|---|---|---|---|---|---|---|---|---|---|---|---|---|---|---|---|---|---|---|---|
| rePON1 | Amino Acid | 2D8 | PIH12 | PG11 | 5H8 | PG3 | IG6 | PD4 | E2B | 3D6 | 4G8 | 4F3 | PA2 | 5B2 | 6C8 | 2D1 | PF4 | IB3 | 5A9 | JD4 | 7A6 |
| 69 | L | G | L | V | V | V | V | V | V | V | V | V | V | V | V | V | V | V | V | V | L |
| 70 | K | K | N | K | K | K | K | K | K | K | K | K | Q | K | S | K | K | Q | K | K | A |
| 71 | Y | Y | Y | Y | Y | I | I | I | Y | Y | Y | [illegible] | Y | [illegible] | Y | Y | Y | Y | D | Y | Y |
| 82 | S | S | S | S | S | S | S | S | P | S | S | S | S | S | S | S | P | S | S | S | S |
| 115 | H | N | L | A | V | V | V | V | C | L | V | L | L | L | V | A | C | L | V | L | C |
| 134 | H | R | R | R | R | R | R | R | R | R | R | R | [illegible] | R | R | R | R | R | R | [illegible] | R |
| 196 | M | M | M | M | M | M | M | M | M | M | L | [illegible] | M | M | M | M | M | M | M | L | M |
| 222 | F | S | S | S | S | S | S | S | S | S | S | S | S | S | S | S | S | S | S | S | S |
| 227 | L | L | L | L | L | L | L | L | L | L | L | L | L | L | L | L | L | L | S | L | L |
| 240 | L | L | L | L | L | I | I | I | V | L | L | L | L | L | L | V | V | L | L | L | L |
| 292 | F | F | F | F | F | F | F | F | F | L | F | F | F | F | F | F | F | F | F | F | F |
| 309 | D | D | D | D | D | D | D | D | D | D | G | D | D | D | D | D | D | D | D | D | D |
| 332 | T | S | S | S | S | S | S | S | S | S | S | S | S | S | S | S | S | S | S | S | S |

FIG. 9

| Amino Acid | rePON1 | 2D8 | 5H8 | 3D6 | 4F3 | 4G8 | 5B2 | 6C8 | 2D1 | 5A9 | JD4 | 9C3 |
|---|---|---|---|---|---|---|---|---|---|---|---|---|
| 69 | L | G | V | V | V | V | V | V | V | V | V | V |
| 70 | K | K | K | K | K | K | K | S | K | K | K | K |
| 71 | Y | Y | Y | Y | F | Y | F | Y | Y | D | Y | Y |
| 115 | H | W | V | L | L | V | L | V | A | V | L | W |
| 134 | H | R | R | R | R | R | R | R | R | R | N | R |
| 196 | M | M | M | M | F | L | M | M | M | M | L | M |
| 222 | F | S | S | S | S | S | S | S | S | S | S | S |
| 227 | N | L | L | L | L | L | L | L | L | S | L | L |
| 240 | L | L | L | L | L | L | L | L | V | L | L | L |
| 292 | F | F | F | L | F | F | F | F | F | F | F | F |
| 309 | D | D | D | D | D | G | D | D | D | D | D | D |
| 332 | T | S | S | S | S | S | S | S | S | S | S | S |

FIG.10

| | Times repeated: | 2 | | | 3 | | | | | | 9 | | | 4 | |
|---|---|---|---|---|---|---|---|---|---|---|---|---|---|---|---|
| Amino Acid | rePON1 | I-G6 | IVE9 | II-F7 | IVC1 | I-G5 | II-A9 | VID2 | VB3 | II-D11 | II-A1 | II-E8 | II-C11 | VIH5 | IXH5 |
| 18 | D | D | D | D | D | D | D | D | D | D | D | D | G | D | D |
| 64 | F | F | F | F | F | F | F | F | L | F | F | F | F | F | F |
| 69 | L | V | V | V | V | V | V | V | V | V | V | V | V | V | V |
| 70 | K | K | K | K | K | K | K | K | K | K | K | K | K | K | S |
| 71 | Y | Y | Y | Y | Y | Y | Y | Y | Y | Y | Y | Y | Y | Y | Y |
| 78 | D | D | D | D | D | D | D | D | D | D | D | N | D | D | D |
| 85 | I | I | I | I | I | I | I | I | I | I | I | I | I | I | I |
| 106 | T | T | I | T | T | T | T | T | T | T | T | T | T | T | T |
| 115 | H | V | V | V | V | V | V | V | V | L | L | L | L | L | L |
| 128 | Y | Y | Y | Y | Y | Y | Y | Y | Y | Y | Y | Y | Y | Y | Y |
| 134 | H | R | R | R | R | R | R | R | R | R | R | R | R | R | R |
| 196 | M | M | M | M | M | M | M | M | M | M | M | L | M | L | M |
| 211 | N | N | N | N | N | N | N | N | N | N | N | N | N | N | N |
| 212 | D | D | D | D | D | D | D | | | D | D | D | D | D | D |
| 222 | F | M | M | M | L | V | I | V | M | I | M | M | M | M | M |
| 227 | N | N | N | N | N | N | N | N | N | N | N | N | N | N | N |
| 250 | K | K | K | K | K | R | K | K | K | K | K | K | K | K | K |
| 309 | D | D | D | D | D | D | D | D | D | D | D | D | D | D | D |
| 332 | T | S | S | S | S | S | S | S | S | S | S | S | S | S | S |
| 345 | T | T | T | S | T | T | T | T | T | T | T | T | T | T | T |
| Fold improvement with sarin | | 1.3 | 1.5 | 1.6 | 0.8 | 0.8 | 0.6 | 0.8 | 1.1 | 1.4 | 2.4 | 1 | 2.2 | 1.4 | 1.5 |
| Fold improvement with soman | | 1.2 | 1.3 | 1.2 | 1 | 1.1 | 0.7 | 1.4 | 1.1 | 0.9 | 1.1 | 0.4 | 0.9 | 0.7 | 0.6 |
| Fold improvement with cyclosarin | | 3 | 3.3 | 2.3 | 1.5 | 2.1 | 1.4 | 2.2 | 3.8 | 1.6 | 2.5 | 0.5 | 1.8 | 1.4 | 1.2 |

FIG. 10 continued

| | | | | | | 2 | 2 | | | |
|---|---|---|---|---|---|---|---|---|---|---|
| VIG11 | XH2 | VA12 | VA7 | VIB3 | VIIIC1 | IXG1 | I-A4 | VIID11 | IVD11 | IIIB5 |
| D | D | D | D | D | D | D | D | D | D | D |
| F | F | F | F | F | F | F | F | F | F | F |
| V | V | V | V | V | V | V | V | V | V | V |
| K | K | K | K | K | S | K | K | K | K | K |
| Y | Y | Y | F | Y | Y | Y | Y | Y | Y | Y |
| D | D | D | D | D | D | D | D | D | D | D |
| V | I | I | I | I | I | I | I | I | I | |
| T | T | T | T | T | T | T | T | T | T | T |
| L | L | L | L | A | A | A | A | A | A | W |
| Y | Y | Y | Y | N | Y | Y | Y | Y | Y | Y |
| R | R | R | R | R | R | R | R | R | R | R |
| M | F | M | M | L | M | M | M | M | L | M |
| N | N | N | S | N | N | N | N | N | N | N |
| D | D | D | D | D | D | D | D | D | D | N |
| M | M | S | M | M | V | L | M | M | M | M |
| N | S | N | N | N | N | N | N | N | N | N |
| K | K | K | K | K | K | K | K | K | K | K |
| D | D | D | D | D | D | D | D | G | D | D |
| S | S | S | S | S | S | S | S | S | S | S |
| T | T | T | T | T | T | T | T | T | T | T |
| 2.4 | 0.9 | 0.9 | 0.8 | 1 | 2.5 | 0.7 | 2.6 | 2.3 | 3.4 | 1 |
| 1.1 | 0.2 | 0.9 | 0.2 | 0.8 | 1 | 0.9 | 1.3 | 1.3 | 1.3 | 0.1 |
| 2 | 0.5 | 1.9 | 0.4 | 1.8 | 1.5 | 0.9 | 3.4 | 3.2 | 2.9 | 0.4 |

FIG. 11

| Amino Acid | rePON1 | 2D8 | I-A4 | II-A1 | IVD11 | VB3 | VID2 | VIID11 | PIH12 |
|---|---|---|---|---|---|---|---|---|---|
| 64 | F | F | F | F | F | L | F | F | F |
| 69 | L | G | V | V | V | V | V | V | L |
| 70 | K | K | K | K | K | K | K | K | N |
| 115 | H | W | A | L | A | V | V | A | L |
| 134 | H | R | R | R | R | R | R | R | R |
| 196 | M | M | M | M | L | M | M | M | M |
| 222 | F | S | M | M | M | M | V | M | S |
| 309 | D | D | D | D | D | D | D | G | D |
| 332 | T | S | S | S | S | S | S | S | S |

| | | 4 | 3.5 | 3.1 | 3 | 2.9 | 2.9 | 2.6 | 2.5 | 2.3 | 2.3 | 2.2 |
|---|---|---|---|---|---|---|---|---|---|---|---|---|
| Amino Acid | rePON1 | 1-IV-H9 | 1-1-F11 | 1-1-E10 | 1-IV-D4 | 1-2-E9 | 1-1-D10 | 1-2-F2 | 2-1-G7 | 2-1-H10 | 1-3-E3 | 1-IV-A11 |
| 6 | A | A | A | A | A | A | A | A | A | A | A | A |
| 50 | N | N | N | N | N | N | N | N | N | N | N | N |
| 55 | L | I | M | L | L | V | I | V | L | L | L | I |
| 64 | F | F | F | F | F | F | F | F | F | F | F | L |
| 69 | L | V | V | V | V | V | V | V | V | I | V | V |
| 70 | K | K | K | K | K | K | K | K | K | N | K | K |
| 71 | Y | Y | Y | Y | Y | Y | Y | Y | C | Y | Y | Y |
| 74 | I | I | I | I | I | I | I | I | I | I | L | I |
| 75 | M | M | M | M | M | M | M | M | M | M | M | M |
| 115 | H | L | A | A | A | A | A | V | A | A | A | A |
| 134 | H | R | R | R | R | R | R | R | R | R | R | R |
| 136 | D | N | D | D | D | N | D | N | D | D | D | N |
| 197 | H | H | H | H | N | R | H | H | H | H | H | H |
| 222 | F | M | M | M | M | M | M | M | M | M | M | M |
| 291 | I | L | L | L | L | L | F | L | I | I | I | I |
| 292 | F | F | F | F | F | F | F | F | F | F | F | F |
| 309 | D | D | D | D | D | D | D | D | D | D | D | G |
| 332 | T | S | S | S | S | S | S | S | S | S | S | S |

| 2.1 | 2.1 | 2 | 2 | 1.9 | 1.6 | 1.6 |
|---|---|---|---|---|---|---|
| 2-2-D12 | 2-1-G2 | 2-2-C2 | 1-1-G11 | 1-1-B5 | 1-3-B3 | 1-1-G4 |
| A | A | A | A | A | V | A |
| N | N | N | N | N | N | A |
| L | L | L | I | L | I | I |
| F | L | F | L | F | F | F |
| L | V | V | V | V | V | V |
| N | K | K | K | K | K | K |
| Y | Y | Y | Y | Y | Y | Y |
| I | I | I | I | I | I | I |
| M | M | V | M | M | M | M |
| L | A | A | A | A | A | A |
| R | R | R | R | R | R | R |
| D | D | D | D | G | D | N |
| H | H | H | Q | H | R | H |
| M | M | M | M | M | M | M |
| I | I | I | I | I | L | I |
| F | F | F | F | F | F | W |
| D | D | D | D | D | D | D |
| S | S | S | S | S | S | S |

| | | 1.6 | 1.6 | 1.4 | 1.4 | 1.4 | 1.4 | 1.3 | 1.3 | 1.2 | 1.1 | 1.1 | 1.1 |
|---|---|---|---|---|---|---|---|---|---|---|---|---|---|
| **Amino Acid** | **rePON1** | 1-1-F11 | 1-IV-H9 | 1-1-E10 | 1-2-F2 | 1-1-D10 | 1-2-E9 | 1-IV-D4 | 1-1-B5 | 1-1-G4 | 2-2-C2 | 1-IV-A11 | 2-1-F1 |
| 50 | N | N | N | N | N | N | N | N | N | A | N | N | N |
| 55 | L | M | I | L | V | I | V | L | L | I | L | I | L |
| 64 | F | F | F | F | F | F | F | F | F | F | F | L | F |
| 69 | L | V | V | V | V | V | V | V | V | V | V | V | V |
| 75 | M | M | M | M | M | M | M | M | M | M | W | M | M |
| 115 | H | A | L | A | V | A | A | A | A | A | A | A | A |
| 134 | H | R | R | R | R | R | R | R | R | R | R | R | R |
| 136 | D | D | H | D | H | D | H | D | Q | H | D | H | D |
| 197 | H | H | H | H | H | H | R | N | H | H | H | H | H |
| 222 | F | M | M | M | M | M | M | M | M | M | M | M | M |
| 291 | I | L | L | L | L | F | L | L | I | I | I | I | I |
| 292 | F | F | F | F | F | F | F | F | F | W | F | F | F |
| 309 | D | D | D | D | D | D | D | D | D | D | D | G | G |
| 322 | T | S | S | S | S | S | S | S | S | S | S | S | S |

Figure 13:
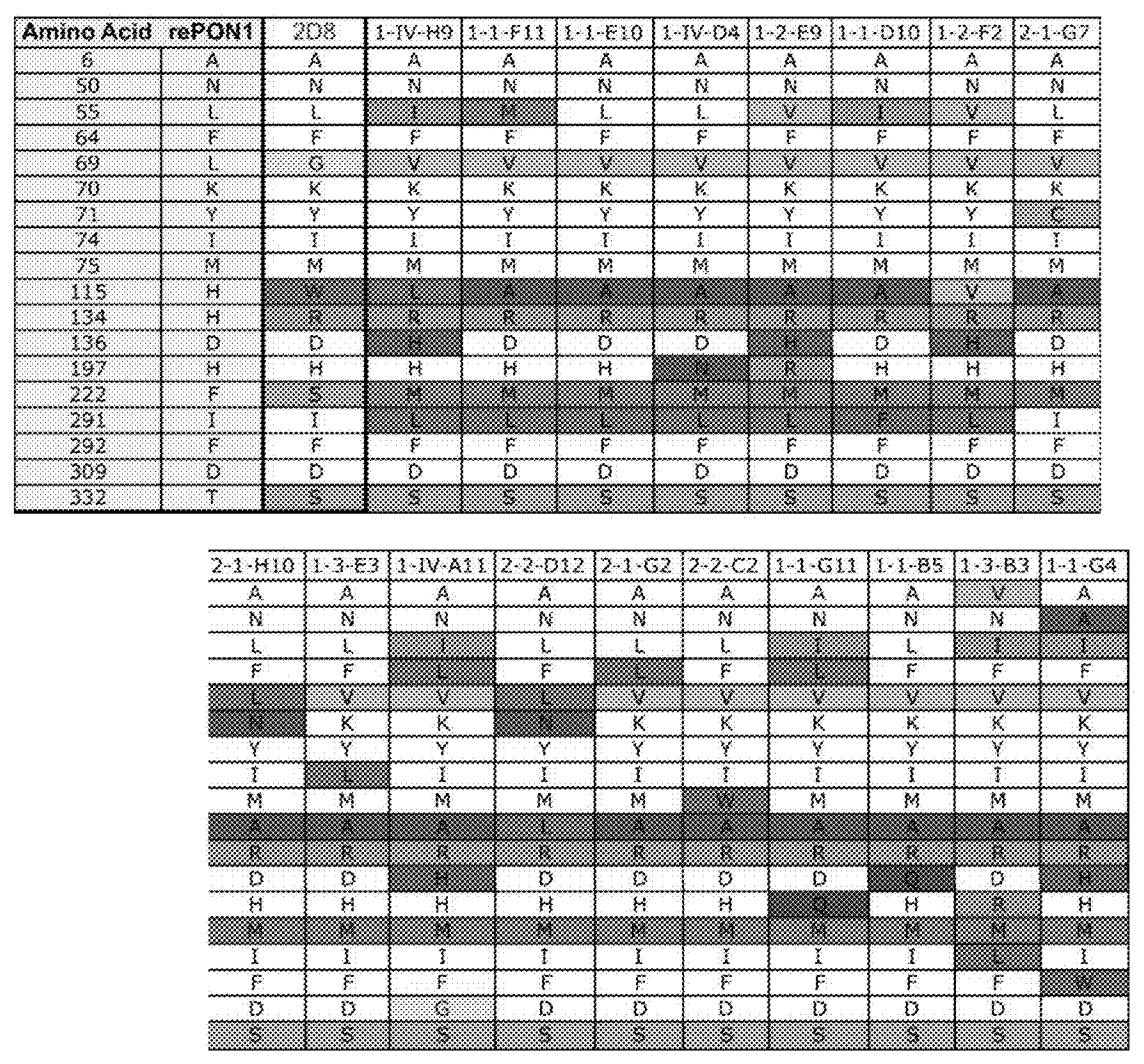

| Amino Acid | rePON1 | 2D8 | 1-IV-H9 | 1-1-F11 | 1-1-E10 | 1-IV-D4 | 1-2-E9 | 1-1-D10 | 1-2-F2 | 2-1-G7 |
|---|---|---|---|---|---|---|---|---|---|---|
| 6 | A | A | A | A | A | A | A | A | A | A |
| 50 | N | N | N | N | N | N | N | N | N | N |
| 55 | L | L | I | M | L | L | V | I | V | L |
| 64 | F | F | F | F | F | F | F | F | F | F |
| 69 | L | G | V | V | V | V | V | V | V | V |
| 70 | K | K | K | K | K | K | K | K | K | K |
| 71 | Y | Y | Y | Y | Y | Y | Y | Y | Y | C |
| 74 | I | I | I | I | I | I | I | I | I | I |
| 75 | M | M | M | M | M | M | M | M | M | M |
| 115 | H | W | L | A | A | A | A | A | V | A |
| 134 | H | R | R | R | R | R | R | R | R | R |
| 136 | D | D | H | D | D | D | H | D | H | D |
| 197 | H | H | H | H | H | R | R | H | H | H |
| 222 | F | S | M | M | M | M | M | M | M | M |
| 291 | I | I | L | L | L | L | L | F | L | I |
| 292 | F | F | F | F | F | F | F | F | F | F |
| 309 | D | D | D | D | D | D | D | D | D | D |
| 332 | T | S | S | S | S | S | S | S | S | S |

| 2-1-H10 | 1-3-E3 | 1-IV-A11 | 2-2-D12 | 2-1-G2 | 2-2-C2 | 1-1-G11 | 1-1-B5 | 1-3-B3 | 1-1-G4 |
|---|---|---|---|---|---|---|---|---|---|
| A | A | A | A | A | A | A | A | V | A |
| N | N | N | N | N | N | N | N | N | S |
| L | L | I | L | L | L | I | L | I | I |
| F | F | L | F | L | F | L | F | F | F |
| L | V | V | L | V | V | V | V | V | V |
| N | K | K | N | K | K | K | K | K | K |
| Y | Y | Y | Y | Y | Y | Y | Y | Y | Y |
| I | L | I | I | I | I | I | I | I | I |
| M | M | M | M | M | W | M | M | M | M |
| A | A | A | L | A | A | A | A | A | A |
| R | R | R | R | R | R | R | R | R | R |
| D | D | H | D | D | D | D | Q | D | R |
| H | H | H | H | H | H | Q | H | R | H |
| M | M | M | M | M | M | M | M | M | M |
| I | I | I | I | I | I | I | I | L | I |
| F | F | F | F | F | F | F | F | F | W |
| D | D | G | D | D | D | D | D | D | D |
| S | S | S | S | S | S | S | S | S | S |

Figure 14:
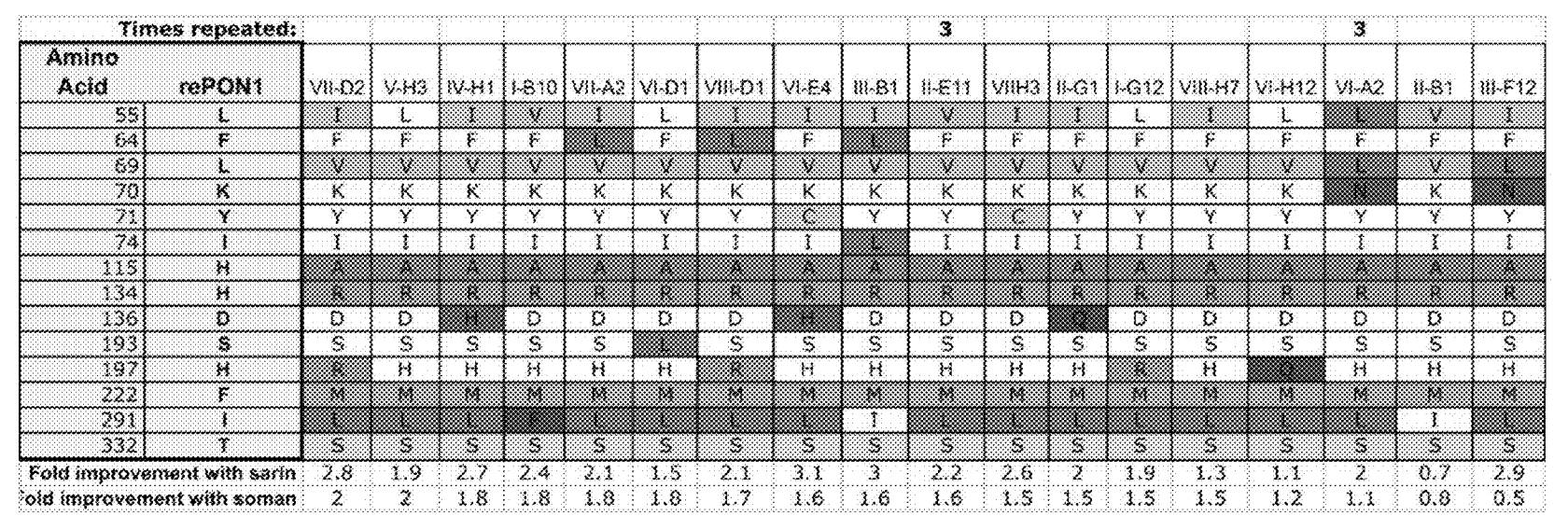

| | Times repeated: | | | | | | | | | 3 | | | | | | 3 | | |
|---|---|---|---|---|---|---|---|---|---|---|---|---|---|---|---|---|---|---|
| Amino Acid | rePON1 | VII-D2 | V-H3 | IV-H1 | I-B10 | VII-A2 | VI-D1 | VIII-D1 | VI-E4 | III-B1 | II-E11 | VIIH3 | II-G1 | I-G12 | VIII-H7 | VI-H12 | VI-A2 | II-B1 | III-F12 |
| 55 | L | I | L | I | V | I | L | I | I | I | V | I | I | L | I | L | L | V | I |
| 64 | F | F | F | F | F | L | F | L | F | L | F | F | F | F | F | F | F | F | F |
| 69 | L | V | V | V | V | V | V | V | V | V | V | V | V | V | V | V | L | V | L |
| 70 | K | K | K | K | K | K | K | K | K | K | K | K | K | K | K | K | N | K | N |
| 71 | Y | Y | Y | Y | Y | Y | Y | Y | C | Y | Y | C | Y | Y | Y | Y | Y | Y | Y |
| 74 | I | I | I | I | I | I | I | I | I | L | I | I | I | I | I | I | I | I | I |
| 115 | H | A | A | A | A | A | A | A | A | A | A | A | A | A | A | A | A | A | A |
| 134 | H | R | R | R | R | R | R | R | R | R | R | R | R | R | R | R | R | R | R |
| 136 | D | D | D | H | D | D | D | D | H | D | D | D | G | D | D | D | D | D | D |
| 193 | S | S | S | S | S | S | L | S | S | S | S | S | S | S | S | S | S | S | S |
| 197 | H | R | H | H | H | H | H | R | H | H | H | H | H | R | H | Q | H | H | H |
| 222 | F | M | M | M | M | M | M | M | M | M | M | M | M | M | M | M | M | M | M |
| 291 | I | L | L | L | F | L | L | L | L | I | L | L | L | L | L | L | L | I | L |
| 332 | T | S | S | S | S | S | S | S | S | S | S | S | S | S | S | S | S | S | S |
| Fold improvement with sarin | | 2.8 | 1.9 | 2.7 | 2.4 | 2.1 | 1.5 | 2.1 | 3.1 | 3 | 2.2 | 2.6 | 2 | 1.9 | 1.3 | 1.1 | 2 | 0.7 | 2.9 |
| Fold improvement with soman | | 2 | 2 | 1.8 | 1.8 | 1.8 | 1.8 | 1.7 | 1.6 | 1.6 | 1.6 | 1.5 | 1.5 | 1.5 | 1.5 | 1.2 | 1.1 | 0.8 | 0.5 |

ISOLATED PON1 POLYPEPTIDES, POLYNUCLEOTIDES ENCODING SAME AND USES THEREOF IN TREATING OR PREVENTING ORGANOPHOSPHATE EXPOSURE ASSOCIATED DAMAGE

RELATED APPLICATIONS

This application is a Continuation-In-Part (CIP) of PCT Patent Application No. PCT/IL2010/000754 having International filing date of Sep. 15, 2010, which claims the benefit of priority of U.S. Provisional Patent Application No. 61/272, 363 filed Sep. 17, 2009. The contents of the above applications are all incorporated herein by reference.

FIELD AND BACKGROUND OF THE INVENTION

The present invention, in some embodiments thereof, relates to isolated PON1 polypeptides, polynucleotides encoding same and uses thereof in treating or preventing organophosphate exposure associated damage.

Inhibitors of acetylcholinesterase (AChE), including organophosphate (OP)-based pesticides and nerve agents, threaten both military and civilian populations. A timely pharmacological treatment with atropine and oxime AChE reactivators can save lives but in many cases does not prevent cholinergic crisis and the resulting onset of secondary toxic manifestations induced by OP intoxication. Side effects associated with drugs such as pyridostigmine used as protective treatment prior to OP exposure have also prompted the search for effective prophylactics and antidotes. Rather than minimizing the damages caused by the OP, the goal of prophylactic drugs is to intercept the OPs before they even reach their target organs. A stoicheiometric bioscavenger based on human butyrylcholinesterase has been recently developed. However, owing to the daunting mass ratio of OP to protein, hundreds of mgs of protein are required to confer protection against exposure to doses beyond a single $LD_{50}$ dose [Ashani, Y. & Pistinner, S. Estimation of the upper limit of human butyrylcholinesterase dose required for protection against organophosphates toxicity: a mathematically based toxicokinetic model. Toxicol Sci 77, 358-67 (2004)]. Catalytic scavengers, namely enzymes displaying multiple turnovers, may allow rapid and efficient protection against high OP doses using low protein amounts [Ditargiani, R. C., Chandrasekaran, L., Belinskaya, T. & Saxena, A. In search of a catalytic bioscavenger for the prophylaxis of nerve agent toxicity. Chem Biol Interact [Epub ahead of print] (2010]. However, with few exceptions, xenobiotics such as OPs are promiscuous substrates for natural enzymes and are degraded with low catalytic efficiencies. Improved OP hydrolyzing enzyme variants have been engineered (e.g. PTE, DFPase, Hill, C. M., Li, W. S., Thoden, J. B., Holden, H. M. & Raushel, F. M. Enhanced degradation of chemical warfare agents through molecular engineering of the phosphotriesterase active site. J Am Chem Soc 125, 8990-1 (2003), Mee-Hie Cho, C., Mulchandani, A. & Chen, W. Functional analysis of organophosphorus hydrolase variants with high degradation activity towards organophosphate pesticides. Protein Eng Des Sel 19, 99-105 (2006), Melzer, M. et al. Reversed enantioselectivity of diisopropyl fluorophosphatase against organophosphorus nerve agents by rational design. J Am Chem Soc 131, 17226-32 (2009)), but prophylactic protection from $\geq 1XLD_{50}$ doses at reasonable protein amounts requires catalytic scavengers whose efficiencies in $k_{cat}/K_M$ terms are $\geq 10^7$ $M^{-1}$ $min^{-1}$.

The G-agents cyclosarin (GF) and soman (GD) comprise a prime target for, scavenger-based prophylaxis due to the low efficacy of pharmacological drugs used to counteract their toxicity [Kassa, J., Karasova, J. Z., Caisberger, F. & Bajgar, J. The influence of combinations of oximes on the reactivating and therapeutic efficacy of antidotal treatment of soman poisoning in rats and mice. Toxicol Mech Methods 19, 547-51 (2009)]. Although applied as racemates, their $S_p$ isomers comprise the tangible threat (FIG. 5). Unfortunately, enzymes tested thus far primarily hydrolyze less toxic $R_p$ isomer [Harvey, S. P. et al. Stereospecificity in the enzymatic hydrolysis of cyclosarin (GF). Enzyme and Microbial Technology 37, 547-555 (2005); Li, W. S., Lum, K. T., Chen-Goodspeed, M., Sogorb, M. A. & Raushel, F. M. Stereoselective detoxification of chiral sarin and soman analogues by phosphotriesterase. Bioorg Med Chem 9, 2083-91 (2001)].

Additional background art includes:

WO2004/078991

Alcolombri, U., Elias, M., and Tawfik, D. S. (2011). Directed evolution of sulfotransferases and paraoxonases by ancestral libraries. Journal of molecular biology 411, 837-853; Ashani, Y., Goldsmith, M., Leader, H., Silman, I., Sussman, J. L., and Tawfik, D. S. (2011). In vitro detoxification of cyclosarin in human blood pre-incubated ex vivo with recombinant serum paraoxonases. Toxicology letters 206, 24-28; and Gupta, R. D., Goldsmith, M., Ashani, Y., Simo, Y., Mullokandov, G., Bar, H., Ben-David, M., Leader, H., Margalit, R., Silman, I., et al. (2011). Directed evolution of hydrolases for prevention of G-type nerve agent intoxication. Nat Chem Biol 7, 120-125.

SUMMARY OF THE INVENTION

According to an aspect of some embodiments of the present invention there is provided an isolated polypeptide comprising an amino acid sequence of serum paraoxonase (PON1) having catalytic efficiency of $10^6$-$5\cdot 10^7$ $M^{-1}min^{-1}$ for a G-type organophosphate.

According to an aspect of some embodiments of the present invention there is provided an isolated polypeptide comprising an amino acid sequence of serum paraoxonase (PON1) having catalytic efficiency of $k_{cat}/K_M \approx 10^6$-$5\cdot 10^7$ $M^{-1}min^{-1}$ for a G-type organophosphate and further having a catalytic efficiency of greater than $10^2$ $M^{-1}min^{-1}$ for a VX type organophosphate.

According to an aspect of some embodiments of the present invention there is provided an isolated polypeptide comprising an amino acid sequence of serum paraoxonase (PON1) having catalytic efficiency of $k_{cat}/K_M \approx 10^6$-$5\cdot 10^7$ $M^{-1}min^{-1}$ for a G-type organophosphate, wherein the amino acid sequence comprises the mutations L69V, H115A, H134R, F222M and I291L and T332S, wherein amino acid coordinates correspond to the G3C9 PON1 variant.

According to an aspect of some embodiments of the present invention there is provided an isolated polypeptide comprising an amino acid sequence of serum paraoxonase (PON1) having catalytic efficiency of $k_{cat}/K_M \approx 10^6$-$5\cdot 10^7$ $M^{-1}min^{-1}$ for a G-type organophosphate, wherein the amino acid sequence comprises the mutations L69V, H115A, H134R, F222M, I291L, L55I, D136Q and T332S, wherein amino acid coordinates correspond to the G3C9 PON1 variant.

According to an aspect of some embodiments of the present invention there is provided an isolated polypeptide comprising an amino acid sequence of serum paraoxonase (PON1) having catalytic efficiency of $k_{cat}/K_M \approx 10^6$-$5\cdot 10^7$ $M^{-1}min^{-1}$ for a G-type organophosphate, wherein the amino acid sequence comprises the mutations L69V, H115A, H134R, F222M, L55I, H197R, I291L and T332S, wherein amino acid acid coordinates correspond to the G3C9 PON1 variant.

According to an aspect of some embodiments of the present invention there is provided an isolated polypeptide comprising an amino acid sequence of serum paraoxonase (PON1) having catalytic efficiency of $k_{cat}/K_M \approx 10^6$-$5 \cdot 10^7$ $M^{-1}min^{-1}$ for a G-type organophosphate, wherein the amino acid sequence is selected from the group consisting of 140-142.

According to some embodiments of the invention, the nerve-agent substrate comprises an Sp isomer.

According to some embodiments of the invention, the isolated polypeptide has catalytic efficiency of $k_{cat}/K_M \approx 10^7$ $M^{-1}min^{-1}$ for Sp nerve-agent substrates.

According to some embodiments of the invention, the Sp isomer comprises each of soman (GD), cyclosarin (GF) and sarin (GB).

According to some embodiments of the invention, the isolated polypeptide has catalytic efficiency of $k_{cat}/K_M \approx 10^6$-$10^7$ $M^{-1}min^{-1}$ for the Rp isomer of tabun (GA).

According to some embodiments of the invention, the isolated polypeptide has a catalytic efficiency of greater than $10^2$ $M^{-1}min^{-1}$ for a VX type organophosphate.

According to some embodiments of the invention, the amino acid sequence of serum paraoxonase (PON1) comprises a mutation selected from the group consisting of: L69G/A/L/V/S/M, K70A/S/Q/N, Y71/F/C/A/L/I, H115W/L/V/C, H134R/N, F222S/M/C, F292S/V/L, T332S/M/C/A, M196V/L/F, V97A, V346A, N41D, Y293S, V97A, V276A, T326S, S111T, S110P, P135A, N41D, N324D, M289I, L240S/V, L14M, L10S, K233E, H285R, H243R, F28Y, F264L, D309N/G, A6E, N227L, F178V, D49N, wherein the amino acid coordinates correspond to the G3C9 PON1 variant.

According to some embodiments of the invention, the isolated polypeptide is expressible in bacteria.

According to some embodiments of the invention, the amino acid sequence is selected from the group consisting of the sequences set forth in SEQ ID NO: 129, 2-54 and 120-128.

According to some embodiments of the invention, the amino acid sequence is selected from the group consisting of the sequences set forth in SEQ ID NO: 129, 2, 4, 7, 9, 12, 24, 47, 53, 120-128.

According to an aspect of some embodiments of the present invention there is provided an isolated polynucleotide comprising a nucleic acid sequence encoding the polypeptide.

According to an aspect of some embodiments of the present invention there is provided a pharmaceutical composition comprising as an active ingredient the isolated polypeptide and a pharmaceutically acceptable carrier.

According to an aspect of some embodiments of the present invention there is provided a nucleic acid construct comprising the isolated polynucleotide and a cis-regulatory element driving expression of the polynucleotide.

According to an aspect of some embodiments of the present invention there is provided a method of treating or preventing organophosphate exposure associated damage in a subject in need thereof, the method comprising providing the subject with a therapeutically effective amount of the isolated polypeptide to thereby treat the organophosphate exposure associated damage in the subject.

According to some embodiments of the invention, the providing is effected prior to the organophosphate exposure.

According to some embodiments of the invention, the providing is effected by inhalation administration.

According to some embodiments of the invention, the providing is effected 10 hours prior to the exposure until 7 days following exposure.

According to some embodiments of the invention, the providing is effected by inhalation and injection.

According to some embodiments of the invention, the method further comprises administering to the subject atropine and optionally oxime.

According to some embodiments of the invention, the providing is effected by topical application.

According to an aspect of some embodiments of the present invention there is provided an article of manufacture for treating or preventing organophosphate exposure associated damage, the article of manufacture comprising the isolated polypeptide immobilized on to a solid support.

According to some embodiments of the invention, the solid support is for topical administration.

According to some embodiments of the invention, the solid support for topical administration is selected from the group consisting of a sponge, a wipe and a fabric.

According to some embodiments of the invention, the solid support is selected from the group consisting of a filter, a fabric and a lining.

According to an aspect of some embodiments of the present invention there is provided a method of detoxifying a surface, the method comprising contacting the surface with the isolated polypeptide, thereby detoxifying the surface.

According to some embodiments of the invention, the method further comprises contacting the surface with a decontaminating foam, a combination of baking condition heat and carbon dioxide, or a combination thereof.

According to some embodiments of the invention, the polypeptide is comprised in a coating, a paint, a non-film forming coating, an elastomer, an adhesive, an sealant, a material applied to a textile, or a wax.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
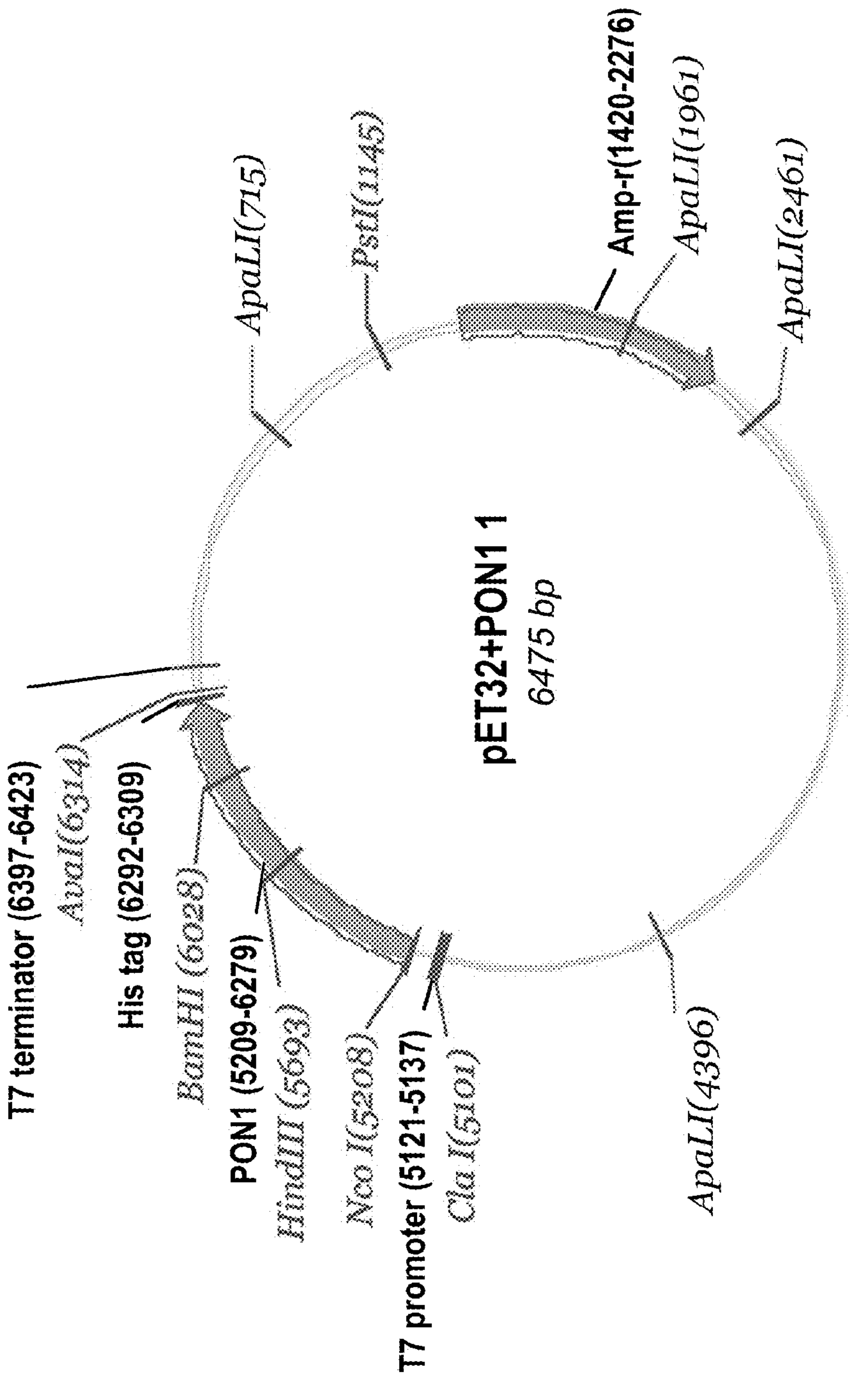

FIG. 1 is a scheme illustrating the pET32PON1 plasmid. This plasmid was used for the expression of PON1 variants with a C-terminal His-tag and no GFP. The plasmid was derived from pET32b(+) from which the thioredoxin fusion protein and peptide tags were truncated using the NotI/XhoI sites. The recombinant PON1 variant G3C9, and library variants, were inserted using the NcoI/NotI sites. The NotI restriction site was inserted upstream to the His tag to enable the cloning of various PON1 variants with no alterations to the tag.

Figures 2A, 2B, 2C:
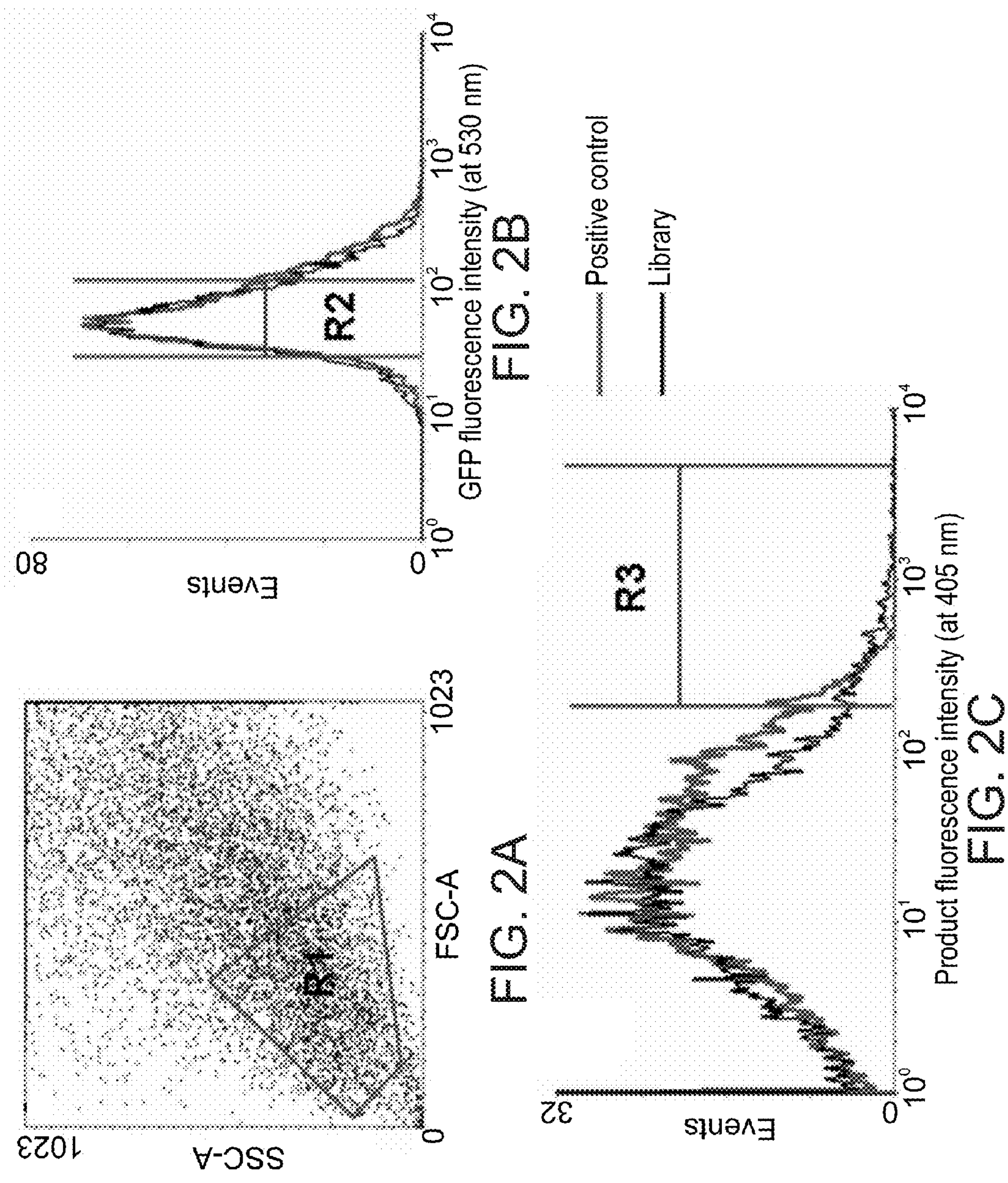

FIGS. 2A-C are graphs of FACS detection and sorting of PON1-carrying *E. coli* cells in w/o/w emulsion droplets. *E. coli* BL21 (DE3) cells possessing GFPuv gene in the genome were used for expression of the PON 1 under the T7 promoter. Cells were emulsified, together with the fluorogenic substrate (DEPCyC). Briefly, filtered cells were compartmentalized in the first emulsion (water-in-oil), and 100 mM solutions of DEPCyC was added to the oil phase (0.8 μl, to a final concentration of 50 μM).

The production of the second emulsion (water-in-oil-in-water) and sorting were performed as described. More than $10^6$ events, at 2000 events/sec, were sorted using FACSAria (Becton-Dickinson). Events corresponding to single *E. coli* cells were gated by GFP emission (at 530 nm, using blue laser for excitation). FIG. 2A-R*epresentative* density plot FSC-H (forward scatter) and SSC-H (side scatter) analysis of the double emulsion. FIG. 2B-H*istogram* of the GFP emission for the R1 population of droplets. Events gated in R2 correspond to droplets that contain GFP expressing cells. FIG. 2C—The R1+R2 gated events were analyzed for the hydrolytic activity. Events gated in R3 represent active variants that were present as 0.5-1% of total population; these were sorted into liquid growth media.

Figure 3:
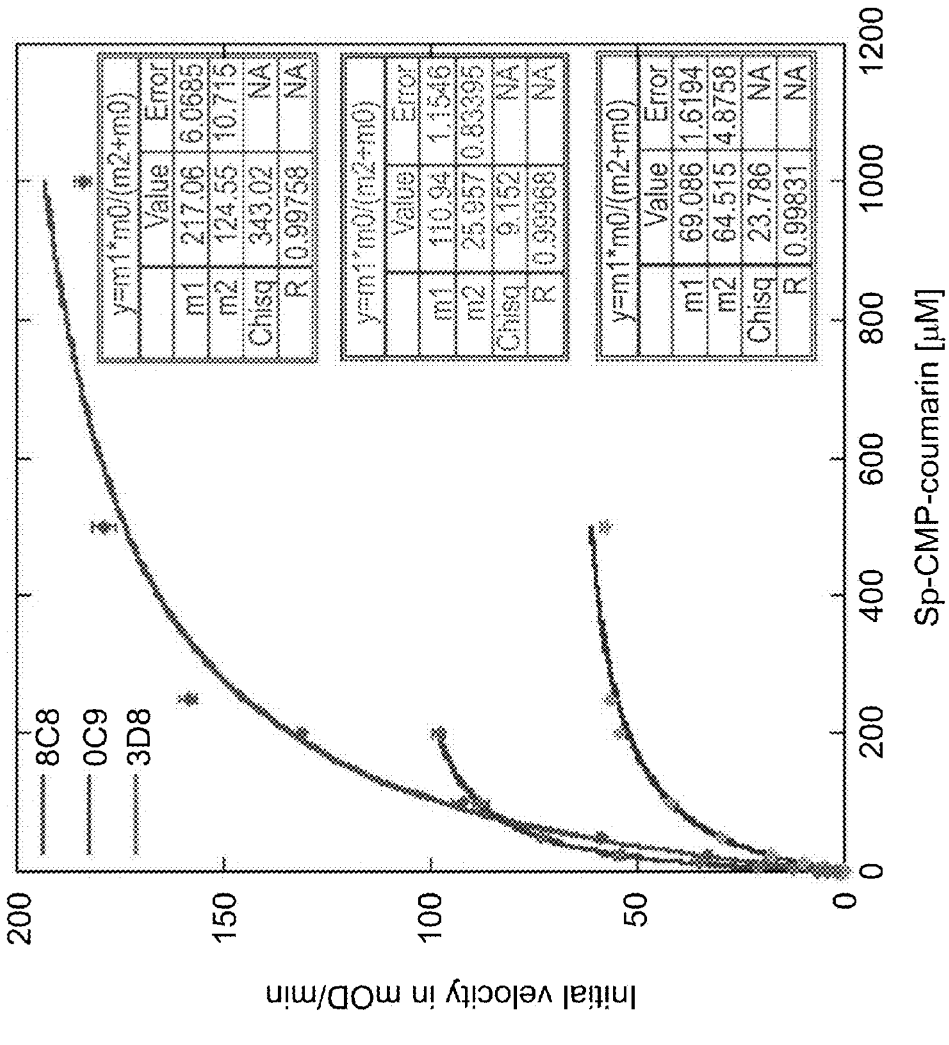
Figure 4:
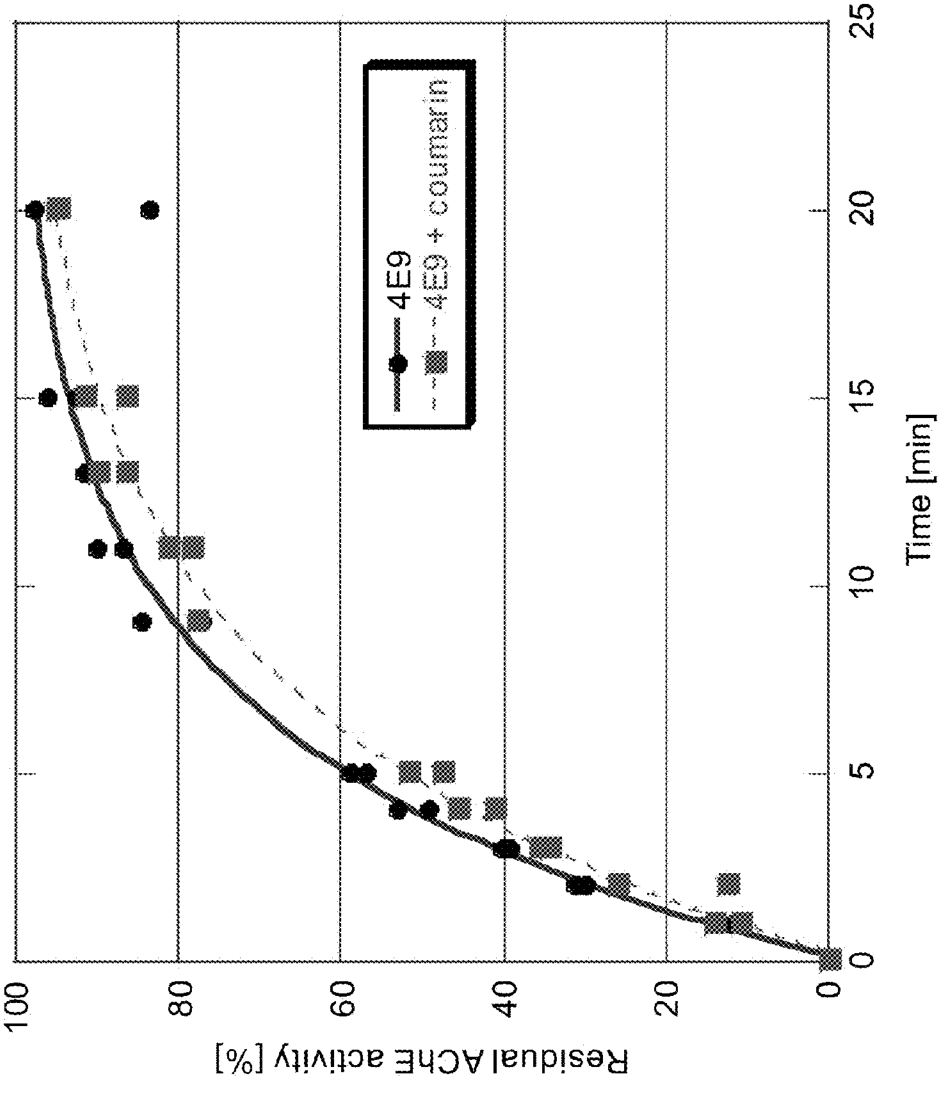

FIG. 3 is a graph illustrating kinetic parameters. Shown is a representative Michaelis-Menten plot for rePON1 variants 8C8, 0C9, and 3D8, evolved towards $S_p$-CMP-MeCyC hydrolysis. Enzyme concentrations were 0.65 μM for 8C8, and 12.5 nM for 0C9 and 3D8. Substrate concentrations were varied from 0.4 μM up to 1000 μM.;

FIG. 4 is a graph showing the effect of excess of free coumarin on the hydrolysis of CMP-F by variant 4E9. The kinetics of CMP-F (40 nM) hydrolysis by 4E9 (16 nM) were determined with and without the addition of a 4-fold excess of free coumarin (64 nM).

Figure 5:
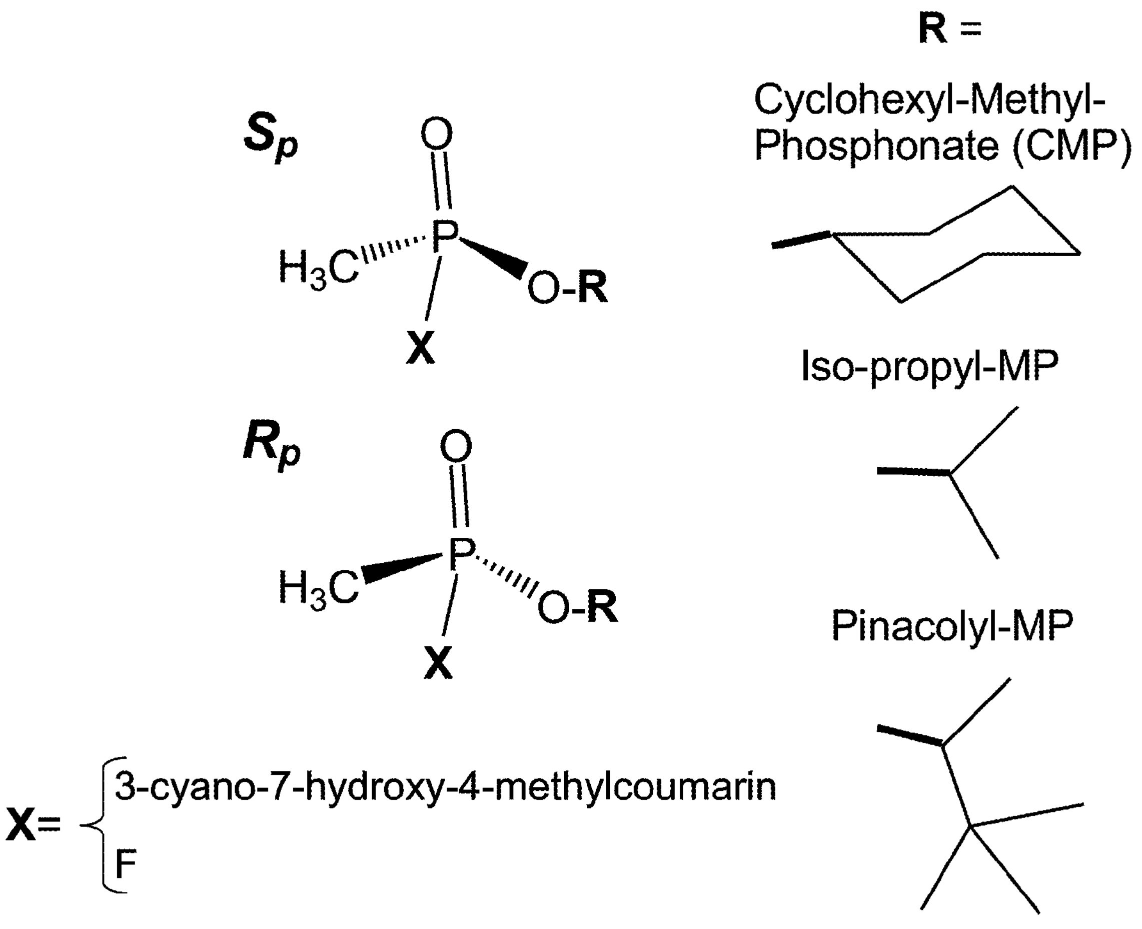

FIG. 5 shows some organophosphates (Ops) used herein. Shown are the two enantiomers of G-agents: cyclosarin (GF, R=cyclohexyl), sarin (GB, R=iso-propyl) and soman (GD, R=pinacolyl). For consistency, the fluorogenic analogues (X=3-cyano-7-hydroxy-4-methylcoumarin) are dubbed CMP-coumarin, IMP-coumarin, and Pin-coumarin, respectively, and the actual agents (X=F) CMP-F, IMP-F, and Pin-F, respectively.

Figure 6C:
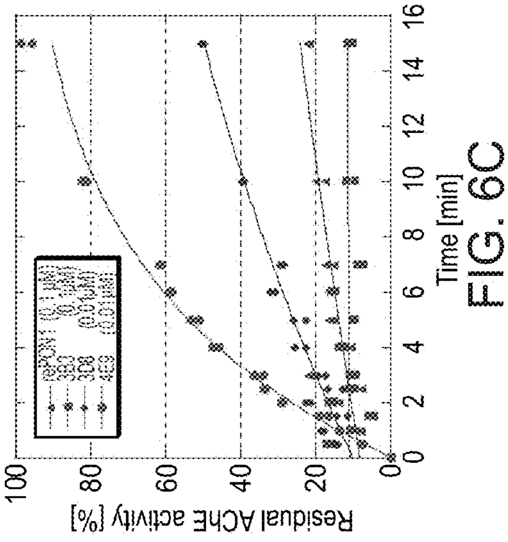
Figure 6A:
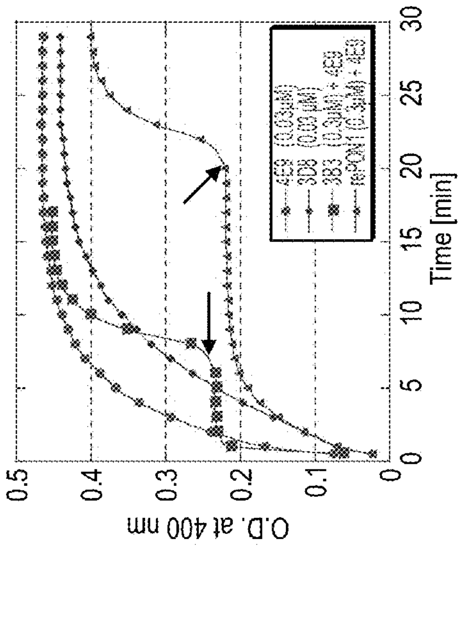
Figure 6B:
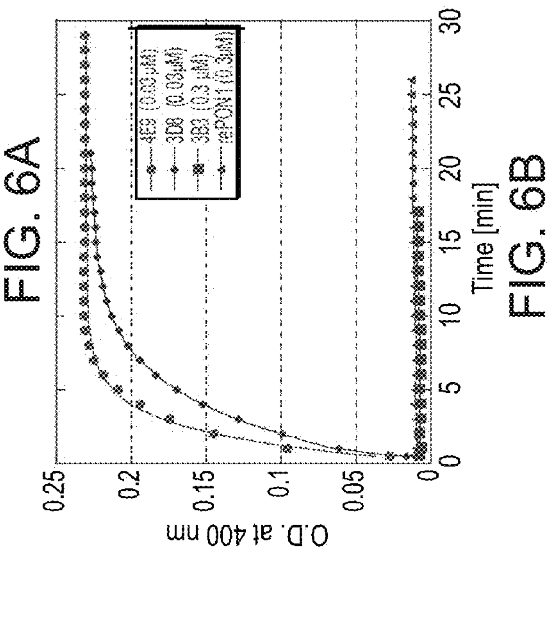

FIGS. 6A-C shows the hydrolysis of CMP-coumarin and CMP-F by rePON1 variants. Enzyme concentrations were varied depending on the variant's activity, and are noted in the figure. FIG. 6A. Hydrolysis of racemic CMP-coumarin (12 μM) in the presence of variants 4E9, 3D8, 3B3 (plus addition of 0.03 μM 4E9 after 6 mins; indicated by the black arrow), and wild-type-like rePON1 (plus addition of 0.03 μM 4E9 after 20 mins). FIG. 6B. Hydrolysis of $S_P$-CMP-coumarin (6 μM) in the presence of variants 4E9, 3D8, 3B3, and rePON1. FIG. 6C. Residual AChE activity was assayed following the incubation of in-situ generated CMP-F (40 nM) and 4E9, 3D8, 3B3, and rePON1; the data were fitted to a first-order rate equation to derive the apparent rate constant for hydrolysis of CMP-F.

FIGS. 7A-B illustrate the structures of the nerve agents and their analogues used in Example 7. A. Structures of GA, GB, GD, GF and VX. Shown are the toxic isomers, i.e. the more potent AChE inhibiting isomers ($S_P$, for GB, GD, GF and VX, and $R_p$ for GA). The chiral carbon of GD is indicated by an asterix. B. Structures of the $S_p$ isomers of the coumarin analogues of GD (PMP-coumarin) and GF (CMP-coumarin).

FIGS. 8A-B are tables illustrating sequences and fold improvement of selected variants from round 1 with Sarin (FIG. 8A) and Soman (FIG. 8B).

FIG. 8A:

* First row—Fold Improvement in activity of each variant relative to control variant 2D8 as measured in cleared cell lysates. Numbers represent an average of 2 measurements with S.D.<10% of value.

** Second row—variant names.

FIG. 8B

* First row—Fold Improvement in activity of each variant relative to control variant 2D8 as measured in cleared cell lysates. Numbers represent an average of 2 measurements with S.D.<10% of value.

** Second row—variant names.

FIG. 9 is a table illustrating sequences of improved variants from round 1 used for shuffling.

* First row—variant names.

** Sequence of rePON1 and variant 2D8 shown for reference.

FIG. 10 is a table illustrating sequences of improved variants from round 2.

* First row—The number of times a clone with the same genotype was independently selected is indicated as "Times repeated" (No number indicated one time).

** Second row—variant names.

*** Last rows—Fold Improvement in activity of each variant relative to round 1 variant PG11 as measured in cleared cell lysates. Numbers represent an average of 3 measurements with S.D.<10% of value.

FIG. 11 is a table illustrating sequences of improved variants from round 2 used for shuffling.

* First row—variant names

** Sequence of rePON1 and variant 2D8 shown for reference

FIGS. 12A-B are tables summarizing sequences and fold improvement of selected variants from round 3 with Sarin (FIG. 12A) and Soman (FIG. 12B).

FIG. 12A:

* First row—Fold Improvement in activity of each variant relative to round 2 variants IA4 and VIID11 as measured in cleared cell lysates. Numbers represent an average of 2 measurements with S.D.<10% of value.

** Second row—variant names (names starting with "1" are from library 1, with "2" are from library 2)

FIG. 12 B:

* First row—Fold Improvement in activity of each variant relative to round 2 variants IA4 and VIID11 as measured in cleared cell lysates. Numbers represent an average of 2 measurements with S.D.<10% of value.

** Second row—variant names (names starting with "1" are from library 1, with "2" are from library 2).

FIG. 13 is a table illustrating the Sequences of improved variants from round 3 used for shuffling.

* First row—variant names

** Sequence of rePON1 and variant 2D8 shown for reference.

FIG. 14 is a table illustrating the sequences and fold improvement of selected variants from round 4.

* First row—The number of times a clone with the same genotype was independently selected is indicated as "Times repeated" (No number indicated one time).

** Second row—variant names.

*** Last rows—Fold Improvement in activity of each variant relative to round 3 variant 1-I-F11, as measured in cleared cell lysates. Numbers represent an average of 3 measurements with S.D.<10% of value.

Figure 15:
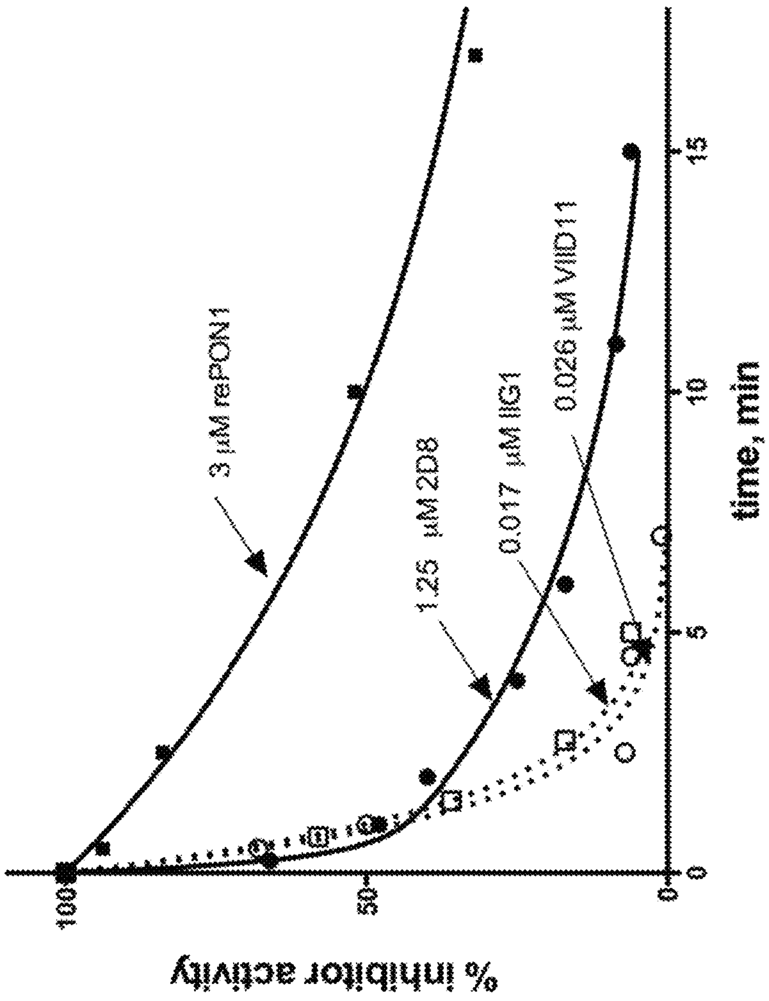

FIG. 15 is a graph illustrating the hydrolysis of GD by evolved variants. Residual AChE activity was assayed and plotted as % of inhibitor activity after the incubation of in situ generated GD (50-100 nM) with 2D8, VIID11, IIG1 and rePON1 at the concentrations noted in the figure (data were fitted to a $2^{nd}$-order rate equation to derive the apparent rate constants for hydrolysis of the two toxic isomers of GD).

Figure 16A:
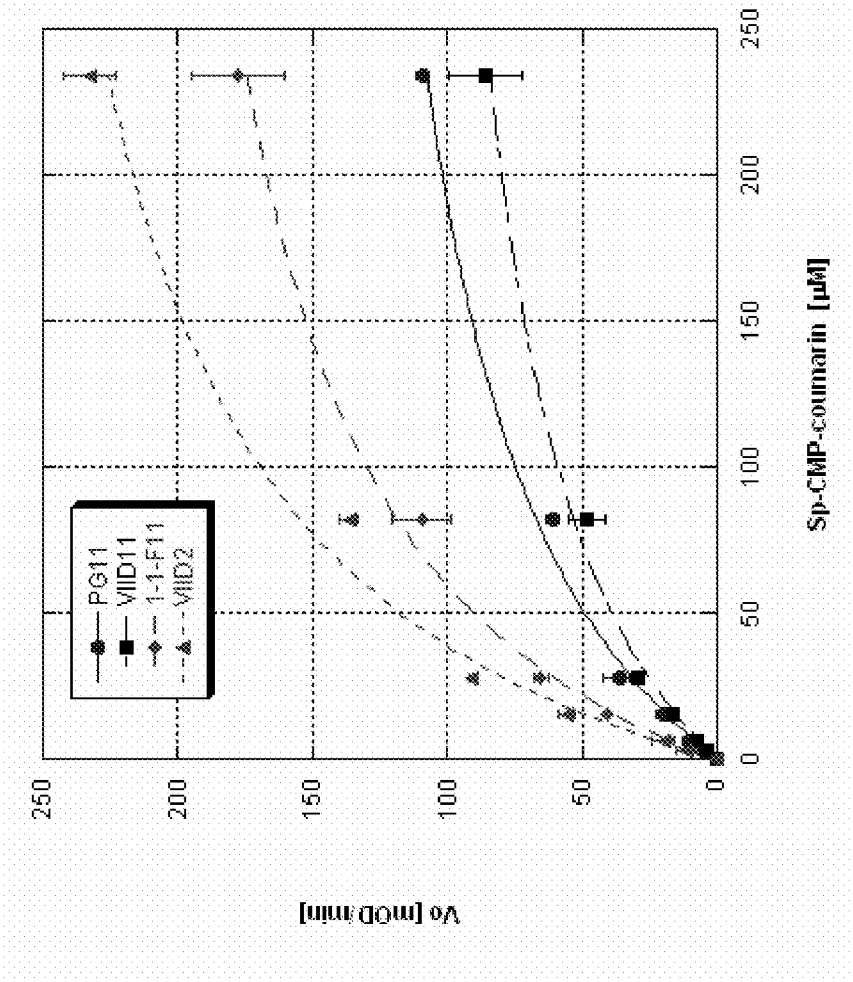
Figure 16B:
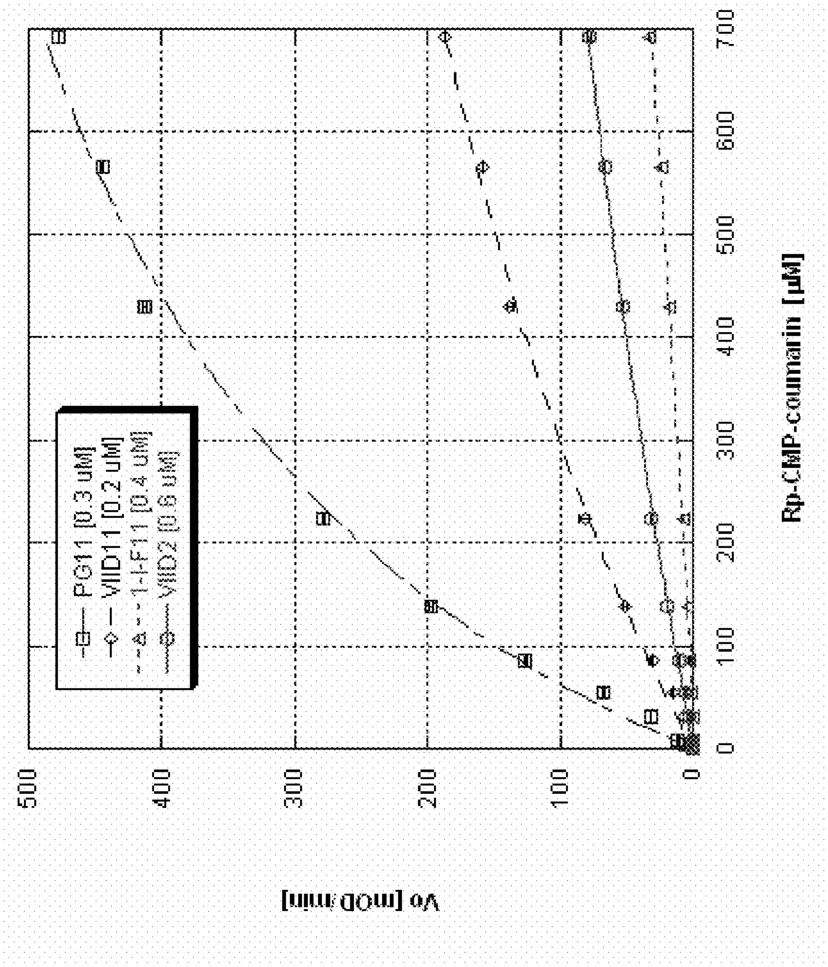

FIGS. 16A-B are graphs illustrating the hydrolysis of $S_p$-CMP-coumarin (FIG. 15A) and $R_p$-CMP-coumarin (FIG. 15B).

FIG. 16A is a Michaelis-Menten plot for rePON1 variants PG11, VIID11, 1-I-F11 and VIID2, with $S_p$-CMP-coumarin. All variants were at 10 nM concentration. Substrate concentrations were varied from 3 μM up to 240 μM. Initial velocities (Vo) were measured at 405 nm.

FIG. 16B is a Michaelis-Menten plot for rePON1 variants PG11, VIID11, 1-I-F11 and VIID2, with $R_p$-CMP-coumarin. Variant concentrations were: PG11 0.3 μM, VIID11 0.2 μM, 1-I-F11 0.4 μM and VIID2 0.6 μM. Substrate concentrations were varied from 4 μM up to 700 μM. Initial velocities (Vo) were measured at 405 nm.

Figure 17A:
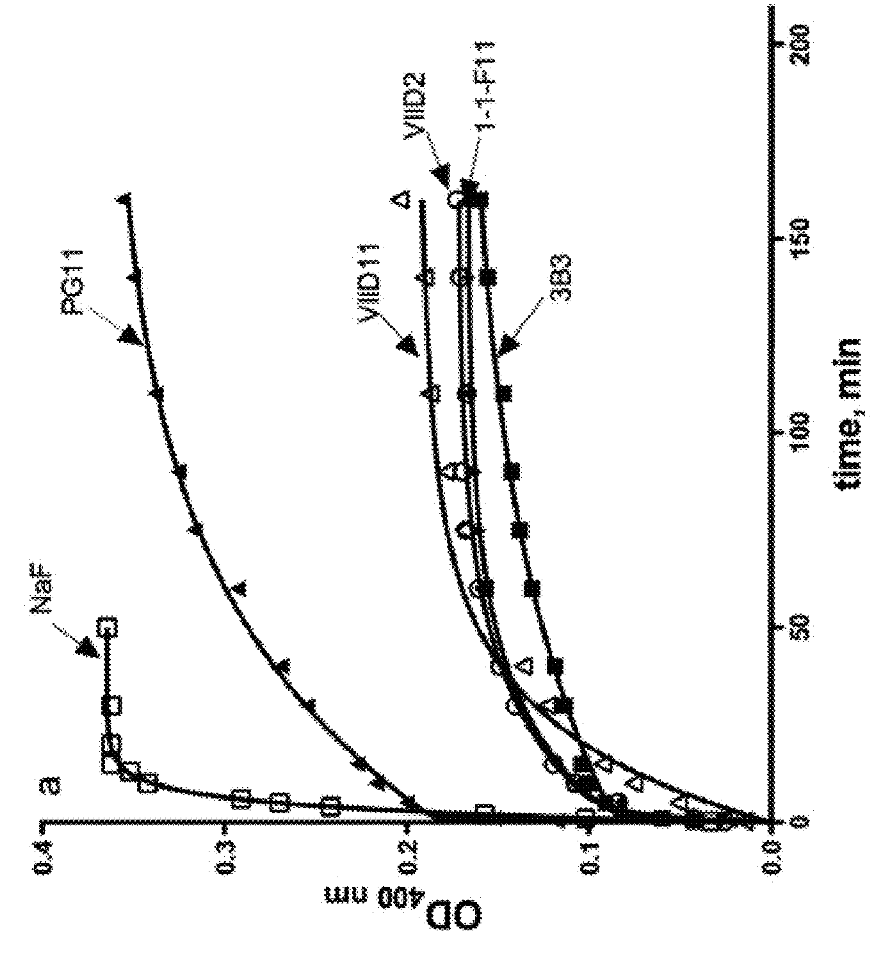
Figure 17B:
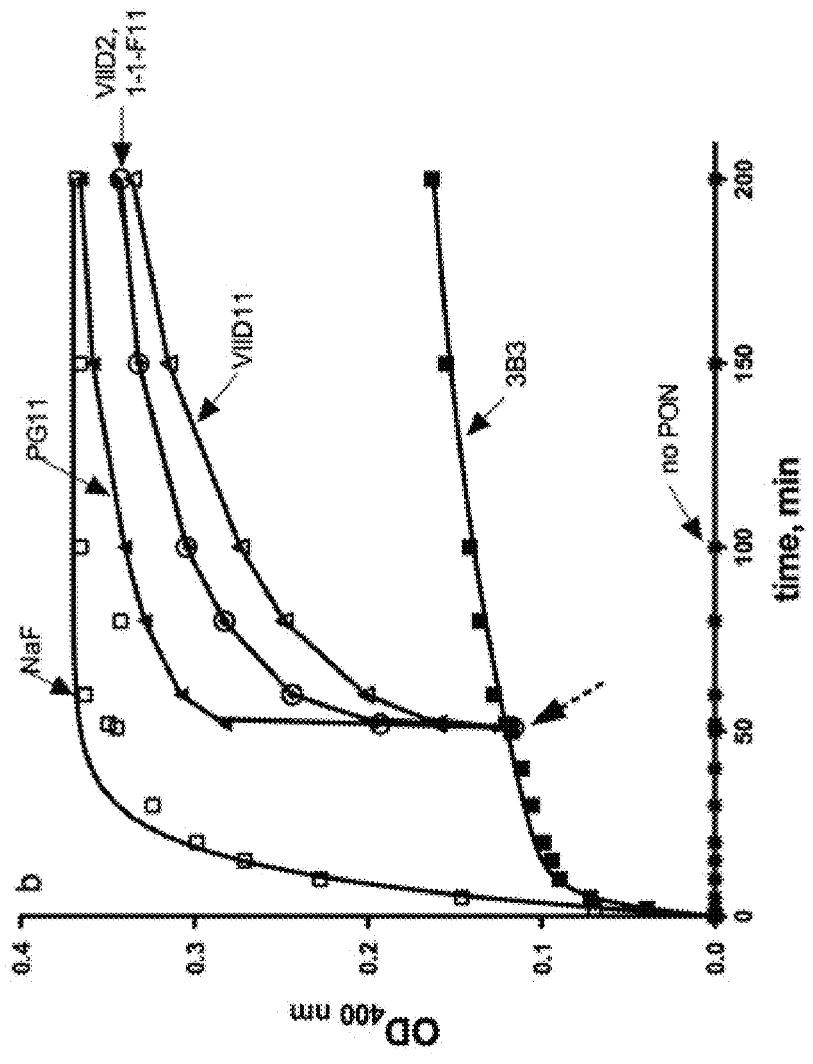

FIGS. 17A-B are graphs illustrating hydrolysis of PMP-coumarin by evolved variants.

A. The hydrolysis of a racemic mixture of PMP-coumarin (10 μM) by various PON1 variants (0.5 μM) was monitored at 400 nm. Complete hydrolysis of all isomers was observed upon addition of NaF (0.25 M). Partial hydrolysis, restricted to $R_p$ isomers ($R_pS_c$, $R_pR_c$), was displayed by the previously described rePON1 variant 3B3 (Ashani, et al., 2010). Round 1 variant PG11 hydrolyzed both sets of $R_p$ and $S_p$ isomers, although at different rates resulting in two distinct phases. In contrast, Round 2-4 variants VIID11, 1-1-F11 and VIID2 exclusively hydrolyzed the $S_p$ isomer pair ($S_pR_c$, $S_pS_c$). B. The hydrolysis of $S_p$ PMP-coumarin isomers ($S_pR_c$,$S_pS_c$) by evolved variants was monitored under similar conditions. Prior to the addition of these variants (indicated by a dashed arrow), samples were pre-incubated with the $R_p$ specific variant 3B3. Complete hydrolysis was monitored by addition of NaF.

Figure 18A:
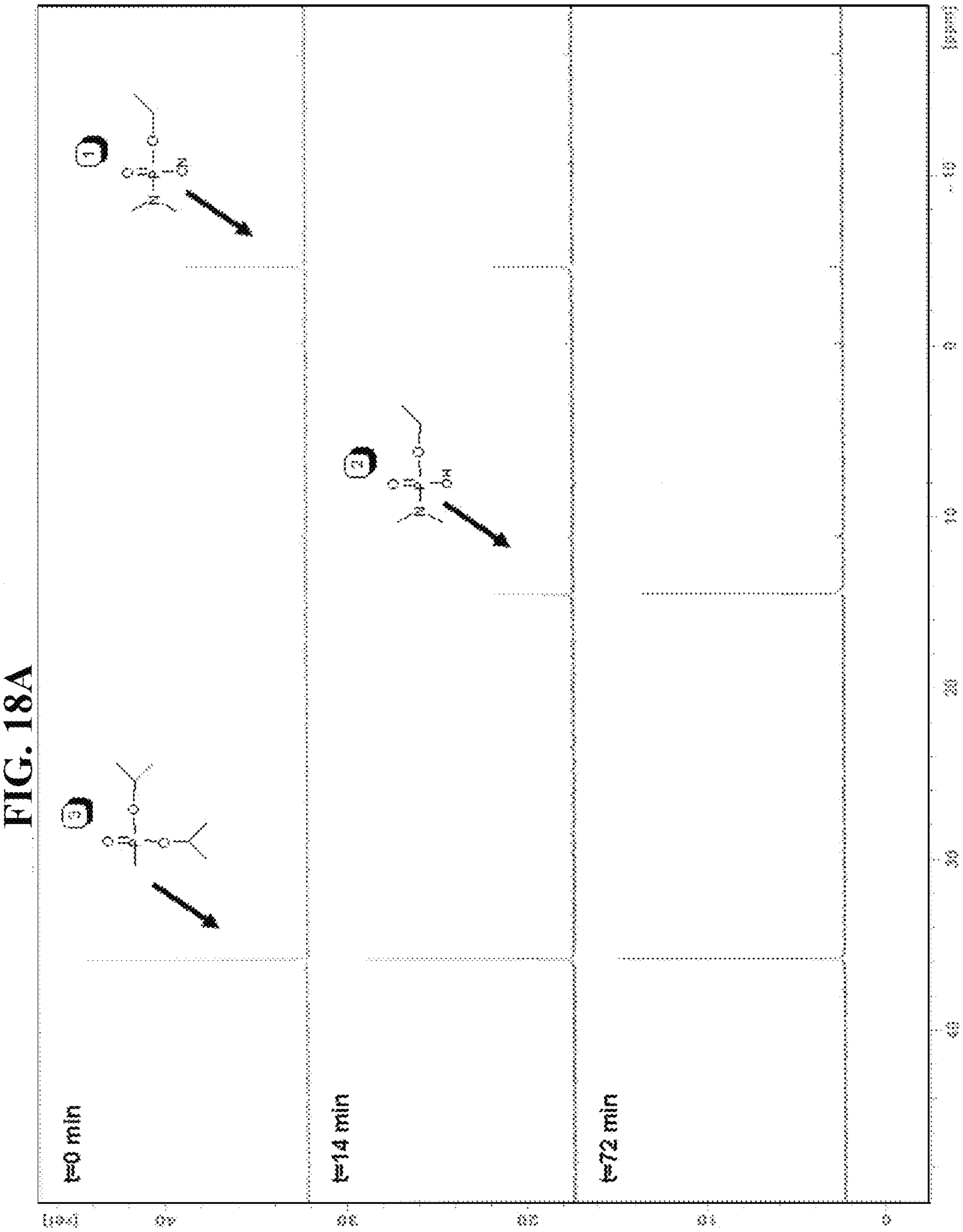

FIG. 18A is a readout of a $^{31}$P NMR analysis of GA hydrolysis by rePON. The hydrolysis of GA by rePON1 was monitored at different time intervals using $^{31}$P NMR. GA (1 mg/ml) was incubated with rePON1 (1.25 μM) in activity buffer for up to 75 min. The $^{31}$P NMR spectra of the mixture, containing also 10% aceton and 2 mg/ml internal standard of O,O,-diisopropyl methylphosphonate, was recorded at the indicated times. The traces of $^{31}$P NMR show the intact GA (1; δ, −4.5 ppm), the hydrolysis product N,N-di-methylamido-O-ethyl phosphate (2; δ, 14.5 ppm), and the internal standard (3; δ, 36.0). A control sample without PON1 did not exhibit any detectable GA hydrolysis for at least 75 min (data not shown).

Figure 18B:
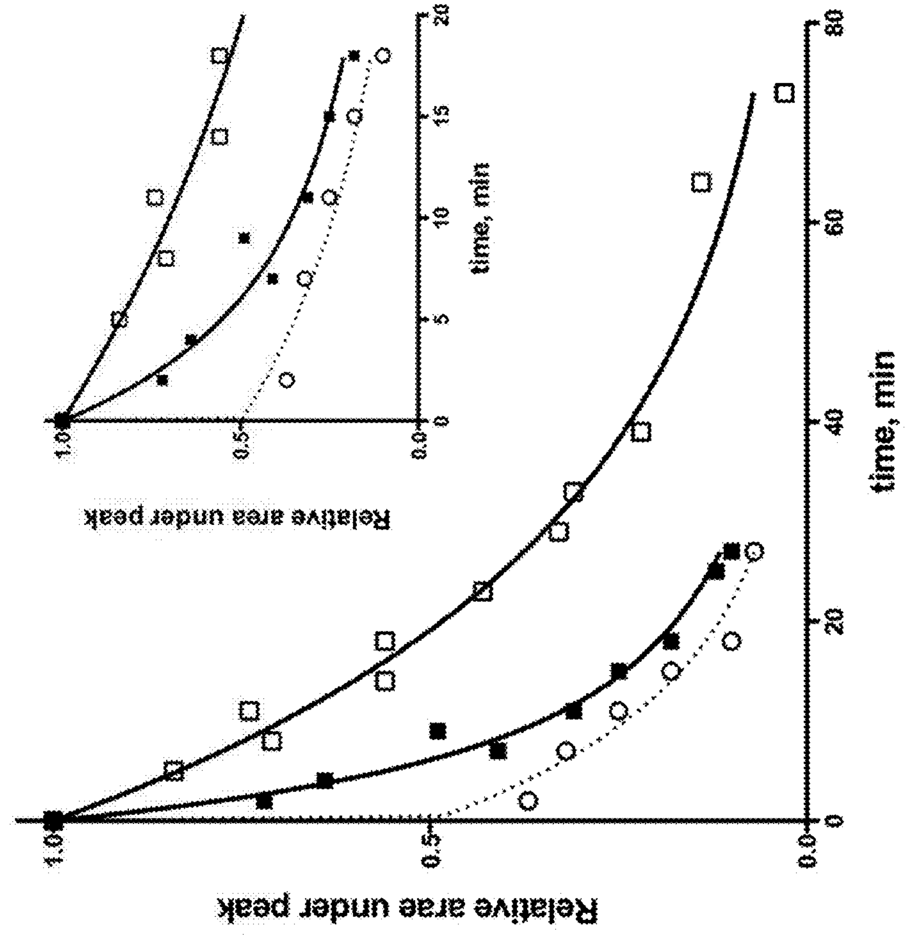

FIG. 18B is a graph illustrating the kinetics of GA hydrolysis by PON1 variants. The hydrolysis of GA was monitored at different time intervals using $^{31}$P NMR. GA (1 mg/ml) was incubated with either rePON1 (1.25 μM); open square, variant 2D8 (2.5 μM); open circle or variant VIID2 (0.36 μM); filled square in activity buffer containing 10% aceton and 20% $D_2O$ (for signal locking) for up to 75 min. The integrated area under the GA peak was normalized against the area under the intact O,O-diisopropyl methylphosphonate (2 mg/ml). Data points were fitted to a bi-exponential decay function in order to visualize the stereo-preference of the tested PON1s. Inset: expansion of the abscise from t=0 to 20 minutes.

Figure 19A:
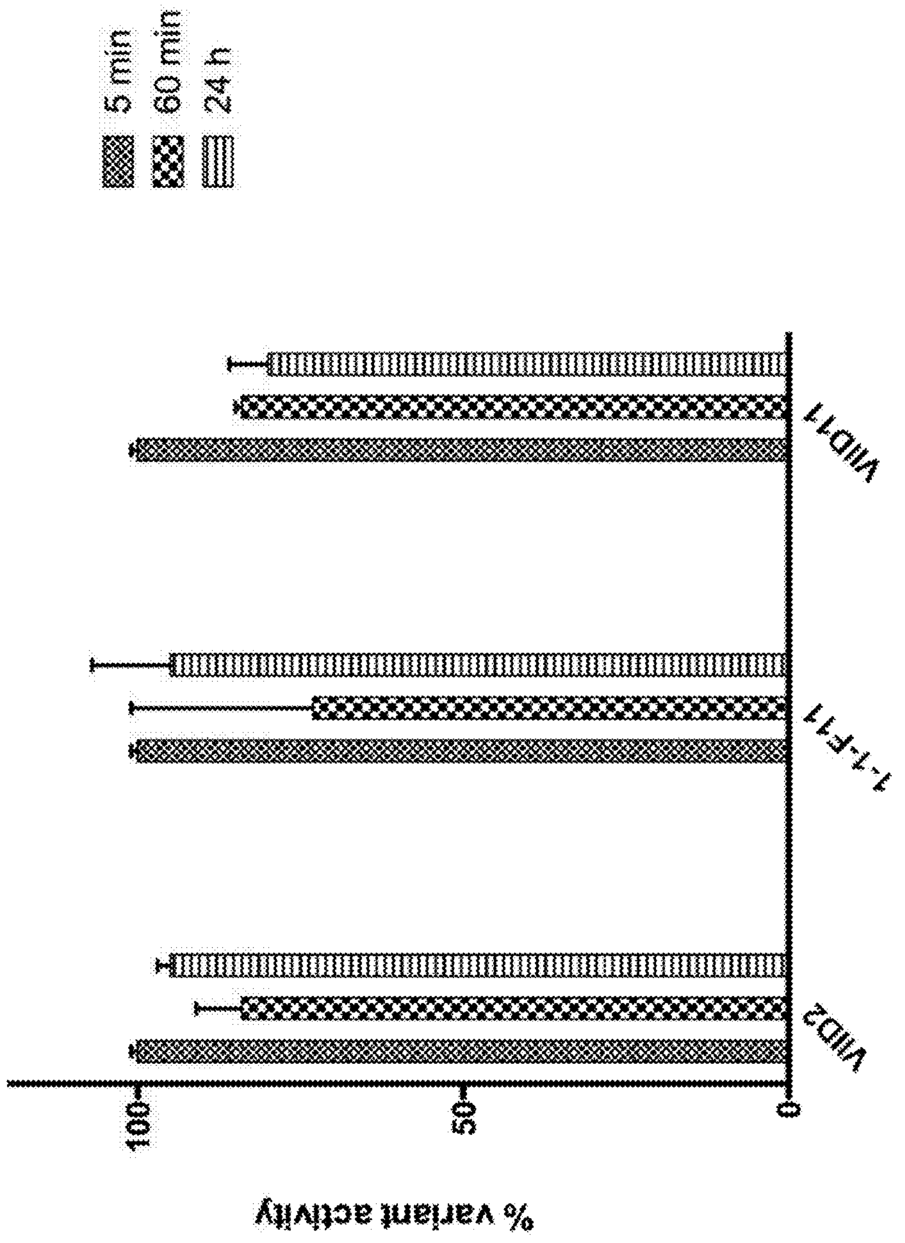
Figure 19B:
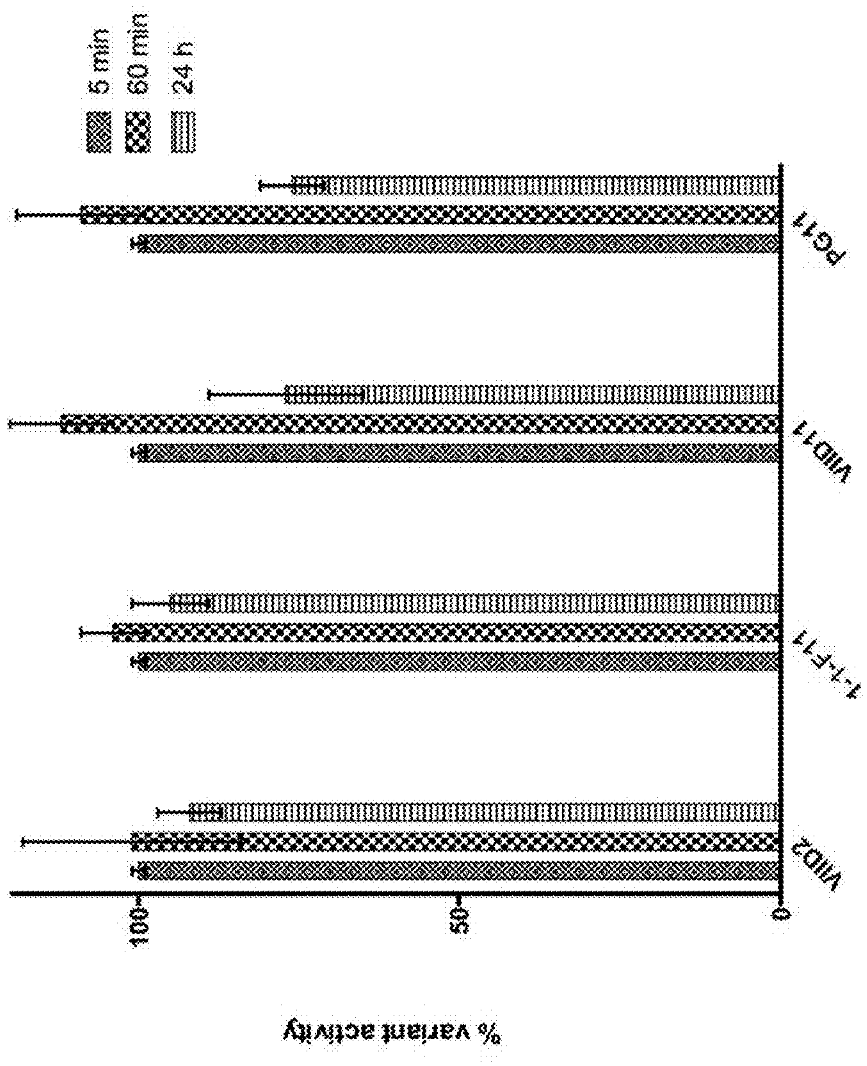

FIGS. 19A-B illustrate activity of variants in blood samples.

A. Protection by evolved variants of blood cholinesterases from inhibition by GF. Evolved variants (0.5-2.1 μM) were incubated in whole blood samples (37° C.) for 24 h. GF was added (0.1 μM) and the samples were assayed for residual acetylcholinesterase activity. Cholinesterase protection activity was compared to the initial protection levels observed after 5 min of incubation (41-45%). B. Hydrolytic activity in whole blood samples. Evolved variants (0.3-1.1 μM) were incubated in whole blood samples (37° C.) for 24 hours. Incubated samples were diluted in buffer and residual enzyme activities were assayed with CMP-coumarin. The percent activity was determined relative to the hydrolytic activity observed after 5 min incubation.

Figure 20:
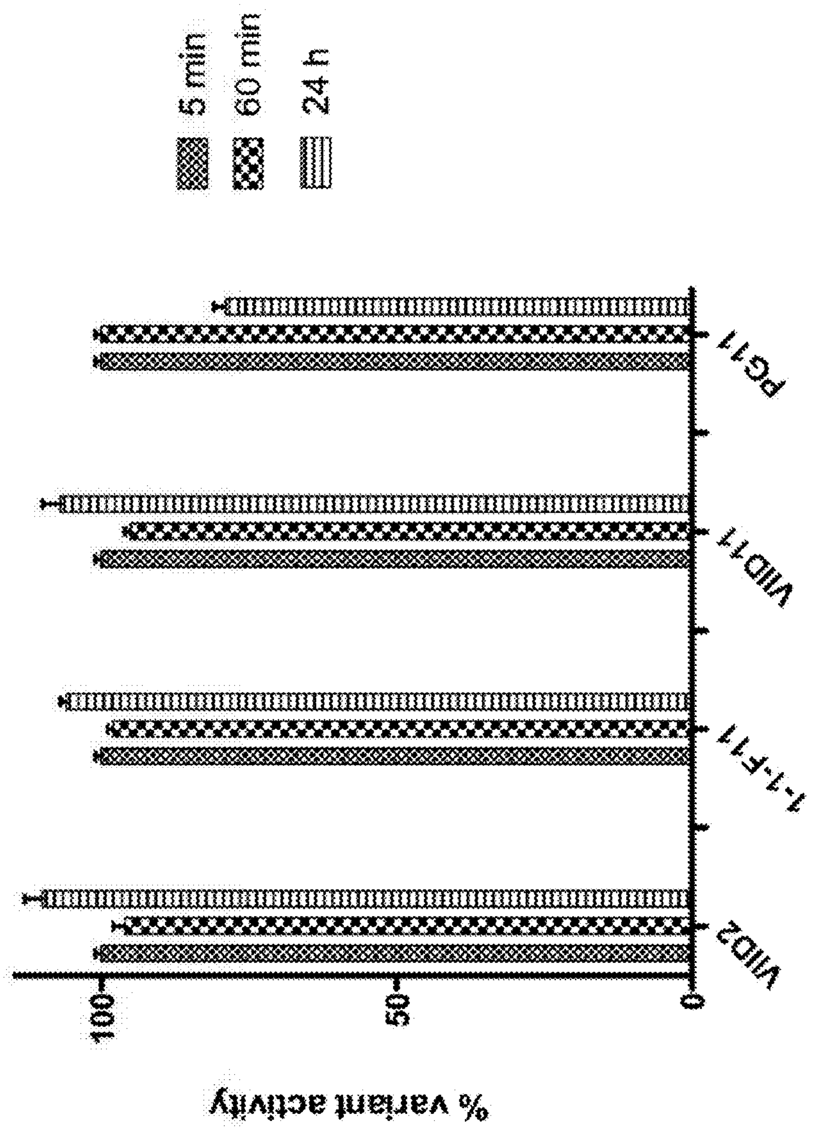

FIG. 20 is a graph illustrating the Stability of evolved variants in buffer at 37° C. Evolved variants: PG11 (0.2 μM), VIID11 (0.13 μM), 1-I-F11 (0.23 μM), VIID2 (0.12 μM) were incubated in buffer (Tris 50 mM pH7.4, $CaCl_2$ 1 mM, NaCl 50 mM, Tergitol 0.1%) at 37° C. for 24 hours. Incubated samples were assayed for CMP-coumarin hydrolysis using 0.3 mM CMP-coumarin at 400 nm in buffer (Tris 50 mM pH 8, $CaCl_2$ 1 mM, NaCl 50 mM, Tergitol 0.1%) at 25° C. Percent hydrolytic activity by each variant was determined relative to the initial hydrolytic activity derived following only 5 min of incubation in buffer.

DESCRIPTION OF SPECIFIC EMBODIMENTS OF THE INVENTION

The present invention, in some embodiments thereof, relates to isolated PON1 polypeptides, polynucleotides encoding same and uses thereof in treating or preventing organophosphate exposure associated damage.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Organophosphates (OPs), including pesticides and nerve agents, comprise a prime target for detoxification. Albeit, no natural enzymes are available that proficiently degrade most of these xenobiotics. Obtaining highly proficient OP hydrolases, and in particular for the more toxic stereoisomer Sp of the G-type nerve agents remains a challenge.

The present inventors generated through laborious experimentation and screening a series of variants of mammalian serum paraoxonase (PON1)—an enzyme that is potentially applicable in vivo, with sufficiently high catalytic efficiency for detoxification ($k_{cat}/K_m \geq 10^7$ $M^{-1}min^{-1}$). Directed evolution of PON1 using structure-based as well as random mutagenesis, and combining low-throughput methodologies (96-well plate screening) with high-throughput screens using compartmentalization in emulsions, enabled taking wild-type-like PON1 that has no detectable activity with Sp G-type OPs, and generating variants with catalytic efficiency of >$10^7$ $M^{-1}min^{-1}$. While the directed evolution used model OPs with a fluorogenic leaving group, a final screen was done using an acetylcholinesterase inhibition assay and in-situ generated nerve agents to identify highly proficient variants that can hydrolyse the actual nerve agents.

The present detoxification model was also validated by demonstrating prophylactic protection in an animal model.

The differences in survival and intoxication symptoms between mice pretreated with the evolved variant 4E9 and mice pretreated with the conventional atropine-oxime treatment probably relate to the very different effects of these treatments—atropine plus 2-PAM aims to minimize the damages of the OP, whereas rePON-4E9 neutralizes the agent before it even reaches its target. In conclusion, there is a direct correlation between the catalytic efficiency of evolved PON1 variants at OP hydrolysis in-vitro and the ability of these variants to act as effective prophylactics in-vivo.

The newly isolated rePON1 variants, and the methodologies described here, also provide the basis for further engineering of PON1 towards other G-type nerve agents, e.g. sarin, and soman. The evolved variants hydrolyze these G type nerve agents, and soman (GD) in particular, at relatively high rates (4E9's apparent $k_{cat}/K_M$ value for sarin (IMP-F) is ≤$3\times10^5$ $M^{-1}$ $min^{-1}$, and for soman (Pin-F), $7.4\times10^6$ $M^{-1}$ $min^{-1}$, and $0.58\times10^6$ $M^{-1}$ $min^{-1}$, for the two toxic isomers respectively). 1-I-F11 exhibits $k_{cat}/K_M$=4*$10^6$ ($M^{-1}$ $min^{-1}$) with the toxic isomer of Sarin (GB) and a catalytic rate of $k_{cat}/K_M$=4.4*$10^7$ ($M^{-1}min^{-1}$) for all toxic isomers of Soman (GD). A catalytic efficiency of $k_{cat}/K_M$=4.6*$10^7$ ($M^{-1}$ $min^{-1}$) for the more toxic isomer of cyclosparin (GF) is exhibited with the 1-I-F11 enzyme.

Using exemplary variants, the present inventors showed that they were able to protect human blood cholinesterases ex-vivo from inhibition by GF for at least 24 hours, thus supporting the possibility of utilizing them for in-vivo prophylaxis. Finally, it was found that the novel variants had improved by ≥150-fold relative to wild-type PON1 for hydrolysis of the toxic isomer of VX, thus providing a starting point for the directed evolution of PON1 for neutralization of V-type agents.

Thus, according to an aspect of the invention there is provided an isolated polypeptide comprising an amino acid sequence of serum paraoxonase (PON1) having catalytic efficiency of $k_{cat}/K_M$≈$10^6$-5·$10^7$ $M^{-1}min^{-1}$ for a nerve-agent substrate.

As used herein the term "serum paraoxonase (PON1)" refers to a naturally occurring or man-made sequence. PON1 (EC 3.1.8.1 or EC 3.1.1.2 e.g., PON1_HUMAN, P27169) is a high-density lipoprotein (HDL)-associated serum enzyme whose primary physiological role is to protect low-density lipoproteins (LDLs) from oxidative modifications. PON1 can also hydrolyze organophosphorus (OP) compounds, including commonly used insecticides, and its name derives from one of its most commonly used in vitro substrates—paraoxon. More recently, in addition to its role in lipid metabolism and, hence, in cardiovascular disease and arteriosclerosis, PON1 has also been shown to be involved in the metabolism of lactones and cyclic carbonates. Early studies of enzymatic activity in serum indicated a bimodal or trimodal distribution in Caucasian populations. Two main polymorphisms in the coding region, as well as five in the 5' regulating region, have been characterized. The Q192R polymorphism determines the catalytic efficiency of hydrolysis of some substrates, and certain promoter polymorphisms, in particular C-108T, contribute to the level of expression of PON1. Recently, additional polymorphisms in the coding region, 5' regulatory region, and PON1 introns have been reported.

Any PON1 may be used e.g., human PON1, rabbit PON1. Others are listed below (Table 1a1).

TABLE 1a1

| Organism | Gene | Locus | Description | Human Similarity | NCBI accessions |
|---|---|---|---|---|---|
| dog (*Canis familiaris*) | PON1 | — | paraoxonase 1 | 89.11(n) 87.89(a) | 475234 XM_845126.1 XP_850219.1 |
| chimpanzee (*Pan troglodytes*) | PON1 | — | paraoxonase 1 | 99.44(n) 99.15(a) | 463547 XM_519211.2 XP_519211.1 |
| cow (*Bos taurus*) | PON1 | — | paraoxonase 1 | 85.4(n) 82.49(a) | 523798 NM_001046269.1 NP_001039734.1 |
| rat (*Rattus norvegicus*) | Pon1 | — | paraoxonase 1 | 82.54(n) 80.56(a) | 84024 NM_032077.1 NP_114466.1 |
| mouse (*Mus musculus*) | Pon1 | 6 (0.50 cM) | paraoxonase 1 | 83.1(n)[1] 81.97(a)[1] | 18979 NM_011134.2 NP_035264.1 BC012706[5] L40488 |

In a specific embodiment the enzyme is expressible in *E. Coli* such as the PON1 variant G3C9 having GenBank Accession AY499193 (see e.g., WO2004/078991, which describes this variant and other equivalent variants and is hereby incorporated by reference in its entirety).

As used herein, a "nerve agent" refers to an organophosphate (OP) compound such as having an acetylcholinesterase inhibitory activity. The toxicity of an OP compound depends on the rate of its inhibition of acetylcholinesterase with the concomitant release of the leaving group such as fluoride, alkylthiolate, cyanide or aryoxy group. The nerve agent may be a racemic composition or a purified enantiomer (e.g., Sp or Rp).

According to a specific embodiment, the nerve agent substrate comprises an Sp isomer.

It will be appreciated that a single variant of this aspect of the present invention may be able to efficiently hydrolyse (i.e. having a $k_{cat}/K_M$≈$10^6$-5·$10^7$ $M^{-1}min^{-1}$) more than one Sp isomer of G agents, for example Sp isomers of two different G agents, three different G agents, or even four different G agents and may therefore serve as a broad range G-type prophylactic. Thus for example the present inventors have shown that VII-D11, 1-1-F11 and IIG1 has a catalytic activity for the Sp isomer of each of GD, GB and GF in this range.

Further, the present invention conceives of variants which have high catalytic activities (i.e. having a $k_{cat}/K_M$≈$10^6$-5·$10^7$ $M^{-1}min^{-1}$) towards the Sp isomers of GD, GB and GF, and in addition having a high catalytic activity towards the Rp isomer of GA.

Certain OP compounds are so toxic to humans that they have been adapted for use as chemical warfare agents (CWAs), such as tabun, soman, sarin, cyclosarin, VX, and R-VX. A CWA may be in airborne form and such a formulation is known herein as an "OP-nerve gas." Examples of airborne forms include a gas, a vapor, an aerosol, a dust, or a combination thereof. Examples of an OP compounds that may be formulated as an OP nerve gas include tabun, sarin, soman, cyclosarin, VX, GX or a combination thereof. An example of an organophosphate which is close to, albeit not similar in its properties to those of the nerve gases is that of DFP, diisopropylfluorophosphonate, which is considerably less volatile than certain members of this group.

In addition to the initial inhalation route of exposure common to such agents, CWAs, especially persistent agents such as VX and thickened soman, pose threats through dermal absorption [In "Chemical Warfare Agents: Toxicity at Low Levels," (Satu M. Somani and James A. Romano, Jr., Eds.) p. 414, 2001]. Such persistent CWA agents remain as a solid or liquid while exposed to the open air for more than three hours. Often after release, a persistent agent may convert from an airborne dispersal form to a solid or liquid residue on a surface, thus providing the opportunity to contact the skin of a human.

Examples of an OP pesticide include bromophos-ethyl, chlorpyrifos, chlorfenvinphos, chlorothiophos, chlorpyrifos-methyl, coumaphos, crotoxyphos, crufomate, cyanophos, diazinon, dichlofenthion, dichlorvos, dursban, EPN, ethoprop, ethyl-parathion, etrimifos, famphur, fensulfothion, fenthion, fenthrothion, isofenphos, jodfenphos, leptophos-oxon, malathion, methyl-parathion, mevinphos, paraoxon, parathion, parathion-methyl, pirimiphos-ethyl, pirimiphos-methyl, pyrazophos, quinalphos, ronnel, sulfopros, sulfotepp, trichloronate, or a combination thereof.

Methods of selecting PON1 polypeptides with the desired activity are provided in the Examples section below. Typically, these methods involve directed evolution of PON1 using structure-based as well as random mutagenesis, and combining low-throughput methodologies (96-well plate screening) with high-throughput screens e.g., using compartmentalization in emulsions, As used herein the phrase "in vitro evolution process" (also referred to as "a directed evolution process") refers to the manipulation of genes and selection or screening of a desired activity. A number of methods, which can be utilized to effect in vitro evolution, are known in the art. One approach of executing the in-vitro evolution process is provided in the Examples section.

General outline of directed evolution is provided in Tracewell C A, Arnold F H "Directed enzyme evolution: climbing fitness peaks one amino acid at a time" Curr Opin Chem Biol. 2009 February; 13(1):3-9. Epub 2009 Feb. 25; Gerlt J A, Babbitt P C, Curr Opin Chem Biol. 2009 February; 13(1):10-8. Epub 2009 Feb. 23 and WO2004/078991 (either of which is hereby incorporated by reference in its entirety).

Methods of producing recombinant proteins are well known in the art.

According to a specific embodiment, mutations which may be employed to improve the hydrolytic efficiency of PON1 to nerve agent substrates comprise mutations in at least one of the following residues, F28, N41, E53, D54, L69, K70, Y71, P72, G73, I74, M75, H115, G116, H134, V167, N168, D169, T181, D183, H184, M196, H197, F222, A223, N224, G225, L240, L241, L267, V268, D269, N270, C284, H285, N287, G288, R290, I291, F292, F293, Y294, N309, G330, S331, T332, V346, F347 V436 Y293, V276, T326, S111, S110, P135, N41, N324, M289, L240, L14, L10, L55, K233, H285, H243, F28, F264, D309, A6, N227, F178, R136Q and D49, where the coordinates corresponds to the PON1 variant G3C9 (SEQ ID NO: 1) having GenBank Accession AY499193. Amino acid coordinates should be adapted easily to PON1 variants of the same or other species by amino acid sequence alignments which may be done manually or using specific bioinformatic tools such as FASTA, L-ALIGN and protein Blast.

Some exemplary mutations include but are not limited to L69G/A/L/V/S/M, K70Q/T/R/D/A/S/Q/N, Y71/F/C/A/L/I/M/W, H115W/L/V/C/A, H134H/R/N, F222S/M/C, F292S/V/L, T332S/M/C/A, M196V/L/F/I, V97A, N309G, V346A/L/I/FW, L55M, R136Q, N41D, Y293S, V276A, T326S, S111T, S110P, P135A, N41D, N324D, M289I, L240I/S/V, L14M, L10S, K233E, H285R, H243R, F28Y, F264L, D309N/G, A6E, N227L, F178V, D49N, N50G/A, H197L/S/R/Q/N/T, I291F/W/L, F292L/I/W, Y294F/Q/N, F347G/A/I/L/V/T/S/W, H348G/A/I/L/V/TS/W, P72G/S, G73P/S, I74W/F/P/S/G, M75L/WF/P, F77G/A/I/V/L/T/S/W/M, D78N/Q/S/A/V/Y/G/S/P.

Thus the present teachings provide for an isolated polypeptide comprising an amino acid sequence of serum paraoxonase (PON1) having catalytic efficiency between the range of $k_{cat}/K_M \approx 10^6$-$10^8$ $M^{-1}min^{-1}$, or specifically of $k_{cat}/K_M \approx 10^6$ $M^{-1}min^{-1}$, $k_{cat}/K_M \approx 5\times10^6$ $M^{-1}min^{-1}$, $k_{cat}/K_M \approx 10^7$ $M^{-1}min^{-1}$, $k_{cat}/K_M \approx 5\times10^7$ $M^{-1}min^{-1}$, $k_{cat}/K_M \approx 10^8$ $M^{-1}min^{-1}$ for nerve-agent substrates (e.g., Sp isomers).

The polypeptides of the present invention are preferably expressible in bacteria such as *E. coli* [e.g., BL21, BL21 (DE3), Origami B (DE3), available from Novagen (wwwdotcalbiochemdotcom) and RIL (DE3) available from Stratagene, (wwwdotstratagenedotcom). Essentially, at least 2%, at least 5%, at least 10%, at least 20%, at least 30%, at least 40%, at least 50%, at least 60%, at least 70%, at least 80%, at least 90%, at least 95% or more, say 100%, of bacterially expressed protein remains soluble (i.e., does not precipitate into inclusion bodies).

According to some embodiments of the invention, the amino acid sequence of the polypeptide is selected from the group consisting of the sequences set forth in SEQ ID NO: 129, 2-54, 120-128 and 140-142.

According to a specific embodiment, the isolated polypeptide is selected from the list below (Table 1a2). Other polypeptides are listed in the Examples section which follows.

TABLE 1a2

| Round | Name of clone | SEQ ID NO: |
|---|---|---|
| Round 0 | 8C8 | 47 |
| | OC9 | 53 |
| | 1A4 | 12 |
| | 2D8 | 2 |
| | 4E9 | 4 |
| Round 1 called G1-2D8 | 5H8 | 7 |
| | 2G11 | 24 |
| | 9C3 | 9 |
| Round 2 called G2-2D8 | VI-D2 | 124 |
| | MG2-I-A4 | 120 |
| | IV-D11 | 122 |
| | II-A1 | 121 |
| | V-B3 | 123 |
| | VII-D11 | 125 |
| Round 3 called also -G3-2D8 | 2-II-D12 | 126 |
| | 1-I-D10 | 127 |
| | 1-IV-H9 | 128 |
| Round 4 | 1-I-F11 | 129 |
| | IIG1 | 140 |
| | VH3 | 141 |
| | VIID2 | 142 |

As used herein the term "isolated" refers to isolated from the natural environment e.g., serum.

The term "polypeptide" as used herein encompasses native polypeptides (synthetically synthesized polypeptides or recombinant polypeptides) and peptidomimetics, as well as peptoids and semipeptoids which are peptide analogs, which may have, for example, modifications rendering the polypeptides more stable while in a body or more capable of penetrating into cells. Such modifications include, but are not limited to N terminus modification, C terminus modification, peptide bond modification, including, but not limited to, CH2-NH, CH2-S, CH2-S═O, O═C—NH, CH2-O, CH2-CH2, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), peptide derivatives (—N(R)—CH2-CO—), wherein R is the "normal" side chain, naturally presented on the carbon atom.

Synthetic amino acid substitutions may be employed to improve stability and bioavailability.

Table 1a3 below lists non-conventional or modified amino acids e.g., synthetic, which can be used with the present invention.

TABLE 1a3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane- | Cpro | L-N-methylasparagine | Nmasn |
| carboxylate | | L-N-methylaspartic acid | Nmasp |
| aminoisobutyric acid | Aib | L-N-methylcysteine | Nmcys |
| aminonorbornyl- | Norb | L-N-methylglutamine | Nmgin |
| carboxylate | | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |

TABLE 1a3-continued

| Non-conventional amino acid | Code | Non-conventional amino acid | Code |
|---|---|---|---|
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

The present teachings also provide for nucleic acid sequences encoding such PON1 polypeptides.

Thus, according to an aspect of the present invention there is provided an isolated polynucleotide including a nucleic acid sequence, which encodes the isolated polypeptide of the present invention.

As used herein the phrase "an isolated polynucleotide" refers to a single or a double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to an exemplary embodiment the polynucleotide is selected from the group consisting of 56-108 and 130-139.

Polypeptides of the present invention can be synthesized using recombinant DNA technology or solid phase technology.

Recombinant techniques are preferably used to generate the polypeptides of the present invention. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce a polypeptide of the present invention using recombinant technology, a polynucleotide encoding a polypeptide of the present invention is ligated into a nucleic acid expression construct, which includes the polynucleotide sequence under the transcriptional control of a cis-regulatory (e.g., promoter) sequence suitable for directing constitutive or inducible transcription in the host cells, as further described hereinbelow.

Other than containing the necessary elements for the transcription and translation of the inserted coding sequence, the expression construct of the present invention can also include sequences (i.e., tags) engineered to enhance stability, production, purification, yield or toxicity of the expressed polypeptide. Such a fusion protein can be designed so that the fusion protein can be readily isolated by affinity chromatography; e.g., by immobilization on a column specific for the heterologous protein. Where a cleavage site is engineered between the peptide moiety and the heterologous protein, the peptide can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

A variety of prokaryotic or eukaryotic cells can be used as host-expression systems to express the polypeptide coding sequence. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence. Mammalian expression systems can also be used to express the polypeptides of the present invention. Bacterial systems are preferably used to produce recombinant polypeptides, according to the present invention, thereby enabling a high production volume at low cost.

Other expression systems such as insects and mammalian host cell systems, which are well known in the art can also be used by the present invention.

In any case, transformed cells are cultured under effective conditions, which allow for the expression of high amounts of recombinant polypeptides. Effective culture conditions include, but are not limited to, effective media, bioreactor, temperature, pH and oxygen conditions that permit protein production. An effective medium refers to any medium in which a cell is cultured to produce the recombinant polypeptides of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

Following a certain time in culture, recovery of the recombinant protein is effected. The phrase “recovering the recombinant protein” refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Polypeptides of the present invention can be used for treating an organophosphate exposure associated damage.

Thus according to an aspect of the invention there is provided a method of treating or preventing organophosphate exposure associated damage in a subject in need thereof, the method comprising providing the subject with a therapeutically effective amount of the isolated polypeptide described above to thereby treat the organophosphate exposure associated damage in the subject.

As used herein the term “treating” refers to preventing, curing, reversing, attenuating, alleviating, minimizing, suppressing or halting the deleterious effects of the immediate life-threatening effects of organophosphate intoxication and its long-term debilitating consequences.

As used herein the phrase “organophosphate exposure associated damage” refers to short term (e.g., minutes to several hours post-exposure) and long term damage (e.g., one week up to several years post-exposure) to physiological function (e.g., motor and cognitive functions). Organophosphate exposure associated damage may be manifested by the following clinical symptoms including, but not limited to, headache, diffuse muscle cramping, weakness, excessive secretions, nausea, vomiting and diarrhea. The condition may progress to seizure, coma, paralysis, respiratory failure, delayed neuropathy, muscle weakness, tremor, convulsions, permanent brain dismorphology, social/behavioral deficits and general cholinergic crisis (which may be manifested for instance by exacerbated inflammation and low blood count. Extreme cases may lead to death of the poisoned subjects.

As used herein the term “organophosphate compound” refers to a compound comprising a phosphoryl center, and further comprises two or three ester linkages. In some aspects, the type of phosphoester bond and/or additional covalent bond at the phosphoryl center classifies an organophosphorus compound. In embodiments wherein the phosphorus is linked to an oxygen by a double bond (PdbdO), the OP compound is known as an “oxon OP compound” or “oxon organophosphorus compound.” In embodiments wherein the phosphorus is linked to a sulfur by a double bond (PdbdS), the OP compound is known as a "thion OP compound" or "thion organophosphorus compound."

Additional examples of bond-type classified OP compounds include a phosphonocyanidate, which comprises a P—CN bond; a phosphoroamidate, which comprises a P—N bond; a phosphotriester, which comprises a $P(—O—R1)_3$ bond; a phosphodiester, which comprises a $P(—O—R)_2$ bond, where R is alkyl or aryl moieties; a phosphonofluoridate, which comprises a P—F bond; and a phosphonothiolate, which comprises a P—S-alkyl or P—S-alkyl-$N(R')_2$ bond, where R is any alkyl group. A "dimethoxy OP compound" comprises two methyl moieties covalently bonded to the phosphorus atom, such as, for example, malathion. A "diethyl OP compound" comprises two ethoxy moieties covalently bonded to the phosphorus atom, such as, for example, diazinon or paraoxon.

In general embodiments, an OP compound comprises an organophosphorus nerve agent or an organophosphorus pesticide.

As used herein the phrase "a subject in need thereof" refers to a human or animal subject who is sensitive to OP toxic effects. Thus, the subject may be exposed or at a risk of exposure- to OP. Examples include civilians contaminated by a terrorist attack at a public event, accidental spills in industry and during transportation, field workers subjected to pesticide/insecticide OP poisoning, truckers who transport pesticides, pesticide manufacturers, dog groomers who are overexposed to flea dip, pest control workers and various domestic and custodial workers who use these compounds, military personnel exposed to nerve gases.

As mentioned, in some embodiments of the invention the method is effected by providing the subject with a therapeutically effective amount of the PON1 polypeptide of the invention.

As OP can be rapidly absorbed from lungs, skin, gastrointestinal (GI) tract and mucous membranes, PON1 may be provided by various administration routes or direct application on the skin.

For example, PON1 may be immobilized on a solid support e.g., a porous support which may be a flexible sponge-like substance or like material, wherein the PON1 is secured by immobilization. The support may be formed into various shapes, sizes and densities, depending on need and the shape of the mold. For example, the porous support may be formed into a typical household sponge, wipe or a towelette.

For example, such articles may be used to clean and decontaminate wounds, while the immobilized PON1 will not leach into a wound. Therefore, the sponges can be used to decontaminate civilians contaminated by a terrorist attack at a public event.

Alternatively or additionally, PON1 may be administered to the subject per se or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the PON1 accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, dermal, transmucosal, especially transnasal, intestinal or parenteral delivery, including intramuscular, subcutaneous and intramedullary injections as well as intrathecal, direct intraventricular, intravenous, inrtaperitoneal, intranasal, intrabone or intraocular injections.

Alternately, one may administer the pharmaceutical composition in a local rather than systemic manner, for example, via injection of the pharmaceutical composition directly into a tissue region (e.g., skin) of a patient. Topical administration is also contemplated according to the present teachings.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (nucleic acid construct) effective to prevent, alleviate or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer (see the Examples section which follows). Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

PON1 may be administered prior to the OP exposure (prophylactically, e.g., 10 or 8 hours before exposure), and alternatively or additionally administered post exposure, even days after (e.g., 7 days) in a single or multiple-doses.

Embodiments of the invention also contemplate the use of other agents in combination with PON-1 for the treatment or prevention of OP damage. The following regimen is intended to encompass treatment with PON1 alone or in combination with other agents.

Thus, according to an exemplary embodiment, PON1 may be administered by inhalation to protect the lungs and injection (i.v.) to protect the circulation up to 2 hours post exposure. Atropine may be added 2-4 hours post exposure. Daily injections of PON1 may be administered up to 7 days post poisoning. Oximes like Hl-6 and mono-bisquaternary oximes such as pralidoxime chloride (2-PAM) may be added to improve treatment efficacy.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The ability of PON1 to sequester OP molecules, suggests use of same in the decontamination of OP contaminated surfaces and detoxification of airborne OP.

Thus, an aspect of the invention further provides for a method of detoxifying a surface contaminated with an OP molecule; or preventing contamination of the surface with OP. The method is effected by contacting the surface with PON1.

Thus, synthetic and biological surfaces contemplated according to embodiments of the invention include, but are not limited to, equipment, laboratory hardware, devices, fabrics (clothes), skin (as described above) and delicate membranes (e.g., biological). The mode of application will very much depend on the target surface. Thus, for example, the surface may be coated with foam especially when the surface comprises cracks, crevices, porous or uneven surfaces. Application of small quantities may be done with a spray-bottle equipped with an appropriate nozzle. If a large area is contaminated, an apparatus that dispenses a large quantity of foam may be utilized.

Coatings, linings, paints, adhesives sealants, waxes, sponges, wipes, fabrics which may comprise the PON1 may be applied to the surface (e.g., in case of a skin surface for topical administration). Exemplary embodiments for such are provided in U.S. Pat. Application No. 20040109853.

Surface decontamination may be further assisted by contacting the surface with a caustic agent; a decontaminating foam, a combination of baking condition heat and carbon dioxide, or a combination thereof. Sensitive surfaces and equipments may require non corrosive decontaminants such as neutral aqueous solutions with active ingredient (e.g., paraoxonases).

In addition to the above described coating compositions, OP contamination may be prevented or detoxified using an article of manufacture which comprise the PON1 immobilized to a solid support in the form of a sponge (as described above), a wipe, a fabric and a filter (for the decontamination of airborne particles). Chemistries for immobilization are provided in U.S. Pat. Application 20040005681, which is hereby incorporated in its entirety.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Constructing PON1 Gene Libraries by Random Mutagenesis.

Recombinant PON1 variant G3C9 (Gene bank entry: AY499193) was used as a template to create H115W and V346A amino acid mutations by primer designing. pET-Nes2-Bc and pET-Nes1-Fo primer (Table 9, below) was used to amplify 10 ng of template with a mutator Taq polymerase (mutazyme, Genemorph) in 25 μl of reaction mixture for 15 cycles. On average 1.7±0.65 amino acid mutations/gene with ~60% transition and ~40% transversion were found. The PCR product was treated with DpnI (to destroy the template plasmid), purified, and served as a template (10 ng) for another 15 cycles of nested PCR performed with Taq polymerase. The PCR products were digested with NcoI and NotI and cloned to pET32 vector with a C-terminal 6-His tag (FIG. 1).

Constructing PON1 Gene Libraries by Gene Shuffling.

The improved PON1 variants were separately amplified from their respective plasmids using Taq polymerase and primers pET-Nes2-Bc and pET-Nes1-Fo. To facilitate the removal of non-beneficial mutations, the PCR amplified wild-type PON1 gene was added at a 1:3 ratio to a mixture of PCR products from all the improved variants. Approximately 5 μg of purified DNA mixture in 50 μl reactions was digested with 0.01 U DNaseI (Takara) at 37° C. for 2, 4, and 6 min. The reactions were terminated with 15 μl of 0.5 M EDTA, and heating at 90° C. for 10 min, and were run on a 2% agarose gel. Fragments of 50-150 bps size were excised and purified using a gel extraction kit (Qiagen). The PON 1 gene was reassembled using 100 ng of purified DNA fragments and thermocycling in a 50 μl reaction mixture that contained 2.5 U Pfu Ultra (Stratagene). The cycling included: one denaturation step at 96° C. for 3 min, then 35 cycles composed of: (i) a denaturation step at 94° C. (30 s); (ii) nine successive hybridization steps separated by 3° C. each, from 65° C. to 41° C., for 1.5 min each (total 13.5 min), and (iii) an elongation step of 1.5 min at 72° C. Finally, a 10 min elongation step at 72° C. was performed. The assembly product was amplified by a nested PCR reaction with primers pET-Nes1-Bc and pET-Nes0-Fo. In this step, 1 μl of the assembly reaction was used as a template in a standard 50 μl PCR reaction. The purified PCR product was digested with Nco1 and Not1, and cloned into the pET32 vector with a C-terminal 6-His tag (FIG. 1).

Constructing PON1 Gene Libraries by Using Designed Oligonucleotides at Targeted Positions.

The PON 1 gene having H115W mutation was used as a template to construct a library using synthetic oligos by ISOR protocol. Briefly, H115W mutant gene was digested with DNaseI. Approximately 5 μg of purified DNA in 50 μl reactions was digested with 0.01 U DNaseI (Takara) at 37° C. for 2, 4, and 6 min. The reactions were terminated with 15 μl of 0.5 M EDTA, and heating at 90° C. for 10 min, and were run on a 2% agarose gel. Fragments of 50-150 bps size were excised and purified using a gel extraction kit (Qiagen). The PON 1 gene was reassembled using 100 ng of purified DNA fragments with oligonucleotides encoded one mutation and 20 flanking nucleotides matching the PON1 gene (Table 9, below). Assembly PCR was performed in a 50 μl reaction mixture that contained 2.5 U Pfu Ultra (Stratagene). The cycling included: one denaturation step at 96° C. for 3 min, then 35 cycles composed of: (i) a denaturation step at 94° C. (30 s); (ii) nine successive hybridization steps separated by 3° C. each, from 65° C. to 41° C., for 1.5 min each (total 13.5 min), and (iii) an elongation step of 1.5 min at 72° C. Finally, a 10 min elongation step at 72° C. was performed. The assembly product was amplified by a nested PCR reaction with primers pET-Nes1-Bc and pET-Nes0-Fo. In this step, 1 μl of the assembly reaction was used as a template in a standard 50 μl PCR reaction. The purified PCR product was digested with NcoI and NotI, and cloned into the pET32 vector with a C-terminal 6-His tag (FIG. 1).

Double Emulsion and Sorting by FACS.

Substitution libraries were sorted by compartmentalization of single *E. coli* cells, each expressing an individual library variant in double emulsion droplets, and sorting these droplets by fluorescent activated cell sorter (FACS), essentially as described (references are provided hereinbelow under the "Reference Section"). BL21 (DE3) cells possessing GFPuv gene in the genome were used for expression of the PON 1 under the T7 promoter. Plasmid DNA was transformed and grown while shaking at 250 RPM in 5 ml 2×YT media containing 100 μg/ml ampicillin and 1 mM $CaCl_2$, for 12 hrs at 30° C., followed by another 24 hrs at 20° C. The cells were centrifuged at 3000 g for 10 min at 4° C., resuspended in 2×YT, and kept for 1 hr at room temperature. They were then rinsed twice in 0.1 M Tris-HCl, 1 mM $CaCl_2$, 0.1 M NaCl, pH 8.0, resuspended in the same buffer, and passed through a 5 μm filter (Sartorius). Filtered cells were compartmentalized in the first emulsion (water-in-oil), and 100 mM solutions of CMP-MeCyC racemate or DEPCyC was added to the oil phase (0.8 μl, to a final concentration of 50 μM). The production of the second emulsion (water-in-oil-in-water) and sorting were performed as described. More than $10^6$ events, at 2000 events/sec, were stored using FACSAria (Becton-Dickinson) (FIG. 2). Events corresponding to single *E. coli* cells were gated by GFP emission (at 530 nm, using blue laser for excitation). Approximately 5000 events were sorted to 96-well plates containing 200 μl of 2×YT media (1000 events per well). The plates were immediately moved to 37° C., incubated for 1 hr while shaking at 250 rpm, plated on LB-agar plates containing 100 μg/ml ampicillin and 20 mM glucose, and grown overnight at 30° C. Recovery of the sorted cells was determined by comparing the number of colonies on the LB plates to the number of events sorted by the FACS, and was found to be 20-40%.

Screens in 96-Well Plates.

Randomly picked colonies were individually grown with shaking in 96-deep-wells plates, using 0.5 ml 2×YT medium containing 100 μg/ml ampicillin and 1 mM $CaCl_2$, for 8 hrs at 30° C., followed by another 16 hrs at 20° C. Several repeats of wild-type PON1 were grown as controls. Following growth ($OD_{600nm}$≈4), the plates were centrifuged at 3000 g for 15 mins at 4° C., and pellets were kept at −70° C. for few hours. The pellets were resuspended in 200 μl of lysis buffer (0.1M Tris-HCl pH 8.0, 1 mM $CaCl_2$, 10 μg/ml lysozyme (Sigma), 0.2% Triton x-100, and 5 units/ml benzonase (Novagen)), and lysed by shaking at 1300 rpm for 30 min at 37° C. The pellet was removed by centrifugation at 4000 rpm for 20 min at 4° C., and the supernatant was transferred to a new set of plates and stored at 4° C.

Apparent enzymatic rates ($v_0$) for different substrates were measured in a plate reader (Synergy-HT BioTek) using an appropriate volume of clarified lysates (0.1-10 μl depending on the substrate). 25 μM of IMP-MeCyC and CMP-MeCyC were used and release of coumarin was measured at 405 nm. In order to get $S_p$ isomer, 10-20 nM of 3B3 purified enzyme were used to cleave $R_p$ isomer from the 25 μM of racemic mixture. All rates were determined at the linear range of product release, and background rates (lysates containing no PON1) were subtracted to give the observed initial rate ($v_0$).

Enzymes Purification and Kinetics.

Variants exhibiting the highest rates with the target substrate were grown in 50 ml cultures; cells were harvested by centrifugation, resuspended, and disrupted by sonication. Ammonium sulfate was added to the lysate to 5 5% (wt/vol). The precipitate was dissolved and dialyzed against activity buffer (Tris-HCl 50 mM pH=8, $CaCl_2$ 1 mM, NaCl 50 mM, Tergitol 0.1%.) and purified on Ni-NTA (Novagen). Fractions were analyzed for paraoxonase activity and purity (by SDS-PAGE), pooled, dialyzed against activity buffer supplemented with 0.02% sodium azide, and stored at 4° C. Protein purity was typically 70-80% by SDS-PAGE gel. Variants 4E9 and rePON1 (G3C9) were further purified by FPLC purification using a mono-Q column (HiPrep 16/10 Q FF, GE healthcare) eluted by activity buffer with 250 mM NaCl, concentrated (vivaspin 20 MWCO 20 KDa), loaded on a gel filtration column (HiLoad 26/60 Superdex 75, GE healthcare) and dialyzed against activity buffer supplemented with 0.02% sodium azide for long term storage at 4° C. Protein purity was assessed to be >97% by SDS-PAGE gel. A range of enzyme concentrations (0.01-4 μM) and substrate concentrations was applied (from 0.3×$K_M$ up to 2-3×Km). Product formation was monitored spectrophotometerically in 96-well plates with 200-μl reaction volumes. For each purified variants, at least three independent repeats were done for kinetic parameters and values were determined by fitting the data directly to the Michaelis-Menten using KaleidaGraph (FIG. 3). The catalytic activity of evolved variants with $R_p$-CMP-coumarin was obtained by measuring kinetics of the 2nd phase observed with racemic CMP-coumarin after consumption of the $S_p$-CMP-coumarin by one of the $S_p$ evolved variants (e.g. variant OC9 at 30 nM). By measuring initial rates using several substrate concentrations, we could estimate the apparent $k_{cat}/K_M$ for this isomer.

Conversion of CMP-Coumarin to GF.

Caution: Although the total amount of the in situ generated cyclosarin (GF) in aqueous solution is non-hazardous, the reader should be aware of its high potency as inhibitor of AChE. CMP-coumarin (0.5 ml of 1 mM) was incubated at room temperature in 0.2 M NaF pH 5.0. The quantitative and completion of the conversion of CMP-coumarin to GF (about 30 min) was verified by monitoring the release of the coumarin leaving group, using 100-fold dilution in 50 mM Tris-buffer pH 8 and measuring the absorption at 400 nm (the molar absorption of free coumarin was $3.7\times10^4$ $M^{-1}$ $cm^{-1}$). The observed release of the coumarin was >95% of the calculated value. $^{31}$P-NMR also indicated the complete and full conversion of CMP-coumarin into CMP-F. This was apparent from the disappearance of the $^{31}$P signal attributed to CMP-coumarin (δ, 29.8 ppm) and the concomitant rise of a doublet centered at δ, 32.2 ppm with a $J_{P-F}$ value of 1045 Hz which is typical to O-alkyl methylphsphonofluoridates. To determine the concentration of the GF stock solution produced in 0.2 M NaF, a ~$10^5$-fold dilution into a known concentration (~5 nM) of *Torpedo californica* AChE (TcAChE) in 50 mM phosphate buffer pH 8.0, permitted to titrate the content of the toxic $S_p$ isomer of GF, which was found to be 0.43-0.48 mM (ca. half of the racemic GF generated from 1 mM racemic CMP-Coumarin). The conversion of the IMP-, and PNP-Coumarin analogs to the respective fluoridates, and the determination of the kinetic parameters, was similarly performed and monitored.

The formation of GF, and the irreversibility of the conversion process, were further validated by three experiments. Firstly, the bimolecular rate constant of the toxic isomer of the CMP-coumarin analog when inhibiting TcAChE was $3.3\times10^7$ $M^{-1}$ $min^{-1}$. In contrast, the in-situ generated GF exhibited a bimolecular rate constant of $1.3\times10^9$ $M^{-1}min^{-1}$). The 40-fold increase in the inhibition potency of TcAChE is consistent with what would be expected from the inhibition rate constant of AChE by authentic GF. Secondly, the half-life of the in situ generated GF in activity buffer (50 mM Tris, 1 mM $CaCl_2$, 0.1% Tergitol, pH 8.0) is 85 to 130 min (based on loss of anti-AChE activity; see below), while $t_{1/2}$ of $S_P$-CMP-coumarin under the same conditions is ~530 min. (The in situ generated GF solution were therefore freshly made before screening and kept in an ice bath until used). Thirdly, since the released coumarin was present in the reaction mixture, we aimed to exclude the possibility that the conversion is reversible, and that we were actually monitoring PON1-mediated hydrolysis of CMP-Coumarin and a subsequent shift in equilibrium. Therefore the effect of an excess of free coumarin on the hydrolysis of in-situ generated GF was tested (FIG. 4). The above described assay was repeated with 4 additional equivalents of coumarin (one equivalent was generated by the fluoride exchange). The results indicated a small reduction in catalytic activity ($1.15\times10^7$ to $0.96\times10^7$ $M^{-1}$ $min^{-1}$) of 4E9 on GF. Because reversibility is expected to result in higher rates in the presence of excess of coumarin, this result indicates that the reverse conversion of GF into CMP-coumarin does not occur under the assay conditions.

Determination of $k_{cat}/K_M$ Values with In-Situ Generated GF.

The GF stock was diluted 1000-fold in cold distilled water and then further diluted 20-fold into the 0.005 to 0.2 μM PON variant in activity buffer (Tris-HCl 50 mM pH=8, $CaCl_2$ 1 mM, NaCl 50 mM, Tergitol 0.1%.). The nominal racemic GF concentration was set to 40-50 nM. At various time intervals, the reaction mixture is diluted 10-fold into 2.5 nM TcAChE in 50 mM phosphate buffer pH 8.0, 25° C. The phosphate buffer that chelates calcium, and the dilution, quenched the PON1 activity with GF. Residual TcAChE activity was measured after 10 and after 20 min (to ascertain completion of inhibition) by aliquating 10 μl into 1 ml Ellman assay solution containing 1 mM acetylthiocholine as substrate. The %-inhibition of TcAChE by the same GF solution with out PON was considered as 100% anti-AChE potency attributed to the toxic isomer of GF. This %-inhibition decreased over time of incubation with PON1, and $k_{obs}$ was calculated by fitting the %-loss of anti-TcAChE potency versus time to a mono-exponential equation. The concentration of PON1 was set so that degradation of >50% of GF (i.e., gain of 50% AChE activity) occurred within less than 10 mins (although this was impossible with the poorly active variants such as wild-type-like rePON1-G3C9).

AChE Protection Assays.

The assays were performed by pre-incubation of the PON1 variant and the OP (as exemplified in the below protocol for CMP-Coumarin), or by direct competition of the PON1 variant and AChE, as exemplified in the second protocol with CMP-F. Briefly, randomly picked colonies of library variants were grown and lysed as above. Clarified cell lysates were diluted 1:4 in activity buffer, and 500 diluted lysate were mixed with 10 µl of 6 µM CMP-coumarin. The reactions were incubated (15 mins), and an equal volume of AChE solution (0.25 nM AChE, in PBS, 0.1% BSA) was added. Following 15 min's incubation, samples (20 µl) were mixed with Ellman's reagent and the AChE substrate (180 µl, 0.85 mM DTNB, 0.55 mM acetylthiocholine, in PBS), and initial rates were measured at 412 nm. Residual AChE activity was determined by comparing initial rates those without OP. The screen with CMP-F was performed with the following modifications: undiluted cell lysates were mixed with an equal volume of AChE solution (0.5 nM), and freshly made CMP-F was added to 1 µM final concentration. Reactions were incubated for 15 mins, and residual AChE activity was determined as above. The catalytic specificity ($k_{cat}/K_M$) of purified variants was measured by mixing the in situ prepared OP-fluoridates (40 nM) with purified PON1 variants (0.1-0.01 µM) in activity buffer. Samples of this reaction mix were taken at different times, diluted (1:10) with the AChE solution (4 nM AChE, 0.1% BSA, 1 mM EDTA, in PBS), incubated for 15 mins, and residual AChE activity was determined as above. The apparent $k_{cat}/K_M$ values were derived from the slope of the resulting single exponential curve.

Prophylactic Activity of 4E9 in a Mouse Model.

Eight weeks old male mice of strain C57BL/6J strain, were supplied under germ-free conditions by the Animal Breeding Center of The Weizmann Institute of Science (Rehovot, Israel). The mice were housed in a light- and temperature-controlled room. All animals were handled according to the regulations formulated by the Institutional Animal Care and Use Committee (application number 04590909-2). Prior to treatments, blood samples were taken (50-75 µl, retero-orbital) into heparin (10 µl, 1:10). Mice were then weighted (average weight 24.5 (gr)±2.2) and PON1 variant 4E9 or rePON1 (210-260 µg/ml, >97% pure in isotonic activity buffer: Tris 50 mM pH=8, $CaCl_2$ 1 mM, NaCl 100 mM, tergitol 0.02%) were injected i.v to the tail vein at different doses (1.1, 2.1 or 2.2 mg/kg). After 55' or 5 h55' blood samples were obtained as described and mice were reweighed. After 1 or 6 hours, intoxication was induced by a single i.v. administration of Sp-CMP-coumarin (26.5 [µg/ml], PBS) at a dose of 290 µg/Kg. All animals were observed closely for clinical signs following CMP-coumarin intoxication during the first 24 hours and were kept for at least 14 days before sacrifice. Control mice were injected i.v. to the tail vein with either: isotonic activity buffer (200 µl) or Atropine sulfate [20 mg/kg] and 2-PAM [25 mg/kg] in PBS just 5 min prior to intoxication as indicated. The toxicity of PON1 variant 4E9 or the isotonic activity buffer were assayed by injecting them to mice without an OP challenge, as described, and monitoring for at least 14 days. All clinical signs noted following Sp-CMP-coumarin intoxication were categorized to mild, moderate or severe reactions. Mild reactions were characterized by straub tail and ataxia. Moderate reactions consisted in addition decreased motor activity and tremors while animals with severe reactions exhibited in addition ventral position, fasciculation and dyspnea as well. The overall reactions observed following Sp-CMP-coumarin intoxication were scored using semi-quantitative grading of five grades (0-4), taking into consideration the severity of the reactions (0=No Reactions, 1=Mild Reactions, 2=Moderate Reactions, 3=Severe Reactions, 4=Mortality).

Example 2

Directed Evolution of PON1 for $S_P$-CMP Hydrolysis

Several variants of rePON1 with an enhanced activity towards a racemic mixture of CMP-Coumarin were previously isolated by screening 'neutral drift' libraries of rePON1 (e.g. 1G3, 2G9). The most active variant was found to be 3B3 with ~250-fold higher catalytic efficiency ($k_{cat}/K_M$ 20×10$^6$ $M^{-1}min^{-1}$) compared to the wild-type-like rePON1 ($k_{cat}/K_M$ 0.08×10$^6$ $M^{-1}min^{-1}$; Table 1b; Table 2 below). Although the hydrolysis by rePON1-3B3 was also restricted to the $R_P$ isomer (FIG. 6*a*), the high catalytic efficiency and $R_P$-stereoselectivity could be used to isolate the $S_P$ isomers of CMP-coumarin and IMP-coumarin from the corresponding racemates, and apply them for the subsequent screens. Low activity of rePON1 mutants H115W and V346A rePON1 towards $S_P$-CMP-coumarin was also identified. However, their activity with $S_P$-CMP-coumarin was too low for detection under library screening conditions. Therefore the first rounds IMP-coumarin, a less bulky G-agent analogue whose $S_P$ isomer is more reactive with PON1 were used (Table 2, below).

Random mutagenesis of rePON1-H115W-V346A and screening of the resulting library in 96-well plates with $S_P$-IMP-Coumarin yielded several improved variants that typically carried one mutation in addition to H115W and V346A (Table 3, below). A second round of mutagenesis and screening with $S_P$-IMP-Coumarin led to the isolation of variants in which V346A was removed and the H115W and F222S mutations dominated (Table 3, below). As the evolving variants became more reactive with the $S_P$ isomer, the 3$^{rd}$ generation library could be screened with both $S_P$-IMP- and $S_P$-CMP-Coumarin. Indeed, this round resulted in several variants with improved activities towards $S_P$-CMP-Coumarin (e.g. 3A7, 8C8; Table 1b; Table 4, below). However, since the 4$^{th}$ round of mutagenesis and screening yielded no further improvements, a structure-based targeted library was designed and subjected it to high-throughput screening (>10$^6$ variants per run) by FACS sorting, as described below.

Example 3

Highly Proficient Variants by FACS Screening of Double Emulsion Droplets

The targeted substitutions library was based on PON1's active-site structure. In particular, a recently obtained crystal structure of the re-G3C9-H115W indicated movements of several side-chains in response to this mutation, including those of residues 69, 134 which are in direct contact with W115, and of the more remote residues 346, 347 and 348. therefore a library was generated by randomizing these positions and those of residues 115 and 222 that were found to be mutated in all active variants of the $3^{rd}$ round (Table 4, below). An oligo spiking strategy was used that incorporated the randomizing oligos onto re-PON1-H115W in a combinatorial manner so that each library variant carried on average 4 mutated positions. Due to the intense level of mutagenesis, and the targeting of the active-site, the libraries comprised mostly inactive variants. To purge inactive library clones, we employed a high-throughput FACS screen using a fluorogenic phosphotriester dubbed DEPCyC that was found to correlate well with the activity with $S_p$-CMP-Coumarin[12]. *E. coli* cells transformed with the plasmid library were compartmentalized in water-in-oil emulsion droplets. The fluorogenic substrate was added, and the primary emulsion droplets were converted to double-emulsion droplets that were sorted by FACS. Cells in isolated droplets were plated, picked and assayed in 96-well plates for Sp-CMP-coumarin activity.

The most active variants isolated from this $5^{th}$ round (Table 5, below) carried mutations L69G/A and H134R, in addition to H115W and F222S that appeared in the previous rounds. These variants were shuffled, together with random mutagenesis at low rates (~1.7 amino acid exchanges per gene), and the resulting $6^{th}$ round library was sorted by FACS, and then screened in 96-well plates. The most improved variants carried five key mutations: L69G, H115W, H134R, F222S and T332S (Table 6, below). The best variant, 3D8 exhibited a $k_{cat}/K_M$ value of $1.2\times10^7$ $M^{-1}min^{-1}$ with $S_p$-CMP-coumarin (Table 1 below; FIG. 6*a*). Further, 3D8 and other variants from the $6^{th}$ round exhibited similar rates with both the $S_p$ and $R_p$ isomers as indicated by the complete hydrolysis of the racemic CMP-coumarin with monophasic kinetics (FIG. 6*a*). FIG. 6*b* shows how the toxic isomer ($S_p$) of a Cyclosarin coumarin analogue called CMP is hydrolyzed by different variants and the wild-type like rePON1 (G3C9) with time. We added the purified variants and the substrate at the indicated amounts and followed the hydrolysis by reading the increase in absorption of the coumarin leaving group with time. As can be seen, both rePON1 and 3B3 can hardly hydrolyze the substrate while 4E9 and 3D8 do so readily. FIG. 6*c* show how these variants hydrolyze the in-situ generated agent (Cyclosarin) termed here CMP-F as it is the fluoride derivative of CMP. Purified variants and the substrate were added at the indicated amounts and followed the hydrolysis by sampling the reaction at different time points and adding the samples to purified AChE. The residual AChE activity was used as a measure of the amount of substrate hydrolyzed sine they are correlated. As can be seen, variant 3B3 is the worst while 4E9 is the best hydrolyzer. By fitting the curve to a first-order equation we can derive the apparent rate constant for the hydrolysis of GF by these variants.

Example 4

Acetylcholinesterase Protection Assay

Along the selection for variants with higher rates, the concentration of the CMP-coumarin substrate was decreased to enable the isolation of variants with improved $K_M$ as well as $k_{cat}$. However, to be able to screen at concentrations that correspond to the very low toxic concentrations of cyclosarin in vivo (~1 μM)[3, 20], and for variants that efficiently degrade cyclosarin itself a screen was developed based on monitoring the rescue of AChE, the OP's physiological target. AChE was added to crude bacterial lysates expressing the library PON1 variants. The OP was added, and the residual activity of AChE was subsequently measured using a chromogenic assay to indicate the level of OP degradation by the tested variant. The FACS sorted $6^{th}$ round library was re-screened in 96-well plates using the AChE assay and 1 μM of racemic CMP-coumarin. 730 randomly-picked colonies were screened and 13 variants were isolated with improved activity by 2-12 fold relative to 3D8 (Table 7, below).

Although at this stage variants that exhibited sufficiently high catalytic proficiency were identified, these were selected and tested with coumarin surrogates. In fact, the fluoride leaving group of the actual threat agents substantially differs from coumarin (FIG. 5)—fluoride is more reactive and is a much smaller leaving group. However, the toxicity of nerve agents prevents their use in ordinary labs. Therefore a non-hazardous screening protocol was developed based on CMP-F generated in situ, in dilute aqueous solutions, by replacing the coumarin leaving group of CMP-coumarin with fluoride. This exchange was spectroscopically monitored by following the release of the coumarin. The inhibition of TcAChE by in situ generated CMP-F proceeded 40-fold faster than with $S_p$-CMP-Coumarin, with the expected k, of $1.3\times10^9$ $M^{-1}min^{-1}$. Using the in situ generated CMP-F, we measured the $k_{cat}/K_M$ values of the evolved variants under pseudo-first-order conditions (CMP-F≤50 nM, well under a likely $K_M$). Encouragingly, the activities with the coumarin and fluoridate $S_P$ isomers were comparable, and at least three variants (0C9, 2D8, 1A4) exhibited $k_{cat}/K_M$ values of ≥$10^7$ $M^{-1}min^{-1}$ with CMP-F (Table 8, below). The AChE protection assays therefore confirmed the ability of the evolved variants to protect AChE from cyclosarin in vitro, and validated the coumarin analogues as faithful surrogates of the actual G-agents. The assay also confirmed that the starting point, rePON1-G3C9 is much more active with CMP-F than CMP-Cuomarin (Table 1b), as is human PON1, although the $k_{cat}/K_M$ (~$10^5$ $M^{-1}min^{-1}$) is >100-fold too low for in vivo detoxification using reasonable amounts of enzyme.

The evolved variants were sufficiently active to enable library screens using the in situ generated agent. This approach is highly attractive, since the assay of AChE protection against the actual threat agent mimics the in vivo protection challenge whereby the catalytic scavenger must be sufficiently active to intercept the threat agent before the latter reacts with AChE. Therefore, the 13 most improved variants from the last round were re-screened using CMP-F at the expected plasma concentration for $1\times LD_{50}$ exposure (1 μM). Nine variants exhibited improved activities relative to 3D8 (Table 7, below). Of these, 3 variants (4E9, 5F3 and 6A3) exhibited the highest specific activity upon examination of the amount of soluble expressed protein.

Following sequencing and protein purification, 4E9 was identified as the most active variant with both $S_P$-CMP-coumarin and $S_P$-CMP-F ($k_{cat}/K_M$=$2.23\times10^7 M^{-1}min^{-1}$, and $1.7\times10^7$ $M^{-1}min^{-1}$, respectively; Table 1b below).

Example 5

Prophylactic Protection Assays

To validate that hydrolysis of the toxic isomer by a variant with $k_{cat}/K_M$ values of >$10^7$ $M^{-1}min^{-1}$ should protect against lethal OP exposure at a low protein dose, rePON1-4E9 was tested as a prophylactic in a mouse model. Due to safety issues, the CMP-Cuomarin surrogate was applied, but the challenge was upgraded by using the toxic somer only ($S_P$-CMP-coumarin) and by administrating it directly by i.v. injection. The results indicated a survival rate of 45% for mice pretreated with 1.1 mg/kg 4E9 one hour prior to the OP exposure (Table 10 below). Increasing the 4E9 dose to 2.2 mg/kg increased the percent of surviving animals to 75%, supporting the predicted correlation between $k_{cat}/K_M$ and in vivo and protection level. Twenty-four hours after exposure, the survival rate was 75% for mice receiving 4E9 either one, or six hours before the OP challenge. A similar survival ratio (63-75%) was observed 14 days later. As expected, the wild-type-like rePON1-G3C9 (estimated $k_{cat}/K_M$ for $S_p$-CMP-coumarin $\leq 2\times10^2$ $M^{-1}min^{-1}$), which served as a starting point for the directed evolution of 4E9, conferred no protection. Notably, treatment of mice with atropine and 2-PAM, even 5 minutes prior to challenge, gave very poor protection against the cyclosarin coumarin surrogate, as is the case with cyclosarin itself: the 24 h survival was only 22%, and there was no survival 96 h post challenge. Further, whereas 4E9 protected mice exhibited only mild intoxication symptoms 2-12 h after the challenge, all atropine plus 2-PAM treated mice displayed severe intoxication symptoms with no improvement until death.

TABLE 2

Activity of PON1 mutants with both isomers of CMP-coumarin and with Sp-IMP-coumarin

| Variants | $S_p$-CMP coumarin [a] ($k_{cat}/K_m$) $M^{-1}min^{-1}$ | $S_p$-IMP coumarin [a] ($k_{cat}/K_m$) $M^{-1}min^{-1}$ | $R_p$-CMP coumarin [a] × $10^6$ Apparent ($k_{cat}/K_m$) $M^{-1}min^{-1}$ | Non-Synonymous mutations [c] |
|---|---|---|---|---|
| Wild-type-like rePON1-G3C9 | <200 (1) [b] | n.d. | 0.08 ± 0.0034 (1) | — |
| H115W | 331 ± 39 (>1.6) | 1983 ± 30 (1) | 0.45 (6) ↑ | **H115W** |
| V346A | 885 ± 76 (>4.4) ↑ | 3633 ± 126 (1.8)↑ | 0.2 (2.5) ↑ | **V346A** |
| H115W + V346A | 813 ± 79 (>4.1) ↑ | 10140 ± 7 (5) ↑ | 0.4 (5) ↑ | **H115W, V346A** |

[a] For each variant, enzymatic activities ($k_{cat}/K_m$) were measured with purified proteins and denoted are the average ± standard deviation values obtained from the 3 independent repeats. The values without standard deviations had s.d. ≤ 20% of their values. Values in parentheses denoted the fold increase and decrease as compare to wt like rePON1 for either isomers of CMP and as compared to H115W for Sp-IMP. n.d. denotes non detectable activity.

[b] The catalytic efficiency was estimated as described in the "Reference Section"

[c] Denoted in bold are mutations in active-site residues.

TABLE 1b

Representative variants along the directed evolution process

| | | $S_P$-CMP-Coumarin [c] | | | $R_P$-CMP-Coumarin Apparent | $S_P$-CMP-F Apparent |
|---|---|---|---|---|---|---|
| Variant [a] | Mutations [b] | $k_{cat}$ ($min^{-1}$) | $K_M$ (μM) | $k_{cat}/K_M$ ($\mu M^{-1}min^{-1}$) | $k_{cat}/K_M$ [c] ($\mu M^{-1}min^{-1}$) | $k_{cat}/K_M$ [c] ($\mu M^{-1}min^{-1}$) |
| rePON1 G3C9 | (Wild-type-like) | nd | nd | <0.0002 (1) [d] | 0.08 ± 0.0034 (1) | 0.13 ± 0.03 (1) |
| 3B3 | N41D, S110P, **L240S**, H243R, F264L, N324D, **T332A** | nd | nd | <0.0002 (1) [d] | 20 ± 1.7 (250) ↑ | ~0.0001 |
| H115W-V346A | **H115W, V346A** | nd | nd | 0.0008 (>4) ↑ | 0.4 (5) ↑ | 0.02 ± 0.003 |
| 3A7 | V97A, **H115W**, P135A, **F222S**, M289I | nd | nd | 0.0027 (>13.5) ↑ | 0.16 (2) ↑ | 0.008 ± 0.0035 |
| 8C8 | **L69S**, V97A, **H115W**, P135A, **F222S** | 11.6 ± 0.18 | 124.5 ± 5.8 | 0.093 ± 0.003 (>465) ↑ | 0.0035 (23) ↓ | 0.2 (1.5) |
| 2D8 | **L69G**, **H115W**, **H134R**, **F222S**, **T332S** | 268 ± 1.6 | 76.3 ± 3.2 | 3.52 ± 0.13 (>17600) ↑ | 0.465 (5.8) ↑ | 14.3 (110) |
| 3D8 | **L69G**, **H115W**, **H134R**, M196V **F222S**, **T332S** | 295 ± 1.62 | 25.4 ± 0.5 | 11.6 ± 0.23 (>58000) ↑ | nd [e] | 3.3 (25) |
| 4E9 | **L69G**, S111T, **H115W**, **H134R**, **F222S**, **T332S** | 513 | 23 | 22.3 (>111500) ↑ | nd [e] | 16.8 (129) |

[a] Annotation of variants: The first digit relates to the plate number, and the following letter-digit to its location within this plate. For example, variant 3A7 = plate #3, well A7; n.d., not detectable.

[b] Denoted in bold are mutations in active-site residues.

[c] Enzymatic parameters were measured with purified proteins and comprise the average obtained from the 3 independent repeats. Error ranges represent the standard deviations observed between measurements. A more complete set of parameters including separate $k_{cat}$ and $K_M$ values when available, are provided in the Tables below. Values in parentheses describe the fold-change compare to the starting point, rePON-G3C9. The kinetic parameters for $S_P$-CMP-coumarin were spectrophotometerically measured with pure substrate samples[15]. Parameters for $R_P$-CMP-coumarin were determined with the racemate, and for CMP-F with the in situ prepared substrate and an AChE inhibition assay (see Methods for details).

[d] The catalytic efficiency was estimated in the reference section

[e] Variants exhibited a single-phase kinetics of product release when reacted with racemic CMP-coumarin, suggesting that the rates of hydrolysis for $R_P$-and $S_P$-CMP-coumarin are similar.

TABLE 3

Improved 1st and 2nd round variants from libraries derived from rePON1-H115W-V346A.

| Variants [a] | Round [b] | Fold improvement with $S_p$ -IMP-coumarin [c] | Non-Synonymous mutations [d] |
|---|---|---|---|
| 1G3 | 1 | 2x | H115W, P135A, V346A |
| 2A10 | 1 | 2.8x | I109T, H115W, S139P, V346A |
| 3G6 | 1 | 4.8x | F17S, H115W, V346A |
| 3F11 | 1 | 3.7x | H115W, V346A [e] |
| 4B8 | 1 | 5.6x | H115W, F347I |
| 5F2 | 1 | 3.3x | H115W, F222L, V346A |
| 5F11 | 1 | 2.5x | H115W, M289I, V346A |
| 6G1 | 1 | 5x | H115W, F222L, V346A |
| 6E3 | 1 | 3.1x | H115W, S139P, V167M, V346A |
| 6D10 | 1 | 4.3x | H115W, V346A [e] |
| 7F6 | 1 | 7.4x | H115W, F222S, D309N, V346A |
| 3A7 | 2 | 22x | V97A, H115W, P135A, F222S, M289I |
| 6D10 | 2 | 12x | H115W, F222S |
| 6G5 | 2 | 16x | L10S, H115W, P135A, F222S |

[a] The annotation or the variants: The first letter relates to the plate number, and the letter-digit to the location of the clone within this plate. For example, variant 1G3 = plate # 1, well G3.
[b] Round of mutagenesis and screening
[c] Shown are all variants that exhibited higher $S_p$-IMP-coumarin activity in crude cell lysates relative to the H115W + V346A PON1 mutant. For each variant, enzymatic activities were measured in crude lysate and denoted are the average values of fold improvement obtained from 3 independent repeats. The values had s.d. ≤ 20% of their value.
[d] Non-synonymous mutations observed in each variant. Mutations in active site residues are noted by underlined.
[e] These two variants had the same amino acid exchanges. The small differences in activity may relate to differences in the composition and number of synonymous mutations.

TABLE 4

Improved 3rd round variants from libraries derived from rePON1-H115W-V346A.

| Variants [a] | Fold improvement with $S_p$ -IMP-coumarin [b] | Fold improvement with $S_p$ -CMP-coumarin [b] | Non-Synonymous mutations [c] |
|---|---|---|---|
| 4D2 | 0.3x | 10x | L69S, H115W, P135A, F222S |
| 8C8 | 0.4x | 13x | L69S, V97A, H115W, P135A, F222S |
| 6C5 | 2x | 3x | V97A, H115W, P135A, F222S, M196V, M289I |
| 1A8 | 1.3x | 1.5x | L4P, V97A, H115W, P135A, F222S, M196V |
| 1E3 | 0.2x | 1.4x | A6T, V97A, H115W, P135A, F222S, D212N, M289I |
| 7G10 | 0.5x | 1.3x | L10S, H115W, F222S, M289I, V346A |
| 8H4 | 0.7x | 0.8x | V97A, H115W, P135A, F222S |
| 8H3 | 0.8x | 0.8x | V97A, H115W, P135A, F222S, I237V, L262F |
| 1G1 | 1.2x | 1.2x | V97A, H115W, F222S, M289I |

[a] The annotation of the variants: The first letter relates to the plate number, and the letter-digit to the location of the clone within this plate. For example, variant 4D2 = plate # 4, well D2.
[b] Shown are all variants that exhibited higher $S_p$ -IMP-coumarin and $S_p$ -CMP-coumarin activities in crude lysates relative to the H115W + V346A PON1 mutant. For each variant, enzymatic activities were measured in crude lysate and denoted are the average values of fold improvement obtained from 3 independent repeats. The values had s.d. ≤ 20% of their value.
[c] Non-synonymous mutations observed in each variant. Mutations in active site residues are noted by underline.

TABLE 5

Improved variants from the targeted substitutions library (5th round).

| Variants [a] | $S_p$ -CMP-coumarin [b] | Non-Synonymous mutations |
|---|---|---|
| 2F8 | 0.3x | T35A, L69S, H115W, F222N |
| 6H2 | 0.4x | L10S, L69G, H115W, H134K, F222S |
| 6C6 | 0.3x | L10S, L69S, H115W, P135A, F222S |
| 1D10 | 0.2x | L69G, H115W, H134T, F222L |
| 3G7 | 0.3x | L69G, H115W, F222L |
| 6B1 | 0.3x | H115W, F222V |
| 2G11 | 2x | L10S, L69G, H115W, P135A, F222S |
| 1H1 | 4x | L69G, H115W, H134R, F222C |
| 2H4 | 2x | L10S, L69A, H115W, H134R,F222S |
| 4H7 | 2x | L69G, H115W, F222S |

[a] The annotation of the variants: The first letter relates to the plate number, and the letter-digit to the location of the clone within this plate. For example, variant 2F8 = plate # 2, well F8..
[b] Shown are all variants that exhibited higher $S_p$-CMP-coumarin activities in crude lysates relative to the 8C8 mutant. For each variant, enzymatic activities were measured in crude lysate and denoted are the average values of fold improvement obtained from 3 independent repeats. The values had s.d. ≤ 20% of their value.
[c]Non-synonymous mutations observed in each variant. Mutations in active site residues are underlined.

TABLE 6

Improved variants from shuffling of the targeted substitutions library (6th round).

| Variant[a] | CMP(Sp)[b] $k_{cat}$ ($min^{-1}$) | CMP(Sp)[b] $K_m$ μM | CMP(Sp)[b] $k_{cat}/K_m$ $\mu M^{-1}min^{-1}$ | CMP[b] ($R_p$) $k_{cat}/K_m$ $\mu M^{-1}min^{-1}$ | CMP[b] (racemic) $k_{cat}/K_m$ $\mu M^{-1}min^{-1}$ | IMP[b] ($S_p$) $k_{cat}/K_m$ $\mu M^{-1}min^{-1}$ | EMP[b] ($S_p$) $k_{cat}/K_m$ $\mu M^{-1}min^{-1}$ | EMP[b] ($S_p$) $k_{cat}/K_m$ $\mu M^{-1}min^{-1}$ | Non-synonymous mutations[c] |
|---|---|---|---|---|---|---|---|---|---|
| 8C8 | 11.6 ± 0.18 | 124.5 ± 5.8 | 0.093 ± 0.003 (1) | 0.0035 (1) | 0.03 (1) | 0.022 (1) | 0.08 (1) | 0.2 (1) | **L69S**, V97A, **H115W**, P135A, **F222S** |
| 2C3 | 149.5 ± 0.87 | 212.7 ± 5.5 | 0.7 ± 0.01 (7.5) ↑ | 0.088 (25) ↑ | 0.62 (21) ↑ | 0.079 (3.6) ↑ | 0.88 (11) ↑ | 0.16 (1) | **L69G**, **H115W**, **H134R**, **F222S**, K233E |
| 5H5 | 126 ± 2 | 102 ± 3.8 | 1.25 ± 0.05 (13.4) ↑ | 0.2088 (60) ↑ | 2.43 (81) ↑ | 0.76 (35) ↑ | 3.8 (48) ↑ | 0.8 (4) ↑ | L10S, F28Y, **L69G**, **H115W**, **H134R**, **F222S**, T332S |
| 0C9 | 185 ± 2.5 | 65 ± 3.6 | 2.85 ± 0.1 (31) ↑ | 0.296 (85) ↑ | 3.56 (119) ↑ | 1.04 (47) ↑ | 6.67 (83) ↑ | 2.6 (13) ↑ | L14M, **L69G**, S111T, **H115W**, **H134R**, **F222S**, **T332S** |
| 2D8 | 268 ±1.6 | 76.3 ± 3.2 | 3.52 ± 0.13 (38) ↑ | 0.465 (133) ↑ | 3.04 (101) ↑ | 0.85 (39) ↑ | 6.8 (85) ↑ | 0.98 (5) ↑ | **L69G**, **H115W**, **H134R**, **F222S**, **T332S** |
| 1A4 | 185 ± 1.5 | 51 ± 1.7 | 3.63 ± 0.1 (39) ↑ | 0.39 (111)↑ | 3.11 (104) ↑ | 0.85 (39) ↑ | 7.15 (89) ↑ | 2.2 (11) ↑ | A6E, **L69G**, **H115W**, **H134R**, **F222S**, K233E, **T332S**, T326S |
| 3D8 | 295 ± 1.62 | 25.4 ± 0.5 | 11.6 ± 0.23 (125) ↑ | nd[d] | 4.73 (158)↑ | 4.6 (209) ↑ | 12 (150)↑ | 6.2 (31) ↑ | **L69G**, **H115W**, **H134R**, M196V, **F222S**, **T332S** |

[a]The annotation of variants: The first letter relates to the plate number, and the letter-digit to the location of the clone within this plate. For example, variant 3B3 = plate # 3, well B3.

[b]For each variant, enzymatic activities ($k_{cat}/K_m$) were measured with purified proteins and denoted are the average ± standard deviation values obtained from the 3 independent repeats. The individual values exhibited s.d. ≤ 20%. Values in parentheses denoted the fold increase and decrease as compare to 8C8, the best variant of the previous round.

[c]Denoted in bold are mutations in active-site residues.

[d]Variant exhibited a single-phase kinetics of product release when reacted with racemic CMP-coumarin, suggesting that the rates of hydrolysis for $R_P$-and $S_P$-CMP-coumarin are similar.

TABLE 7

PON1 variants selected using the AChE inhibition assay.

| | Variant name | CMP-coumarin hydrolysis activity [a] [fold over 3D8] | CMP-F hydrolysis activity [b] [fold over 3D8] |
|---|---|---|---|
| 1 | V-H10 | 11.6x | 4.3x |
| 2 | V-E2 | 11.0x | 6x |
| 3 | V-F3 | 8.8x | 6x |
| 4 | V-C11 | 8.3x | 6x |
| 5 | V-D6 | 7.2x | 3.4x |
| 6 | V-A6 | 6.2x | 2.1x |
| 7 | VIII-A12 | 2.3x | 3.3x |
| 8 | VIII-D1 | 2.1x | 5.5x |
| 9 | VI-G8 | 2.0x | 6x |
| 10 | VI-H12 | 1.7x | 2x |
| 11 | IV-H5 | 1.6x | 6x |
| 12 | IV-E9 | 1.6x | 1.6x |
| 13 | VI-A3 | 1.6x | 4.5x |

[a] The variants were tested using AChE (0.5 nM) with racemic CMP-coumarin (1 μM), and ranked relative to 3D8, isolated in Round 6 (Table 6).

[b] The variants were ranked relative to 3D8 using AChE (0.5 nM) and in-situ generated racemic CMP-F (1 μM)

TABLE 8

Activities of selected rePON1 variants on Sp-CMP-coumarin and its fluoridated product CMP-F (cyclosarin).[a,b,c,d]

| mutant | ($S_p$)CMP-coumarin | CMP-fluoridate | fluoridate/coumarin |
|---|---|---|---|
| 8C8 | 0.09 | 0.2 | 2.2 |
| 3D8 | 11.6 | 3.3 | 0.3 |
| 0C9 | 2.8 | 11.1 | 3.9 |
| 2D8 | 3.5 | 14.3 | 4.1 |
| 1A4 | 3.6 | 11.3 | 3.1 |
| 2C3 | 0.7 | 0.47 | 0.7 |

[a]The figures shown are values of $k_{cat}/K_M \times 10^6$ ($M^{-1}min^{-1}$)

[b]Data for OP-coumarin are based on release of the chromophore monitored at 400 nm.

TABLE 8-continued

Activities of selected rePON1 variants on Sp-CMP-coumarin and its fluoridated product CMP-F (cyclosarin).[a,b,c,d]

| mutant | ($S_p$)CMP-coumarin | CMP-fluoridate | fluoridate/coumarin |
|---|---|---|---|

[c]The $k_{cat}/K_m$ values for the fluoridates were determined by monitoring the rate of loss of anti-AChE potency of the in situ-generated compound, assuming $K_m$ >> [P-F]. Calculations are based on a single enzyme concentration selected to fit the dynamic range for determination of the apparent $k_{obs}$ of loss of anti-AChE potency.

[d]The coumarin leaving group was replaced by fluoride in racemic CMP-coumarin to yield the racemic fluoridates of CMP (CMP-F). Note that the data for the hydrolysis of CMP-F can be attributed mostly to the toxic (Sp) isomer of CMP-F.

TABLE 9

List of the oligonucleotides and primers

| Designation | Orientation | Primer sequence | SEQ ID NO: |
|---|---|---|---|
| pET-Nes2-Bc | Forward | 5'-GATGGCGCCCAACAGTCC-3' | 109 |
| pET-Nes1-Fo | Backward | 5'-GCGCGTCCCATTCGC-3' | 110 |
| pET-Nes0-Fo | Backward | 5'-TGATCTAGTGCGGCCGCCAGCTCA CAGTAAAGAGCTTTGTGAAACAC-3' | 111 |
| pET-Nes1-Bc | Forward | 5'-GTCCGGCGTAGAGGATCG-3' | 112 |
| L69NNS | | 5'-GGCTTTCATCAGCTCCGGANNSAA GTATCCTGGAATAATGAGC-3' | 113 |
| H115NNS | Forward | 5'-CTTCATTTAACCCTNNSGGGATTAG CACATTC-3' | 114 |
| H134NNS | Forward | 5'-CTACTGGTGGTAAACNNSCCAGAC TCCTCGTCC-3' | 115 |
| F222NNS | Forward | 5'-GTTGATTCCGTTAGCSNNATCAAAT CCTTCTGC-3' | 116 |
| V346NNS | Backward | 5'-GAGCTTTGTGAAASNNTGTGCCAA TCAGCAG-3' | 117 |

TABLE 9-continued

| List of the oligonucleotides and primers | | | |
|---|---|---|---|
| Designation | Orientation | Primer sequence | SEQ ID NO: |
| F247NNS | Backward | 5'-GTAAAGAGCTTTGTGSNNCACTGT GCCAATCAG-3' | 118 |
| H348NNS | Backward | 5'-CAGTAAAGAGCTTTSNNAAACACT GTGCCAATC-3' | 119 |

TABLE 10

Prophylactic protection in mice

| Time prior to OP challenge [hours] [a] | Treatment group [b] | Enzyme dose [e] [mg/kg] | % Survival recorded at: 12 h | 24 h | 96 h | 14 day |
|---|---|---|---|---|---|---|
| — | Untreated (12) | — | 0% | 0% | 0% | 0% |
| 1 | Buffer (3) [c] | — | 0% | 0% | 0% | 0% |
| 5 min | Atropine plus 2-PAM (9) [d] | — | 66% | 22% | 22% | 0% |
| 1 | rePON1 (18) | 2.2 | 0% | 0% | 0% | 0% |
| 1 | 4E9 (11) | 1.1 | 45% | 45% | 45% | 45% |
| 1 | 4E9 (16) | 2.2 | 75% | 75% | 63% | 63% |
| 6.3 | 4E9 (4) | 2.1 | 75% | 75% | 75% | 75% |

[a] $S_p$-CMP-coumarin was injected i.v. at 290 µg/kg to male mice weighing on average 24.5 ± 2.2 gr.
[b] Treatment given prior to OP challenge. All figures in parentheses relate to the number of mice in each group.
[c] Buffer content: Tris 50 mM pH 8, $CaCl_2$ 1 mM, NaCl 100 mM, Tergitol 0.02%.
[d] Atropine plus 2-PAM: Atropine sulfate [20 mg/kg] plus 2-PAM [25 mg/kg] in PBS.
[e] Purified rePON1-G3C9 or variant 4E9 (see Methods) were injected i.v. at the indicated dose prior to OP challenge.

Example 6

TABLE 11

Activities of Round 2 and Round 3 directly evolved PON1 variants selected for the hydrolysis of G-type nerve agents

| Variant | round | GD[a] $k_{cat}/K_m$ [$\mu M^{-1}min^{-1}$] Fast | Slow | GF $k_{cat}/K_m$ [$\mu M^{-1}min^{-1}$] | GB $k_{cat}/K_m$ [$\mu M^{-1}min^{-1}$] |
|---|---|---|---|---|---|
| VII-D11 | 2 | 29 | 29 | 10.7 | 1.2 |
| V-B3 | 2 | 26 | 6.8 | 12 | 0.5 |
| II-A1 | 2 | 25 | 7.3 | 5.9 | 0.7 |
| IV-D11 | 2 | 25 | 7.3 | 10.6 | 1.3 |
| MG2-I-A4 | 2 | 19.5 | 13 | 12.8 | 1.3 |
| VI-D2 | 2 | 14 | 3.3 | 2.8 | 0.2 |
| Average R2 | | 23.1 | 11.1 | 9.1 | 0.9 |
| PG11 | 1 | 14 | 3.2 | 2.12 | 0.2 |
| 5H8 | 1 | 5.7 | 0.64 | 2.44 | 0.1 |
| Average R1 | | 9.9 | 1.9 | 2.3 | 0.2 |
| 4E9 | 0 | 7.4 | 0.56 | 16.8 | 0.3 |
| 2D8 | 0 | 4.11 | 0.15 | 14.3 | 0.23 |
| 1A4 | 0 | 4.1 | 0.33 | 11.3 | 0.21 |
| 0C9 | 0 | 3.4 | 0.26 | 11.1 | 0.32 |
| 8C8 | 0 | 0.028 | 0.014 | 0.21 | 0.03 |
| Average R0 | | 3.8 | 0.3 | 10.7 | 0.2 |
| rePON1-G3C9 | — | 0.043 | 0.01 | 0.13 | 0.08 |

The figures shown are values of $k_{cat}/K_m$, $\mu M^{-1}min^{-1}$
[a]Fast and slow hydrolysis of the two equally toxic isomers of GD

TABLE 12

Key residues in the 2nd round variants listed in Table 4

| Amino Acid | wt-PON1 | II-A1 | MG2-IA4 | IV-D11 | VII-D11 | VI-D2 | VB3 |
|---|---|---|---|---|---|---|---|
| 64 | F | F | F | F | F | F | L |
| 69 | L | V | V | V | V | V | V |
| 115 | H | L | A | A | A | V | V |
| 134 | H | R | R | R | R | R | R |
| 196 | M | M | M | L | M | M | M |
| 222 | F | M | M | M | M | V | M |
| 309 | D | D | D | D | G | D | D |
| 332 | T | S | S | S | S | S | S |

$k_{cat}/K_m$ for Round 3 best mutants. G agents were at 0.5 µM and the enzymes at concentrations well below the OP, thus fulfilling the catalytic conditions for the hydrolysis of the nerve agents. Data shown ($\mu M^{-1}min^{-1}$), mean ± SD, n = 3.

TABLE 13

| Variant | GB | GD Fast | GD Slow | GF |
|---|---|---|---|---|
| 2-II-D12 | 1.80 ± 0.28 | 2.69 ± 0.14 | 2.69 ± 0.14 | 9.6 ± 1.5 |
| 1-I-D10 | 3.11 ± 0.63 | 8.73 ± 0.76 | 8.73 ± 0.76 | 21.1 ± 3.3 |
| I-IV-H9 | 3.13 ± 0.16 | 42.1 ± 5.0 | 42.1 ± 5.0 | 23.8 ± 1.5 |
| 1-I-F11 | 3.89 ± 0.38 | 44.3 ± 6.2 | 44.3 ± 6.2 | 45.8 ± 7.2 |
| Average of G3 | 3.0 | 24.5 | 24.5 | 25.1 |
| Average of G2 | 0.9 | 18.2 | 11.1 | 9.1 |
| Average of Gl | 0.17 | 6.7 | 1.3 | 4.7 |

1. A significant systematic improve across all G agents, when compared to libraries G1 and G2

Example 7

Round 4 PON1 Variants that have High Catalytic Efficiency for Detoxification of Organophosphates Materials and Methods Gene libraries. Recombinant PON1 variants cloned into a pET vector with a C-terminal 6-His tag (Gupta, et al., 2011) were used as the template for library construction using synthetic oligonucleotides and the ISOR protocol (Herman and Tawfik, 2007). Briefly, the genes of PON1 variants were PCR amplified, treated with DpnI (NEB) and purified. Purified DNA (20 µg in 150 µl) was digested with 0.3 U DNaseI (Takara) at 37° C. for 0.5, 1, 1.5 and 2 min. The reactions were terminated with 16 µl of 0.5 M EDTA, inactivated at 80° C. for 15 min, and run on 2% agarose gel. Fragments of 50-150 bps size were excised and purified by a gel extraction (Qiagen). The intact gene was reassembled by PCR from the DNA fragments (100 ng) with the addition of synthetic oligonucleotides (1-10 nM, as described in previous examples). The assembly product was amplified by nested PCR using primers pET-Nes1-Bc and pET-Nes0-Fo (Gupta, et al., 2011), purified, digested, (NcoI, NotI) and recloned into the pET32 vector.

Screening.

Plasmid transformed BL21/DE3 cells expressing PON1 variants were plated on LB-agar plates (plus 100 mg/l ampicillin and 1% glucose) and grown overnight at 37° C. Randomly picked colonies were individually grown in 96-deep-wells plates (500 µl 2YT per plate, plus ampicillin and $CaCl_2$ 1 mM) for 24 hrs at room temperature with shaking. The cells were pelleted and frozen (−80° C.). Cell pellets were defrosted, resuspended in lysis buffer (200 μl, 0.1M Tris-HCl pH 8.0, 1 mM $CaCl_2$, 10 μg/ml lysozyme, 0.2% Triton x-100, and 5 units/ml benzonase (Novagen)), lysed (1300 rpm, 45 min, 37° C.) and centrifuged (4000 rpm, 20 min, 4° C.). Clarified cell lysates (400) were mixed with an AChE solution (40 μl, 1 nM reAChE (Gupta, et al., 2011), in PBS, 0.1% BSA) in 96 well plates using an automated liquid-handling system (Precision 2000-BioTEk). In-situ generated G-agents (Gupta, et al., 2011) (20 μl, 0.1-1.5 μM) were added. Following a 30 min incubation, reaction samples (200) were mixed with the AChE substrate and DTNB (180 μl, 0.85 mM DTNB, 0.55 mM acetylthiocholine, in PBS) and initial rates were measured at 412 nm. The percentage of residual AChE activity was determined by comparing initial rates in the presence of the screened PON1 variants with to controls, without enzyme (full inactivation), no OP (no inactivation), and a reference variant from the previous round of evolution. Variants exhibiting residual AChE activity >2-fold greater than the reference variant were isolated, re-plated, and ≥3 individual clones were grown for verification assays and sequencing.

Enzyme Purification.

Cultures of BL21/DE3 plasmid transformed cells were grown ($OD_{600nm}$=0.5, 37° C.), induced (IPTG 1 mM, 4 h), harvested, resuspended, and disrupted by sonication. Ammonium sulfate was added (55% w/v). The precipitate was dissolved and dialyzed against activity buffer (Tris-HCl 50 mM pH 8, $CaCl_2$ 1 mM, NaCl 50 mM, Tergitol 0.1%) and purified on Ni-NTA (Novagen). Fractions were analyzed for purity (by SDS-PAGE), pooled, dialyzed against activity buffer supplemented with 0.02% sodium azide, and stored at 4° C. Protein purity was typically 70-85% by SDS-PAGE gel.

Determination of $k_{cat}/K_M$ by AChE Inhibition.

In situ generated agents (40 nM) (Gupta, et al., 2011) were mixed with purified PON1 variants (10-0.01 μM) in activity buffer. Samples of the reaction mixture were taken at different times, diluted (1:10) into an AChE solution (4 nM TcAChE, 0.1% BSA, 1 mM EDTA, in PBS), incubated 15 min), and their residual AChE activity was determined as described above. The %-inhibition of AChE by the G-agent without preincubation with a PON variant was considered as 100% inhibition attributed to the toxic isomers of the G-agents. Normalized %-inhibition values were derived for each time point, and the apparent $k_{cat}/K_M$ was derived from the slope of the resulting single exponential curve.

Determination of $k_{cat}/K_M$ Values with $S_p$/$R_p$-CMP-Coumarin.

$S_p$-CMP-coumarin was obtained by digestion of racemic CMP-coumarin with variant 3B3 that is $R_p$-CMP-coumarin specific (Ashani, et al., 2010), followed by organic extraction of the intact. $S_p$-CMP. $R_p$-CMP-coumarin was obtained in a similar manner using variant VIID2 that is $S_p$-CMP-coumarin specific. Purified variants (0.01-0.6 μM) were mixed with either $S_p$ or $R_p$-CMP-coumarin (5-1000 μM) in activity buffer in 96-well ELISA plates (200 μl per reaction). Product formation was monitored for 5 min at 405 nm and initial velocities were derived. Values of at least three independent repeats were averaged for determining the kinetic parameters of each variant by fitting the data directly to a Michaelis-Menten equation using KaleidaGraph. Substrate concentrations were verified by monitoring their complete hydrolysis using NaF (100 mM).

Kinetic Assay with PMP-Coumarin

Purified variants (0.5 μM) were mixed with racemic PMP-coumarin (10 μM) and activity buffer as above. The rate of PMP-coumarin hydrolysis was monitored by measuring the absorbance of released coumarin at 405 nm for up to 200 min. Alternatively, purified $R_p$-specific variant 3B3 (Ashani, et al., 2010) (0.5 μM) was mixed with racemic PMP-coumarin (10 μM) and activity buffer and product release was monitored for 50 min. Then, the newly evolved variants were added (0.5 μM) and product release was monitored for additional 150 min.

Kinetics of GA Hydrolysis by $^{31}$P NMR.

A Varian 300 MHz was used to monitor the changes in the $^{31}$P NMR signal of reaction mixtures. In an NMR tube, 0.15 ml $D_2O$ were added to 0.3 ml reactivity buffer containing 1 mg O,O-diisopropyl methylphosphonate and the solution was spiked with 50 μl of a GA stock solution in aceton to provide a final concentration of 1 mg/ml. After recording the baseline spectrum, the reaction was initiated by the addition of the corresponding PON1 variant. Twenty pulses were collected for each scan, data acquisition was repeated every 2-3 min.

Ex-Vivo Assays.

Protection of ChE's in human whole blood samples was measured as previously described. Briefly, purified PON1 variants (0.3-2.5 μM) were added to pre-heated (37° C.) human whole blood samples (obtained from the Israeli blood bank), spiked with $CaCl_2$ (to 2 mM) and adjusted to pH=7.4 with Tris base (1 M). At selected time intervals, freshly generated GF was added (to 0.1 μM) and the residual activity of blood ChEs was assayed as previously described (Ashani, et al., 2011). The ChE activity was compared to the residual ChEs activity obtained after 5 min incubation in blood. The hydrolytic activity of PON1 variants (0.3-2.5 μM) following incubation in whole blood (pH 7.4, $CaCl_2$ 2 mM) was evaluated by dilution of PON1 containing blood samples (1000-fold) at different time intervals into activity buffer, addition of racemic CMP-coumarin (0.3 mM), and measurement of the rate of hydrolysis as above. These rates were compared to the rates obtained after 5 min incubation.

Results

2D8 was chosen as the starting point for further evolution, the mutations of which are described in Table 15, herein below.

Library Design and Screening

The present inventors generated gene libraries derived from 2D8 by structure-guided targeted mutagenesis. This enabled them to generate smaller and more focused libraries that could be screened by a medium-throughput 96-well plate screen. Several strategies were applied, as detailed below.

Strategy 1: Targeted Diversification of Active-Site Residues.

Examining the structures of the unbound PON1 (PDB code 1V04 (Harel, et al., 2004)), of PON1 in complex with the inhibitor 2-hydroxyquinone (PDB code 3SRG (Ben-David, et al., 2011)), and of a docking model with the OP pesticide paraoxon (Ben-David, et al., 2011), indicated several active site positions that could affect OP binding and catalysis, including residues 70, 71, 196, 240 and 292 (Table 14).

TABLE 14

| Round | Mutagenesis strategy | Spiked mutations [a] | Shuffling | Screening/ Substrate | Fold improvement measured in crude cell lysates |
|---|---|---|---|---|---|
| 1 | 1 | Gly69Leu/Val/Ile/Ser Lys70Ala/Ser/Gln/Asn Tyr71Phe/Cyc/Ala/Leu/Ile Trp115Leu/Cyc/Gly/Ala/Val Arg134His/Gln/Asn Met196Leu/Ile/Phe Leu240Ile/Val Phe292Ser/Val/Leu | — | 2000 clones screened with GB, GD | 21 improved variants[b]. ≤4-fold with GB and ≤5-fold with GD relative to the starting point (2D8). Best variant: PG11 |
| 2 | 1 | Ser222Leu/Val/Ile/Met/Cys | 10 best clones from round 1 [c] | 1000 clones screened with GB, GD, GF | 25 improved variants [d]. ≤4 fold with GB, ≤2 fold with GD and ≤4 fold with GF relative to PG11. Best variant: VIID11. |
| 3 | 1 | Library 3.1 Asn50Gly/Ala Met196Phe/Ile His197Lys/Ser/Arg/Gln/Asn/Thr Ile291Phe/Trp/Leu Phe292Leu/Ile/Trp Tyr294Phe/Gln/Asn Val346Leu/Ile/Phe/Trp Phe347Gly/Ala/Ile/Leu/Val/Thr/Ser/Trp His348Gly/Ala/Ile/Leu/Val/Thr/Ser/Trp | 7 best clones from round 2 [e] | 400 clones from library 3.1 screened with GB and GD | 18 improved variants[f]. ≤4 fold with GB, ≤1.6 fold with GD relative to VIID11 Best variant: 1-I-F11 |
| 3 | 4 | Library 3.1: Leu55Ile/Met/Val Ile74Leu Asp136His/Gln Pro189Gly/Ser | | | |
| 3 | 3 | Library 3.2: Gly69Met/Ala Lys70Ser/Gln/Thr/Glu/Asp/Arg Tyr71Phe/Trp/Met/Cyc Pro72Gly/Ser Gly73Pro/Ser Ile74Trp/Phe/Pro/Ser/Gly Met75Leu/Trp/Phe/Pro Phe77Gly/Ala/Ile/Leu/Val/Thr/Ser/Trp/Ile/Leu/Met Asp78/Asn/Gln/Ser/Ala/Val/Tyr/Gly/Ser/Pro | 7 best clones from round 2 [e] | 400 clones from library 3.2 screened with GB and GD | |
| 4 | 2 | - No mutations spiked - | 18 best variants from round 3 [g] libraries 3.1 and 3.2 | 700 clones screened with GB and GD | 18 improved variants [h]. ≤2 fold with GB, ≤2 fold with GD relative to 1-I-F11 Best variant: IIG1 |

[a] The average frequency of random mutations in unselected library clones was 0.5 ± 0.3.
[b] See FIG. 8.
[c] See FIG. 9.
[d] See FIG. 10.

The present inventors also explored mutations in active-site residues that were substituted in the earlier rounds of directed evolution towards GF hydrolysis, including positions 69, 115, and 134. The library of variants was constructed by spiking mutations in these 8 active-site positions into the 2D8 gene in a combinatorial manner using the ISOR method (Herman and Tawfik, 2007). In general, residues were mutated to amino acids with similar physico-chemical properties although more drastic changes were also included (e.g. Gly69Leu/Val/Ile). Sequencing of randomly selected clones revealed that the unselected library contained on average 4±1 mutations per clone, with each clone exhibiting a different mutational composition. This Round 1 library was then screened with in-situ generated GD and GB, using the AChE inhibition assay (see materials and methods). This assay measures the ability of PON1 variants to prevent loss of AChE activity by rapidly hydrolyzing the toxic isomer of the added OP.

By the end of Round 1, all improved variants had acquired mutations at two positions, 69 and 115. Upon selection to a broader range of G-agents, these residues changed again. The improved variants carried additional mutations, primarily at positions 70, 71, 196, 240 or 292, but these varied from one variant to another (FIG. 8).

The changes in residues 69 and 115 led the present inventors to explore the re-optimization of another key active-site residue, 222, the mutagenesis of which to Ser had led to increased GF hydrolysis (see previous examples). Residue Ser222 was therefore targeted for mutagenesis in the $2^{nd}$ round library that was screened for neutralization of GB and GD, as well as GF (Table 14). Mutations to hydrophobic residues (Leu, Val, Ile, Met, or Cys) were explored. Indeed, 96% (24/25) of the improved variant from Round 2 were mutated in position 222, mostly to Met (17/24).

Positions 69, 115 and 222 that were substituted in the first two rounds reside at the bottom of PON1's active-site and close to the catalytic calcium. However, in the $3^{rd}$ round library, the present inventors targeted residues whose side-chains are involved in structuring the top of PON1's active site cleft. These included positions 50, 197, 291, 294, 346, 347 and 348. In addition, positions 196 and 292 that had been explored during the generation of the first round library but acquired no mutations were retargeted (Table 14). On average, variants in the unselected $3^{rd}$ round library contained 2±1 substitutions at the targeted positions. Following screening with GB and GD, the present inventors obtained 18 improved clones in which positions 197 and 291 were primarily mutated, although not in all variants (in 4/18 and 1/8 of the improved variants, respectively). Some positions did not accept any mutations (196, 294, 346, 347, 348), and others were mutated in single clones (50, 292).

Strategy 2: Shuffling of Improved Variants

Shuffling of selected variants can combine beneficial mutations that were acquired in separate variants and/or eliminate deleterious mutations from individual variants. In particular, since the mutational diversity in the present libraries was large compared to the number of clones screened (screening covered between 0.04 to 7% of the theoretical library diversity), the improved variants generally exhibited different mutational compositions (e.g. Round 3 in which no convergence was seen). In effect, shuffling of improved variants was applied in every round as part of the ISOR protocol (Herman and Tawfik, 2007) that was used to introduce the library mutations. For the Round 4 library, however, shuffling was applied with no spiking of targeted mutations (Table 14).

Strategy 3: Targeted Mutagenesis of the Flexible Active-Site Loop

PON1's longest active site loop (residues 70-78) is highly flexible and is disordered in the crystal structures of unbound PON1 (Harel, et al., 2004). Upon binding of the lactam inhibitor 2-hydroxyquinoline (2HQ), the loop became structured and thereby completes the active-site (Ben-David, et al., 2011). In particular, Tyr71 and Ile74 comprise part of the active-site wall and contact the inhibitor 2HQ. The loop configuration, and the position of Tyr71 in particular, seem to vary between different substrates (Ben-David, et al., 2011). Indeed, mutations in positions 70 (Lys to Asn or Gln) and 71 (Tyr to Phe or Ile) appeared in many improved clones from Round 1 (FIG. 8). Therefore, in addition to the library described above, the present inventors designed a second Round 3 library that explored active-site loop mutations. Given the very small size of the fluoride leaving-group of G-agents, the present inventors explored loop mutations that introduced large side-chains such as Trp, Phe and Tyr that could reduce the active site's volume and improve substrate binding. The present inventors also attempted to modulate the loop's configuration by exploring mutations to Gly and Pro (Table 14). Since mutations were introduced with oligonucleotides (21-29 bp) that flank the mutated codon, substitutions were mostly mutually exclusive and each clone carried, on average, only one loop mutation.

Strategy 4: Ancestral Mutations.

Ancestral mutations, i.e., substitutions into residues that appeared along the evolutionary history of a given protein, have been shown to be powerful modulators of a protein's stability and function (Alcolombri, et al., 2011; Bridgham, et al., 2006; Field and Matz, 2010). A library based on active-site substitutions from the predicted ancestors of mammalian PONs has been described (Alcolombri, et al., 2011). Screening this library with a coumarin analogue of GF (CMP-coumarin) led to the identification of several ancestral mutations that increase this activity. The present inventors included these mutations (Leu55Ile, Ile74Leu, Asp136His, Pro189Gly) together with similar ones (55Met/Val, 136Gln, 189Ser) in the Round 3 substitution library at an average frequency of. 0.5 mutations per gene in the unselected library (Table 14, herein above).

TABLE 15

| | Mutations relative to | | Catalytic efficiency[b] $(k_{cat}/K_M) \times 10^7\ M^{-1}min^{-1}$ | | | | |
|---|---|---|---|---|---|---|---|
| | | | GD[c] | | | | |
| Variant | rePON1[a] | Round | Fast | Slow | GF | GB | GA |
| rePON1 | — | — | 0.0055 ± 0.002 | 0.0015 ± 0.0006 | 0.013[d] ± 0.003 | 0.008 ± 0.001 | 0.043 ± 0.007 |
| 2D8 | Leu69Gly, His115Trp, His134Arg, Phe222Ser, Thr332Ser | 0 | 0.4 ± 0.1 | 0.015 ± 0.003 | 0.46[d] ± 0.01 | 0.025 ± 0.002 | 0.082 ± 0.005 |
| Fold improvement relative to (rePON1)[e] | | | (73) | (10) | (35) | (3) | (2) |
| PG11 | Leu69Val, His115Ala, His134Arg, Phe222Ser, Thr332Ser | 1 | 1.43 ± 0.3 | 0.32 ± 0.04 | 0.2 ± 0.03 | 0.02 ± 0.005 | 0.006 ± 0.001 |
| Fold improvement R1 relative to variant 2D8 (rePON1)[e] | | | 4 (260) | 21 (213) | 0.4 (15) | 0.8 (3) | 0.07 (0.1) |

TABLE 15-continued

| Variant | Mutations relative to rePON1[a] | Round | Catalytic efficiency[b] ($k_{cat}/K_M$) x $10^7$ $M^{-1}min^{-1}$ GD[c] Fast | Slow | GF | GB | GA |
|---|---|---|---|---|---|---|---|
| VII-D11 | Leu69Val, His115Ala, His134Arg, Phe222Met, Asp309Gly, Thr332Ser | 2 | 2.9 ± 0.9 | 2.9 ± 0.1 | 1.07 ± 0.08 | 0.12 ± 0.01 | 0.025 ± 0.003 |
| Fold improvement R2 relative to variant 2D8 (rePON1)[e] | | | 7 (527) | 193 (1933) | 2 (82) | 5 (15) | 0.3 (0.6) |
| 1-I-F11 | Leu55Met, Leu69Val, His115Ala, His134Arg, Phe222Met, Ile291Leu, Thr322Ser | 3 | 4.4 ± 0.6 | 4.4 ± 0.6 | 1.52 ± 0.1 | 0.39 ± 0.04 | 0.17 ± 0.04 |
| Fold improvement R3 relative to variant 2D8 (rePON1)[e] | | | 11 (800) | 293 (2933) | 3 (117) | 16 (49) | 2 (4) |
| IIG1 | Leu55Ile, Leu69Val, His115Ala, His134Arg, Asp136Gln, Phe222Met, Ile291Leu, Thr332Ser | 4 | 5.1 ± 0.6 | 5.1 ± 0.6 | 3.4 ± 0.3 | 0.32 ± 0.01 | 0.23 ± 0.004 |
| Fold improvement R4 relative to variant 2D8 (rePON1)[e] | | | 13 (927) | 340 (3400) | 7 (262) | 13 (40) | 3 (5) |

Directed Evolution of rePON1 for G-Agent Hydrolysis

Table 15, herein above summarizes the results of four rounds of directed evolution starting from variant 2D8 and screening for GB and GD hydrolysis. After screening ~2000 variants in Round 1, 21 clones were identified that in crude cell lysates were improved up to 4-fold with GB and up to 5-fold with GD relative to the starting point 2D8 (FIG. 8). The two most active variants with GD: 5H8, and PG11 were purified and characterized (Table 15 and 17). An improvement of 21- and 4-fold in the catalytic activity of the best variant PG11 with the two toxic isomers of GD relative to the starting variant 2D8 was found (Table 15). However, PG11's activity with GF was reduced 2.3-fold and its GB activity was the same as 2D8's. The two best variants shared the same 4 active site mutations: Leu69Val, His134Arg, Phe222Ser and Thr332Ser, but differed in position 115: variant 5H8 acquired a Val and variant PG11 an Ala. While mutations Phe222Ser and Thr332Ser were already present in the parental variant 2D8, the mutations in positions 69, 115 and 134 were selected from the substitution library of Round 1.

Table 16 herein below summarizes the catalytic activities of improved variants from each round of evolution.

TABLE 16

| Variant | Mutations relative to rePON1[a] | Round | Catalytic efficiency[b,d] ($k_{cat}/K_M$) x $10^7$ $M^{-1}min^{-1}$ GD[c] Fast | Slow | GF | GB |
|---|---|---|---|---|---|---|
| rePON1 | — | — | 0.0055 ± 0.0017 | 0.0015 ± 0.0006 | 0.013[e] ± 0.003 | 0.008 ± 0.001 |
| 8C8 | Leu69Ser, Val97Ala, His115Trp, Pro135Ala, Phe222Ser | 0 | 0.0028 ± 0.0006[f] (0.5) | 0.0014 ± 0.0004[f] (0.9) | 0.015[e] ± 0.005 (1.2) | 0.0034 ± 0.001 (0.4) |
| 0C9 | Leu14Met, Leu69Gly, Ser111Thr, His115Trp, His134Arg, Phe222Ser, Thr332Ser | 0 | 0.34 ± 0.03[f] (62) | 0.026 ± 0.0006[f] (17) | 1.11[e] ± 0.3 (85) | 0.028 ± 0.009 (4) |

TABLE 16-continued

| Variant | Mutations relative to rePON1[a] | Round | Catalytic efficiency[b,d] ($k_{cat}/K_M$) × $10^7$ $M^{-1}min^{-1}$ | | | |
|---|---|---|---|---|---|---|
| | | | GD[c] | | | |
| | | | Fast | Slow | GF | GB |
| 1A4 | Ala6Glu, Leu69Gly, His115Trp, His134Arg, Phe222Ser, Lys233Glu, Thr326Ser, Thr332Ser | 0 | 0.41 ± 0.07[f] (75) | 0.033 ± 0.004[f] (22) | 1.13[e] ± 0.3 (87) | 0.023 ± 0.003 (3) |
| 4E9 | Leu69Gly, Ser111Thr, His115Trp, His134Arg, Phe222Ser, Thr332Ser | 0 | 0.74 ± 0.3 (135) | 0.056 ± 0.01 (37) | 1.75[e] ± 0.3 (135) | 0.033 ± 0.004 (4) |
| 5H8 | **Leu69Val, His115Val,** His134Arg, Phe222Ser, Thr332Ser | 1 | 0.57 ± 0.04 (104) | 0.064 ± 0.03 (43) | 0.244 ± 0.012 (19) | 0.01 ± 0.008 (1) |
| VI-D2 | Leu69Val, His115Val, His134Arg, **Phe222Val,** Thr332Ser | 2 | 1.4 ± 0.2 (255) | 0.33 ± 0.2 (220) | 0.28 ± 0.017 (22) | 0.023 ± 0.001[f] (3) |
| MG2-I-A4 | Leu69Val, His115Ala, Hisl34Arg, **Phe222Met,** Thr332Ser | 2 | 1.95 ± 0.4 (355) | 1.3 ± 0.2 (867) | 1.28 ± 0.1 (98) | 0.13 ± 0.006 (16) |
| IV-D11 | Leu69Val, His115Ala, His134Arg, **Met196Leu, Phe222Met,** Thr332Ser | 2 | 2.5 ± 0.2 (455) | 0.73 ± 0.3 (487) | 1.06 ± 0.08 (82) | 0.12 ± 0.012 (16) |
| II-A1 | Leu69Val, **His115Leu,** His134Arg, **Phe222Met,** Thr332Ser | 2 | 2.5 ± 0.21 (455) | 0.73 ± 0.5 (487) | 0.59 ± 0.1 (45) | 0.07 ± 0.003[f] (9) |
| V-B3 | Leu69Val, His115Val, His134Arg, **Phe222Met,** Thr332Ser | 2 | 2.6 ± 0.1 (473) | 0.68 ± 0.5 (453) | 1.2 ± 0.5 (92) | 0.05 ± 0.003[f] (6) |
| 2-II-D12 | **Lys70Asn,** His115Leu, His134Arg, Phe222Met, Thr322Ser | 3 | 0.27 ± 0.014 (49) | 0.27 ± 0.014 (180) | 0.96 ± 0.15 (74) | 0.18 ± 0.028 (23) |
| 1-I-D10 | **Leu55Ile,** Leu69Val, His115Ala, His134Arg, Phe222Met, **Ile291Phe,** Thr322Ser | 3 | 0.87 ± 0.076 (158) | 0.87 ± 0.076 (580) | 2.11 ± 0.33 (162) | 0.31 ± 0.063 (39) |
| I-IV-H9 | **Leu55Ile,** Leu69Val, His115Leu, His134Arg, **Asp136His,** Phe222Met, **Ile291Leu,** Thr322Ser | 3 | 4.2 ± 0.5 (764) | 4.2 ± 0.5 (2800) | 2.38 ± 0.18 (183) | 0.31 ± 0.03 (39) |
| VH3 | Leu69Val, His115Ala, His134Arg, Phe222Met, Ile291Leu, Thr332Ser | 4 | 2.6 ± 0.2 (473) | 2.6 ± 0.2 (1733) | 2.8 ± 0.2 (215) | 0.3 ± 0.11 (38) |
| VIID2 | Leu55Ile, Leu69Val, His115Ala, | 4 | 3.7 ± 1 (673) | 3.7 ± 1 (2467) | 3.9 ± 1 (300) | 0.17 ± 0.014 (21) |

TABLE 16-continued

| Variant | Mutations relative to rePON1[a] | Round | Catalytic efficiency[b,d] ($k_{cat}/K_M$) × $10^7$ $M^{-1}min^{-1}$ | | | |
|---|---|---|---|---|---|---|
| | | | GD[c] | | | |
| | | | Fast | Slow | GF | GB |
| | His134Arg,<br>Hisl97Arg,<br>Phe222Met,<br>Ile291Leu,<br>Thr332Ser | | | | | |

[a]Mutations relative to the wild-type like rePON1 variant G3C9(Harel, et al., 2004). Mutations that were newly introduced in a given round are denoted in bold.

[b] Fold improvement relative to wt like rePON1. Errors of values were derived from at least two independent measurements. The maximal deviation between different enzyme preparations was ≤2 fold (measured for VIID2).

[c]Fast and slow hydrolysis of the two equally toxic isomers of GD ($S_CS_P$ and $R_CS_P$).

[d]Kinetic parameters were determined with the in situ generated G-agent and by assaying residual AChE activity. They therefore relate to the toxic $S_p$ isomer.

[e]Values from (Gupta, et al., 2011) Standard error.

For the 2nd round, a substitution library was constructed that explored various substitutions at position 222 whilst shuffling the 10 most active clones found in Round 1 (FIG. 9). The resulting library was screened for GD and GB, as well as GF. The latter was included to eliminate variants that exhibit reduced activity with GF, as observed with variants isolated from the 1st round. Of the ~1000 clones screened, 39 variants were isolated that were improved relative to the best variants of Round 1. Sequencing revealed 25 singular variants (FIG. 10). Following more detailed screens (at different agent concentrations and incubation times), the 6 most active variants were identified, purified and characterized. The purified variants exhibited up to 7- and 193-fold higher specific activities with the toxic isomers of GD, and up to 5-fold higher activities with GB, relative to the starting variant 2D8 (Table 15, Table 16). Their activities with GF were improved relative to variants from Round 1 and thereby became similar to that of 2D8. All Round 2 variants contained three mutations: Leu69Val, His 134Arg and Thr332Ser, and all but one contained also the Phe222Met mutation (Table 14, Table 16). The greatest variability was in position 115 in which either Ala, Leu or Val were observed. While no attempt to introduce random mutations during library construction was made, the PCR methodologies applied for library making, produced random mutations such as Phe64Leu or Asp309Gly that were retained in certain improved variants. By Round 2, the most improved variants reached the targeted catalytic efficiency of ≥$10^7$ $M^{-1}$ $min^{-1}$ with GD and GF, but were still 10-fold lower in activity with GB. The best Round 2 variant, VII-D11, hydrolyzed the two toxic isomers of GD with equally high rates (2.9×$10^7$ $M^{-1}min^{-1}$; Table 15).

In the 3$^{rd}$ round, two libraries were constructed and 400 variants from each library were screened with GD and GB (Table 13, FIG. 11). 18 improved clones were identified altogether. All these clones were improved with GB, but only 67% (12/18) were also improved with GD (FIG. 12). Most of the improved variants originated from Library #3.1 (73%, 13/18), and their improvements with GB (1.6-4-fold) were greater than with GD (1.1-1.6 fold). Sequencing indicated that 55% (10/18) of these improved variants contained at least one ancestral mutation (Leu55Ile, or Asp136His) and 28% (5/18) contained two ancestral mutations. In addition, the active-site mutation Ile291Leu became abundant (39%, 7/18). Certain mutations introduced in earlier rounds, His134Arg and Phe222Met, were fixed (i.e., appeared in all improved variants) and others—Leu69Val and His115Ala, were nearly fixed (90%, 16/18; FIG. 12).

The four most improved variants of Round 3 were purified and characterized. Relative to 2D8, the starting variant, their catalytic efficiencies were improved up to 11- and 293-fold with the two toxic isomers of GD, and up to 17-fold with GB (Table 15, Table 16). Although 2D8 was evolved for GF, a further ≤3-fold improvement with GF was identified in Round 3 variants. The catalytic efficiency of the most improved variant with GB (1-I-F11, 3.9×$10^6$ $M^{-1}min^{-1}$) was improved >3-fold relative to the best Round 2 variant.

In Round 4 (Table 14, FIG. 13), 700 clones were screened with GB and GD, and 22 improved variants were isolated of which 18 were singular (FIG. 14). Of these:

66% (12/18) were improved mostly with GB, and 33% (6/18) were improved also with GD. In addition to the mutations fixed in earlier rounds, His115Ala was fixed, and most variants also carried Leu55Ile (55%, 10/18) and/or Ile291Leu (83%, 15/18) (FIG. 14). 9 variants were purified and three variants identified that had improved relative to the starting variant 2D8 by ≤13- and ≤340-fold with the toxic isomers of GD, ≤7-fold with GB, and ≤9-fold with GF (Table 15, Table 16). As shown, their catalytic efficiencies with GF and GD were well over $10^7$ $M^{-1}min^{-1}$ (Table 15, Table 16, FIG. 15).

Neutralization of GA

The in-vivo toxicity of GA is >2-fold lower than that of all other G-agents (Benschop and Dejong, 1988), thus ranking it as the least threatening of the G-agents, and of lower priority for detoxification. In addition, its structure and leaving group are significantly different than that of all other G-agents (FIG. 7A), suggesting that variants that are improved for the three other G-agents might exhibit lower rates with GA, and vise versa. Thus, the libraries were not screened for GA neutralization, but the present inventors did examine the activity with GA of wild-type like rePON1, and of the most improved variants from the 4 rounds of evolution described here. Using the AChE inhibition assay, it was found that rePON1 is ≤40-fold more efficient at hydrolyzing the toxic isomer of GA than the toxic isomers of all other G-agents (Table 15). The most improved variants from Rounds 3 and 4 became 4 to 5-fold more efficient than rePON1 at hydrolyzing the toxic isomer of GA (1-I-F11 and IIG1; Table 15). Thus, although GA neutralization was not screened for, the catalytic efficiency of the present evolved variants with GA had increased and became similar to that with GB (~3×$10^6$ $M^{-1}min^{-1}$).

Stereospecificity of the Evolved Variants

The hydrolysis of G-agents was monitored using the AChE assay that only detects the hydrolysis of the toxic isomers ($S_p$ for GB, GD and GF, and Rp for GA). To examine the hydrolysis of both stereoisomers, the present inventors assayed the most improved variants from each round of directed evolution with the purified $R_p$ and $S_p$ isomers of the coumarin analogue of GF (CMP-coumarin; FIG. 7B). The results indicate that the evolution of higher detoxification rates of the three target G-agents (GB, GD and GF) was accompanied by a complete reversion in rePON1's stereoselectivity, as summarized in Table 17, herein below.

TABLE 17

| | | $S_P$-CMP-Coumarin | | | $R_P$-CMP-Coumarin | | | |
|---|---|---|---|---|---|---|---|---|
| Round # | Variant | $k_{cat}$ ($min^{-1}$) | $K_M$ (μM) | $k_{cat}/K_M$ ($uM^{-1}min^{-1}$) | $k_{cat}$ ($min^{-1}$) | $K_M$ (μM) | $k_{cat}/K_M$ ($uM^{-1}min^{-1}$) | E ($S_p/R_p$)[c] |
| — | rePON1 wild type like[a] | n.d.[b] | n.d.[b] | <0.0002 | 14.5 (±0.5) | 45 (±6) | 0.322 | <0.0006 |
| 1 | PG11 | 632 (±5) | 104 (±12) | 6.1 | 106 (±2.5) | 437 (±34) | 0.243 | 25 |
| 2 | VIID11 | 500 (±19) | 105 (±1) | 4.8 | 107.5 (±4) | 1307 (±155) | 0.082 | 59 |
| 3 | 1-I-F11 | 1004 (±98) | 83 (±4) | 12.1 | n.d.[b] | n.d.[b] | 0.0047 | 2575 |
| 4 | VIID2[d] | 1188 (±24) | 79 (±2) | 15 | 25.5 (±1.3) | 2658 (±419) | 0.0096 | 1563 |

[a]Values for rePON1 (G3C9) with $S_p$-CMP coumarin are from (Gupta, et al., 2011). Values with $R_p$-CMP coumarin update previous ones from (Gupta, et al., 2011) that were obtained with racemic-CMP-coumarin, using a purified $R_p$- substrate containing ≤2% $S_p$-CMP-coumarin.
[b]n.d.—not detectable.
[c]The enantiomeric ratio is the ratio of catalytic activity ($k_{cat}/K_M$) with $S_p$-CMP-Coumarin to the catalytic activity ($k_{cat}/K_M$) with Rp-CMP-Coumarin.
[d]See Table 16.

The catalytic efficiency ($k_{cat}/K_M$) of the wild-type-like rePON1 with $R_p$-CMP-coumain is >1600-fold higher than with $S_p$-CMP-coumarin. In contrast, the $k_{cat}/K_M$ values of the best variants from Rounds 3 and 4 with $S_p$-CMP-coumarin is >2500-fold higher than with $R_p$-CMP-coumarin (Table 17, FIGS. 16A-B).

The increase in $S_p/R_p$ stereoselectivity with CMP-coumarin was attributed to changes in both substrate binding and catalysis. In each round of evolution, a decrease in the $K_M$ value for $S_p$-CMP-coumarin and a concomitant increase in $k_{cat}$ value were observed. Parallel, increases in $K_M$ and decreases in $k_{at}$ values were observed with $R_p$-CMP-coumarin (Table 17). However, the change in the enantiomeric ratio (E; $k_{cat}/K_M(S_P)$ $k_{cat}/K_M(R_P)$) differed between rounds, with the greatest change occurring over the course of evolution leading from wild-type like rePON1 to the starting point variant 2D8. Here, the greatest change occurred in Round 3 variants. Interestingly, as far as indicated by the data for CMP-coumarin, this change was driven by a mild increase (~2-3-fold) in rate of hydrolysis of the $S_P$ isomer (that was selected for), and a far larger decrease in hydrolysis rate of the $R_P$ isomer (≤52-fold).

A similar trend was observed with the coumarin analogue of GD, PMP-coumarin (FIGS. 17A-B). As with other G-agents, the toxicity of GD is determined by the phosphorus chirality, and GD's two $S_p$ isomers ($S_pR_c$, $S_pS_c$; FIG. 7A) are >1000-fold stronger inhibitors of AChE than its two $R_p$ isomers (Benschop, et al., 1984). While the best Round 1 variant hydrolyzed all four diasteroisomers of PMP-coumarin at measurable rates, variants from Rounds 2 to 4 hydrolyzed only 50% of the racemic mixture (FIG. 17A). To confirm that the hydrolyzed fraction corresponds to the $S_p$ isomer pair, the present inventors applied the evolved rePON1 variant 3B3 that hydrolyzes almost exclusively the $R_p$ isomers of the coumarin G-agent analogues (Ashani, et al., 2010). Indeed, following the action of 3B3 that hydrolyzed only 50% of a racemic mixture of PMP-coumarin, the remaining 50% was readily hydrolyzed by evolved variants from Rounds 2-4 (FIG. 17B).

In order to examine the stereopreference of a variant towards GA, the present inventors followed its hydrolysis both by the AChE assay, which detects only the hydrolysis of the toxic $R_p$ isomer (Table 15) and by $^{31}$P-NMR (FIGS. 18A-B), which provides data on the hydrolysis of both isomers. The NMR data indicated that rePON1 hydrolyzes both isomers of GA with equal efficiency, while the starting point variant 2D8 displayed a sharp bi-phasic time-course behavior stemming from a strong stereo-preference for one isomer over the other (FIG. 18B). Since the catalytic efficiency ($k_{cat}/K_M$) value of 2D8 with the toxic $R_p$-GA isomer was comparable to the hydrolysis rate of the slow rather than the fast GA component in the $^{31}$P-NMR data, it was assumed that 2D8 is more efficient at hydrolyzing the non-toxic $S_P$ isomer of GA. Evolved Round 4 variant (VIID2) displayed an almost equal reactivity towards both isomers of GA with an apparent rate constant ratio of less than 4 (FIG. 18B). To summarize, the AChE assay indicated that rePON1 and 2D8 hydrolyze the toxic $R_p$ isomer of tabun with similar efficiencies, $4.3\times10^5$ and $8.2\times10^5$ $M^{-1}min^{-1}$, respectively, while variant VIID2 had improved at $R_p$ isomer hydrolysis ($1.83\times10^6 M^{-1}min^{-1}$).

Activity and Stability in Human Blood Samples

The use of evolved PON1 variants as prophylactic drugs depends on their ability to maintain activity in human blood over long periods of time. Variants PG11, VIID11, 1-I-F11 and VIID2 (from Rounds 1-4 respectively) were added to human blood samples and incubated at 37° C. In situ generated GF was added at different time intervals and the residual ChE activity was measured (FIG. 19A). Due to its low catalytic efficiency, Round 1 variant PG11 could not provide measurable ChE protection at the concentration range used (0.5-2.1M). However, variants VIID11, 1-I-F11 and VIID2 showed measurable ChE protection (41-45%). Further, these variants maintained 80-95% of their initial protection activity in human blood after 24 h of incubation at 37° C. (FIG. 19A).

Assaying the rate of hydrolysis of the chromogenic analogue of GF, CMP-coumarin, at different time intervals following incubation in whole blood (FIG. 19B) or buffer (FIG. 20) gave very similar results. This assay also indicated that the activity of all variants was mildly increased after 1 h incubation (4-12% relative to their activity after 5 min). This effect is in most likelihood the result of binding of the rePON1 variants to the HDL (high-density lipoprotein) particles in blood (Gaidukov and Tawfik, 2005). Taken together, these results suggest that the interaction of the evolved PON1 variants with human blood constituents did not affect their proficiency ex vivo within 24 hours.

Neutralization of VX

Chemical warfare nerve agents are generally divided into G-agents and V-agents (Romano, et al., 2008). While most G-agents have a small and highly reactive fluoride leaving group ($pK_a$=3.1), V-type agents have a bulky and far less reactive N,N-dialkylaminoethyl-thiol leaving group ($pK_a$=7.9) (Bracha and O'Brien, 1968) (FIG. 7A). V-agents pose a greater threat due to their increased toxicity and as such are prime targets for detoxification. However, the hydrolysis of the toxic $S_p$ isomer of VX by wild-type-like rePON1, and by human PON1 (unpublished results), is below the detection limits <2 $M^{-1}min^{-1}$. Upon longer incubations with high enzyme concentrations, stoichiometric neutralization of VX may occur, possibly by reacting with Cys284 and thereby inactivating the enzyme (Sorenson, et al., 1995; Tavori, et al., 2011). The catalytic efficiencies of variants VIID2 and VH3 with $S_p$-VX are 132 and 286 $M^{-1}$ $min^{-1}$, respectively. Thus, although these variants were evolved for broad range G-agent hydrolysis, they also exhibit >100-fold higher rates than wild-type PON1 for VX neutralization.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES FOR EXAMPLES 1-6

(Other References are Cited Throughout the Application)

1. Doctor, B. P. & Saxena, A. Bioscavengers for the protection of humans against organophosphate toxicity. Chem Biol Interact 157-158, 167-71 (2005).
2. Lenz, D. E. et al. Stoichiometric and catalytic scavengers as protection against nerve agent toxicity: a mini review. Toxicology 233, 31-9 (2007).
3. Ashani, Y. & Pistinner, S. Estimation of the upper limit of human butyrylcholinesterase dose required for protection against organophosphates toxicity: a mathematically based toxicokinetic model. Toxicol Sci 77, 358-67 (2004).
4. Ditargiani, R. C., Chandrasekaran, L., Belinskaya, T. & Saxena, A. In search of a catalytic bioscavenger for the prophylaxis of nerve agent toxicity. Chem Biol Interact [Epub ahead of print] (2010).
5. Ghanem, E. & Raushel, F. M. Detoxification of organophosphate nerve agents by bacterial phosphotriesterase. Toxicol Appl Pharmacol 207, 459-70 (2005).
6. Hill, C. M., Li, W. S., Thoden, J. B., Holden, H. M. & Raushel, F. M. Enhanced degradation of chemical warfare agents through molecular engineering of the phosphotriesterase active site. J Am Chem Soc 125, 8990-1 (2003).
7. Mee-Hie Cho, C., Mulchandani, A. & Chen, W. Functional analysis of organophosphorus hydrolase variants with high degradation activity towards organophosphate pesticides. Protein Eng Des Sel 19, 99-105 (2006).
8. Melzer, M. et al. Reversed enantioselectivity of diisopropyl fluorophosphatase against organophosphorus nerve agents by rational design. J Am Chem Soc 131, 17226-32 (2009).
9. Ashani, Y., Rothschild, N., Segall, Y., Levanon, D. & Raveh, L. Prophylaxis against organophosphate poisoning by an enzyme hydrolysing organophosphorus compounds in mice. Life Sci 49, 367-74 (1991).
10. Broomfield, C. A. A purified recombinant organophosphorus acid anhydrase protects mice against soman. Chem Biol Interact 87, 279-84 (1993).
11. Li, W. F., Furlong, C. E. & Costa, L. G. Paraoxonase protects against chlorpyrifos toxicity in mice. Toxicol Lett 76, 219-26 (1995).
12. Kassa, J., Karasova, J. Z., Caisberger, F. & Bajgar, J. The influence of combinations of oximes on the reactivating and therapeutic efficacy of antidotal treatment of soman poisoning in rats and mice. Toxicol Mech Methods 19, 547-51 (2009).
13. Harvey, S. P. et al. Stereospecificity in the enzymatic hydrolysis of cyclosarin (GF). Enzyme and Microbial Technology 37, 547-555 (2005).
14. Li, W. S., Lum, K. T., Chen-Goodspeed, M., Sogorb, M. A. & Raushel, F. M. Stereoselective detoxification of chiral sarin and soman analogues by phosphotriesterase. Bioorg Med Chem 9, 2083-91 (2001).
15. Amitai, G. et al. Enhanced stereoselective hydrolysis of toxic organophosphates by directly evolved variants of mammalian serum paraoxonase. Febs J 273, 1906-19 (2006).
16. Aharoni, A. et al. Directed evolution of mammalian paraoxonases PON1 and PON3 for bacterial expression and catalytic specialization. Proc Natl Acad Sci USA 101, 482-7 (2004).
17. Gaidukov, L. et al. In vivo administration of BL-3050: highly stable engineered PON1-HDL complexes. BMC Clin Pharmacol 9, 18 (2009).
18. Ashani, Y. et al. Stereo-specific synthesis of analogs of nerve agents and their utilization for selection and characterization of paraoxonase (PON1) catalytic scavengers. Chem Biol Interact [Epub ahead of print] (2010).
19. Gupta, R. D. & Tawfik, D. S. Directed enzyme evolution via small and effective neutral drift libraries. Nat Methods 5, 939-42 (2008).
20. Aharoni, A., Amitai, G., Bernath, K., Magdassi, S. & Tawfik, D. S. High-throughput screening of enzyme libraries: thiolactonases evolved by fluorescence-activated sorting of single cells in emulsion compartments. Chem Biol 12, 1281-9 (2005).
21. Mastrobattista, E. et al. High-throughput screening of enzyme libraries: in vitro evolution of a beta-galactosidase by fluorescence-activated sorting of double emulsions. Chem Biol 12, 1291-300 (2005).
22. Herman, A. & Tawfik, D. S. Incorporating Synthetic Oligonucleotides via Gene Reassembly (ISOR): a versatile tool for generating targeted libraries. Protein Eng Des Sel 20, 219-26 (2007).
23. Romano, J. A., Lukey, B. J. & Salem, H. Chemical warfare agents: chemistry, pharmacology, toxicology, and therapeutics (CRC Press, Boca Raton, 2008).
24. Amitai, G. et al. Asymmetric fluorogenic organophosphates for the development of active organophosphate hydrolases with reversed stereoselectivity. Toxicology 233, 187-98 (2007).
25. Luo, C., Chambers, C., Yang, Y. & Saxena, A. Mechanism for potent reactivation ability of H oximes analyzed by reactivation kinetic studies with cholinesterases from different species. Chem Biol Interact Epub ahead of print (2010).
26. Reetz, M. T., Kahakeaw, D. & Lohmer, R. Addressing the numbers problem in directed evolution. Chembiochem 9, 1797-804 (2008).
27. Fox, R. J. et al. Improving catalytic function by ProSAR-driven enzyme evolution. Nat Biotechnol 25, 338-44 (2007).

28. Shapiro, M. G. et al. Directed evolution of a magnetic resonance imaging contrast agent for noninvasive imaging of dopamine. Nat Biotechnol 28, 264-70 (2010).

29. Masson, P., Nachon, F. & Rochu, D. [Engineering of catalytic bioscavengers of organophosphorus compounds]. Bull Acad Natl Med 191, 95-111; discussion 112 (2007).

30. Miller, O. J. et al. Directed evolution by in vitro compartmentalization. Nat Methods 3, 561-70 (2006).

31. Aharoni, A., Amitai, G., Bernath, K., Magdassi, S. & Tawfik, D. S. High-throughput screening of enzyme libraries: thiolactonases evolved by fluorescence-activated sorting of single cells in emulsion compartments. Chem Biol 12, 1281-9 (2005).

32. Amitai, G., Gupta, R. D. & Tawfik, D. S. Latent evolutionary potentials under the neutral mutational drift of an enzyme. Hfsp J 1, 67-78 (2007).

33. Segall, Y. et al. Direct observation and elucidation of the structures of aged and nonaged phosphorylated cholinesterases by 31P NMR spectroscopy. Biochemistry 32, 13441-50 (1993).

34. Blum, M. M., Timperley, C. M., Williams, G. R., Thiermann, H. & Worek, F. Inhibitory potency against human acetylcholinesterase and enzymatic hydrolysis of fluorogenic nerve agent mimics by human paraoxonase 1 and squid diisopropyl fluorophosphatase. Biochemistry 47, 5216-24 (2008).

35. Ellman, G. L., Courtney, K. D., Andres, V., Jr. & Feather-Stone, R. M. A new and rapid colorimetric determination of acetylcholinesterase activity. Biochem Pharmacol 7, 88-95 (1961).

36. Perrier, M. G. a. D. Pharmacokinetics (ed. DeVane, C. L.) (Marcel Dekker, New York, 1982).

37. Laub, P. B. & Gallo, J. M. NCOMP—A windows-based computer program for noncompartmental analysis of pharmacokinetic data. Journal of Pharmaceutical Sciences 85, 393-395 (1996).

REFERENCES FOR EXAMPLE 7

Aharoni, A., Gaidukov, L., Yagur, S., Toker, L., Silman, I., and Tawfik, D. S. (2004). Directed evolution of mammalian paraoxonases PON1 and PON3 for bacterial expression and catalytic specialization. Proc Natl Acad Sci USA 101, 482-487.

Alcolombri, U., Elias, M., and Tawfik, D. S. (2011). Directed evolution of sulfotransferases and paraoxonases by ancestral libraries. Journal of molecular biology 411, 837-853.

Amitai, G., Adani, R., Yacov, G., Yishay, S., Teitlboim, S., Tveria, L., Limanovich, O., Kushnir, M., and Meshulam, H. (2007). Asymmetric fluorogenic organophosphates for the development of active organophosphate hydrolases with reversed stereoselectivity. Toxicology 233, 187-198.

Amitai, G., Gaidukov, L., Adani, R., Yishay, S., Yacov, G., Kushnir, M., Teitlboim, S., Lindenbaum, M., Bel, P., Khersonsky, O., et al. (2006). Enhanced stereoselective hydrolysis of toxic organophosphates by directly evolved variants of mammalian serum paraoxonase. Febs J 273, 1906-1919.

Ashani, Y., Goldsmith, M., Leader, H., Silman, I., Sussman, J. L., and Tawfik, D. S. (2011). In vitro detoxification of cyclosarin in human blood pre-incubated ex vivo with recombinant serum paraoxonases. Toxicology letters 206, 24-28.

Ashani, Y., Gupta, R. D., Goldsmith, M., Silman, I., Sussman, J. L., Tawfik, D. S., and Leader, H. (2010). Stereo-specific synthesis of analogs of nerve agents and their utilization for selection and characterization of paraoxonase (PON1) catalytic scavengers. Chemico-biological interactions 187, 362-369.

Ashani, Y., and Pistinner, S. (2004). Estimation of the upper limit of human butyrylcholinesterase dose required for protection against organophosphates toxicity: a mathematically based toxicokinetic model. Toxicol Sci 77, 358-367.

Bartsch, S., Kourist, R., and Bornscheuer, U. T. (2008). Complete inversion of enantioselectivity towards acetylated tertiary alcohols by a double mutant of a *Bacillus subtilis* esterase. Angew Chem Int Ed Engl 47, 1508-1511.

Ben-David, M., Elias, M., Filippi, J-J., Duñach, E., Silman, I., Sussman, J. L., and Tawfik, D. S. (2011). Catalytic versatility and redundancy in enzyme active-sites: The case of serum paraoxonase 1. J Am Chem Soc Submitted.

Benschop, H. P., and Dejong, L. P. A. (1988). Nerve Agent Stereoisomers—Analysis, Isolation, and Toxicology. Accounts Chem Res 21, 368-374.

Benschop, H. P., Konings, C. A., Van Genderen, J., and De Jong, L. P. (1984). Isolation, anticholinesterase properties, and acute toxicity in mice of the four stereoisomers of the nerve agent soman. Toxicology and applied pharmacology 72, 61-74.

Bird, S. B., Dawson, A., and Ollis, D. (2010). Enzymes and bioscavengers for prophylaxis and treatment of organophosphate poisoning. Front Biosci (Schol Ed) 2, 209-220.

Blum, M. M., Timperley, C. M., Williams, G. R., Thiermann, H., and Worek, F. (2008). Inhibitory potency against human acetylcholinesterase and enzymatic hydrolysis of fluorogenic nerve agent mimics by human paraoxonase 1 and squid diisopropyl fluorophosphatase. Biochemistry 47, 5216-5224.

Boersma, Y. L., Pijning, T., Bosma, M. S., van der Sloot, A. M., Godinho, L. F., Droge, M. J., Winter, R. T., van Pouderoyen, G., Dijkstra, B. W., and Quax, W. J. (2008). Loop grafting of *Bacillus subtilis* lipase A: inversion of enantioselectivity. Chemistry & biology 15, 782-789.

Bracha, P., and O'Brien, R. D. (1968). Trialkyl phosphate and phosphorothiolate anticholinesterases. I. Amiton analogs. Biochemistry 7, 1545-1554.

Bridgham, J. T., Carroll, S. M., and Thornton, J. W. (2006). Evolution of hormone-receptor complexity by molecular exploitation. Science 312, 97-101.

Broomfield, C. A., Lockridge, O., and Millard, C. B. (1999). Protein engineering of a human enzyme that hydrolyzes V and G nerve agents: design, construction and characterization. Chemico-biological interactions 119-120, 413-418.

Camps, J., Marsillach, J., and Joven, J. (2009). Pharmacological and lifestyle factors modulating serum paraoxonase-1 activity. Mini Rev Med Chem 9, 911-920.

Cannard, K. (2006). The acute treatment of nerve agent exposure. J Neurol Sci 249, 86-94.

diTargiani, R. C., Chandrasekaran, L., Belinskaya, T., and Saxena, A. (2010). In search of a catalytic bioscavenger for the prophylaxis of nerve agent toxicity. Chemico-biological interactions 187, 349-354.

Doctor, B. P., and Saxena, A. (2005). Bioscavengers for the protection of humans against organophosphate toxicity. Chem Biol Interact 157-158, 167-171.

Draganov, D. I. (2010). Lactonases with organophosphatase activity: structural and evolutionary perspectives. Chemico-biological interactions 187, 370-372.

Dunn, M. A., and Sidell, F. R. (1989). Progress in medical defense against nerve agents. Jama 262, 649-652.

Field, S. F., and Matz, M. V. (2010). Retracing evolution of red fluorescence in GFP-like proteins from Faviina corals. Molecular biology and evolution 27, 225-233.

Gaidukov, L., and Tawfik, D. S. (2005). High affinity, stability, and lactonase activity of serum paraoxonase PON1 anchored on HDL with ApoA-I. Biochemistry 44, 11843-11854.

Gupta, R. D., Goldsmith, M., Ashani, Y., Simo, Y., Mullokandov, G., Bar, H., Ben-David, M., Leader, H., Margalit, R., Silman, I., et al. (2011). Directed evolution of hydrolases for prevention of G-type nerve agent intoxication. Nat Chem Biol 7, 120-125.

Harel, M., Aharoni, A., Gaidukov, L., Brumshtein, B., Khersonsky, O., Meged, R., Dvir, H., Ravelli, R. B., McCarthy, A., Toker, L., et al. (2004). Structure and evolution of the serum paraoxonase family of detoxifying and anti-atherosclerotic enzymes. Nat Struct Mol Biol 11, 412-419.

Hemmert, A. C., Otto, T. C., Chica, R. A., Wierdl, M., Edwards, J. S., Lewis, S. L., Edwards, C. C., Tsurkan, L., Cadieux, C. L., Kasten, S. A., et al. (2011). Nerve agent hydrolysis activity designed into a human drug metabolism enzyme. PLoS One 6, e17441.

Herman, A., and Tawfik, D. S. (2007). Incorporating Synthetic Oligonucleotides via Gene Reassembly (ISOR): a versatile tool for generating targeted libraries. Protein Eng Des Sel 20, 219-226.

Katsila, T., Siskos, A. P., and Tamvakopoulos, C. (2011). Peptide and protein drugs: The study of their metabolism and catabolism by mass spectrometry. Mass Spectrom Rev.

Khersonsky, O., and Tawfik, D. S. (2006). The histidine 115-histidine 134 dyad mediates the lactonase activity of mammalian serum paraoxonases. J Biol Chem 281, 7649-7656.

Khersonsky, O., and Tawfik, D. S. (2005). Structure-reactivity studies of serum paraoxonase PON1 suggest that its native activity is lactonase. Biochemistry 44, 6371-6382.

Lenz, D. E., Yeung, D., Smith, J. R., Sweeney, R. E., Lumley, L. A., and Cerasoli, D. M. (2007). Stoichiometric and catalytic scavengers as protection against nerve agent toxicity: a mini review. Toxicology 233, 31-39.

Lin, J. H. (2009). Pharmacokinetics of biotech drugs: peptides, proteins and monoclonal antibodies. Curr Drug Metab 10, 661-691.

Mee-Hie Cho, C., Mulchandani, A., and Chen, W. (2006). Functional analysis of organophosphorus hydrolase variants with high degradation activity towards organophosphate pesticides. Protein Eng Des Sel 19, 99-105.

Melzer, M., Chen, J. C., Heidenreich, A., Gab, J., Koller, M., Kehe, K., and Blum, M. M. (2009). Reversed enantioselectivity of diisopropyl fluorophosphatase against organophosphorus nerve agents by rational design. J Am Chem Soc 131, 17226-17232.

Newmark, J. (2007). Nerve agents. Neurologist 13, 20-32.

Patel, N., Krishnan, S., Offman, M. N., Krol, M., Moss, C. X., Leighton, C., van Delft, F. W., Holland, M., Liu, J., Alexander, S., et al. (2009). A dyad of lymphoblastic lysosomal cysteine proteases degrades the antileukemic drug L-asparaginase. The Journal of clinical investigation 119, 1964-1973.

Reetz, M. T., Wilensek, S., Zha, D., and Jaeger, K. E. (2001). Directed Evolution of an Enantioselective Enzyme through Combinatorial Multiple-Cassette Mutagenesis. Angew Chem Int Ed Engl 40, 3589-3591.

Romano, James A., Lukey, Brian J., and Salem, Harry. (2008). Chemical warfare agents: chemistry, pharmacology, toxicology, and therapeutics. xxv, 723 p.

Romero, P. A., and Arnold, F. H. (2009). Exploring protein fitness landscapes by directed evolution. Nat Rev Mol Cell Biol 10, 866-876.

Seo, D., and Goldschmidt-Clermont, P. (2009). The paraoxonase gene family and atherosclerosis. Curr Atheroscler Rep 11, 182-187.

Sorenson, R. C., Primo-Parmo, S. L., Kuo, C. L., Adkins, S., Lockridge, O., and La Du, B. N. (1995). Reconsideration of the catalytic center and mechanism of mammalian paraoxonase/arylesterase. Proceedings of the National Academy of Sciences of the United States of America 92, 7187-7191.

Straub, C. S., Ives, A. R., and Gratton, C. (2011). Evidence for a trade-off between host-range breadth and host-use efficiency in aphid parasitoids. Am Nat 177, 389-395.

Tavori, H., Aviram, M., Khatib, S., Musa, R., Mannheim, D., Karmeli, R., and Vaya, J. (2011). Human carotid lesion linoleic acid hydroperoxide inhibits paraoxonase 1 (PON1) activity via reaction with PON1 free sulfhydryl cysteine 284. Free radical biology & medicine 50, 148-156.

Theriot, C. M., and Grunden, A. M. (2011). Hydrolysis of organophosphorus compounds by microbial enzymes. Appl Microbiol Biotechnol 89, 35-43.

Tsai, P. C., Bigley, A., Li, Y., Ghanem, E., Cadieux, C. L., Kasten, S. A., Reeves, T. E., Cerasoli, D. M., and Raushel, F. M. (2010). Stereoselective hydrolysis of organophosphate nerve agents by the bacterial phosphotriesterase. Biochemistry 49, 7978-7987.

What is claimed is:

1. An isolated polypeptide comprising an amino acid sequence of a variant serum paraoxonase (PON1) selected from the group consisting of SEQ ID NO: 2, 129, 140, 141 and 142, said isolated polypeptide having hydrolase catalytic efficiency of $k_{cat}/k_M \approx 10^6 \text{-} 5 \cdot 10^7\ M^{-1}min^{-1}$ for a G-type organophosphate.

2. The isolated polypeptide of claim 1 being expressible in bacteria.

3. An isolated synthetic complimentary DNA (cDNA) polynucleotide comprising a nucleic acid sequence encoding the polypeptide of claim 1.

4. A pharmaceutical composition comprising as an active ingredient the isolated polypeptide of claim 1 and a pharmaceutically acceptable carrier.

5. A nucleic acid construct comprising the isolated synthetic cDNA of claim 3 and a cis-regulatory element driving expression of said polynucleotide.

6. A method of treating an organophosphate exposure associated damage in a subject, comprising administering to the subject a therapeutically effective amount of the isolated polypeptide of claim 1.

7. An article of manufacture for treating or preventing organophosphate exposure-associated damage, the article of manufacture comprising the isolated polypeptide of claim 1 immobilized on to a solid support.

8. The article of manufacture of claim 7, wherein said solid support is for topical administration.

9. The article of manufacture of claim 8, wherein said solid support for topical administration is selected from the group consisting of a sponge, a wipe and a fabric.

10. The article of manufacture of claim 7, wherein said solid support is selected from the group consisting of a filter, a fabric and a lining.

11. A method of detoxifying a surface, the method comprising contacting the surface with the isolated polypeptide of claim 1, thereby detoxifying the surface.

12. The isolated polypeptide of claim 1 comprising the amino acid sequence of SEQ ID NO: 140.

13. The isolated polypeptide of claim 1, comprising SEQ ID NO: 129.

14. The isolated polypeptide of claim 1, comprising SEQ ID NO: 141.

15. The isolated polypeptide of claim 1, comprising SEQ ID NO: 142.

16. The isolated polypeptide of claim 1, comprising SEQ ID NO: 2.

* * * * *

SEQUENCE LISTING

```
<160> NUMBER OF SEQ ID NOS: 142

<210> SEQ ID NO 1
<211> LENGTH: 355
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 1

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

-continued

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu
        355


<210> SEQ ID NO 2
<211> LENGTH: 366
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 2

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365


<210> SEQ ID NO 3
<211> LENGTH: 366
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 3

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

-continued

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Leu Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Leu Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365
```

<210> SEQ ID NO 4
<211> LENGTH: 366
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 4

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Thr Phe
            100                 105                 110

Asn Pro Trp Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu Pro Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365


<210> SEQ ID NO 5
<211> LENGTH: 366
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 5

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Val Lys Phe Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Leu Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Phe His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365


<210> SEQ ID NO 6
<211> LENGTH: 366
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 6

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

-continued

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Val Lys Phe Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Leu Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365


<210> SEQ ID NO 7
<211> LENGTH: 366
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 7

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Val Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365


<210> SEQ ID NO 8
<211> LENGTH: 366
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 8

Met Ala Lys Leu Thr Ala Leu Thr Leu Ser Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Ser Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Arg Thr Leu
                245                 250                 255

Thr Pro Met Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365
```

<210> SEQ ID NO 9
<211> LENGTH: 366
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 9

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365


<210> SEQ ID NO 10
<211> LENGTH: 366
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 10

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Leu Gly Ile Ser Thr Phe Thr Asp Glu Asp Asn Thr Val Tyr
        115                 120                 125

Leu Leu Val Val Asn Asn Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Leu His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365
```

<210> SEQ ID NO 11
<211> LENGTH: 366
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 11

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

-continued

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365


<210> SEQ ID NO 12
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 12

Met Ala Lys Leu Thr Glu Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Glu Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Ser Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

<210> SEQ ID NO 13
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 13

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

-continued

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Cys Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 14
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 14

Met Ala Lys Pro Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

Glu Val Thr Pro Val Glu Leu Pro Asn Cys Asn Leu Val Lys Gly Val
35 40 45

Asp Asn Gly Ser Glu Asp Leu Glu Ile Leu Pro Asn Gly Leu Ala Phe
50 55 60

Ile Ser Ser Gly Leu Lys Tyr Pro Gly Ile Met Ser Phe Asp Pro Asp
65 70 75 80

Lys Ser Gly Lys Ile Leu Leu Met Asp Leu Asn Glu Glu Asp Pro Val
85 90 95

Ala Leu Glu Leu Gly Ile Thr Gly Asn Thr Leu Asp Ile Ser Ser Phe
100 105 110

Asn Pro Trp Gly Ile Ser Thr Phe Thr Asp Glu Asp Asn Thr Val Tyr
115 120 125

Leu Leu Val Val Asn His Ala Asp Ser Ser Ser Thr Val Glu Val Phe
130 135 140

Lys Phe Gln Glu Glu Glu Lys Ser Leu Leu His Leu Lys Thr Ile Arg
145 150 155 160

His Lys Leu Leu Pro Ser Val Asn Asp Ile Val Ala Val Gly Pro Glu
165 170 175

His Phe Tyr Ala Thr Asn Asp His Tyr Phe Ala Asp Pro Tyr Leu Lys
180 185 190

Ser Trp Glu Val His Leu Gly Leu Ala Trp Ser Phe Val Thr Tyr Tyr
195 200 205

Ser Pro Asn Asp Val Arg Val Val Ala Glu Gly Phe Asp Ser Ala Asn
210 215 220

Gly Ile Asn Ile Ser Pro Asp Gly Lys Tyr Val Tyr Ile Ala Glu Leu
225 230 235 240

Leu Ala His Lys Ile His Val Tyr Glu Lys His Ala Asn Trp Thr Leu
245 250 255

Thr Pro Leu Lys Ser Leu Asp Phe Asp Thr Leu Val Asp Asn Ile Ser
260 265 270

Val Asp Pro Val Thr Gly Asp Leu Trp Val Gly Cys His Pro Asn Gly
275 280 285

Met Arg Ile Phe Tyr Tyr Asp Pro Lys Asn Pro Pro Gly Ser Glu Val
290 295 300

Leu Arg Ile Gln Asp Ile Leu Ser Glu Glu Pro Lys Val Thr Val Val
305 310 315 320

Tyr Ala Glu Asn Gly Thr Val Leu Gln Gly Ser Thr Val Ala Ala Val
325 330 335

Tyr Lys Gly Lys Leu Leu Ile Gly Thr Val Phe His Lys Ala Leu Tyr
340 345 350

Cys Glu Leu His His His His His His His His
355 360

<210> SEQ ID NO 15
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 15

Met Ala Lys Leu Thr Ala Leu Thr Leu Leu Gly Leu Gly Leu Ala Leu
1 5 10 15

Phe Asp Gly Gln Lys Ser Ser Phe Gln Thr Arg Phe Asn Val His Arg
20 25 30

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn Thr Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Leu Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 16
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 16

Met Ala Lys Leu Thr Thr Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Ala Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Ala Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asn Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Ile Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 17
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 17

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Ala Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu His His His His His His His His
        355                 360


<210> SEQ ID NO 18
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 18

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Ser
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Ala Thr Gly Asp Leu Trp Val Gly Cys Arg Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 19
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 19

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Thr Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Pro Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu His His His His His His His His
        355                 360
```

<210> SEQ ID NO 20
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 20

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Glu Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 21
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 21

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Ser
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys Arg Pro Asn Gly
        275                 280                 285

Met Arg Ile Phe Ser Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

<210> SEQ ID NO 22
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 22

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asp Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Ser
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys Arg Pro Asn Gly
        275                 280                 285

Met Arg Ile Phe Ser Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

<210> SEQ ID NO 23
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 23

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Thr Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys Arg Pro Asn Gly
        275                 280                 285

Met Arg Ile Phe Ser Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 24
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 24

Met Ala Lys Leu Thr Ala Leu Thr Leu Ser Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Ala Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

```
<210> SEQ ID NO 25
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 25

Met Ala Lys Leu Thr Ala Leu Thr Leu Ser Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Ala Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 26
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 26

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Ala Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Ala Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Ile Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

<210> SEQ ID NO 27
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 27

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asp Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Pro Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Ser
225                 230                 235                 240

Leu Ala Arg Lys Ile His Val Tyr Glu Lys His Ala Asn Trp Thr Leu
                245                 250                 255

Thr Pro Leu Lys Ser Leu Asp Leu Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asp Gly Thr Val Leu Gln Gly Ser Ala Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 28
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 28

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Val His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

<210> SEQ ID NO 29
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 29

```
Met Ala Lys Leu Thr Ala Leu Thr Leu Leu Gly Leu Gly Leu Ala Leu
1               5                   10                  15

Ser Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu His His His His His His His His
        355                 360


<210> SEQ ID NO 30
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 30

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Leu Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

<210> SEQ ID NO 31
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 31

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Ser Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Ala Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 32
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 32

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu His His His His His His His His
        355                 360


<210> SEQ ID NO 33
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 33

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Ile His Lys Ala Leu Tyr
            340                 345                 350

Cys Glu Leu His His His His His His His His
        355                 360


<210> SEQ ID NO 34
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 34

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Leu Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu His His His His His His His His
        355                 360


<210> SEQ ID NO 35
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 35

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Ile Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu His His His His His His His His
        355                 360
```

<210> SEQ ID NO 36
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 36

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Leu Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu His His His His His His His His
        355                 360
```

<210> SEQ ID NO 37
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 37

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Pro Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Met Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu His His His His His His His His
        355                 360
```

<210> SEQ ID NO 38
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 38

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

-continued

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu His His His His His His His His
        355                 360


<210> SEQ ID NO 39
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 39

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

<210> SEQ ID NO 40
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 40

```
Met Ala Lys Leu Thr Ala Leu Thr Leu Ser Gly Leu Gly Leu Ala Leu
1               5                   10                  15

Phe Asp Gly Gln Lys Ser Ser Phe Gln Thr Arg Tyr Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 41
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 41

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Val Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

<210> SEQ ID NO 42
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 42

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Ala Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Ala Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Val His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Ile Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 43
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 43

Met Ala Lys Leu Thr Ala Leu Thr Leu Ser Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Ser Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Ala Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 44
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 44

Met Ala Lys Leu Thr Ala Leu Thr Leu Ser Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Ala Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

<210> SEQ ID NO 45
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 45

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asn Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu His His His His His His His His
        355                 360


<210> SEQ ID NO 46
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 46

Met Ala Lys Leu Thr Ala Leu Thr Leu Ser Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Ile Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu His His His His His His His His
        355                 360
```

<210> SEQ ID NO 47
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 47

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Ser Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Ala Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Ala Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

<210> SEQ ID NO 48
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 48

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

Glu Val Thr Pro Val Glu Leu Pro Asn Cys Asn Leu Val Lys Gly Val
35 40 45

Asp Asn Gly Ser Glu Asp Leu Glu Ile Leu Pro Asn Gly Leu Ala Phe
50 55 60

Ile Ser Ser Gly Leu Lys Tyr Pro Gly Ile Met Ser Phe Asp Pro Asp
65 70 75 80

Lys Ser Gly Lys Ile Leu Leu Met Asp Leu Asn Glu Glu Asp Pro Val
85 90 95

Ala Leu Glu Leu Gly Ile Thr Gly Asn Thr Leu Asp Ile Ser Ser Phe
100 105 110

Asn Pro Trp Gly Ile Ser Thr Phe Thr Asp Glu Asp Asn Thr Val Tyr
115 120 125

Leu Leu Val Val Asn His Ala Asp Ser Ser Ser Thr Val Glu Val Phe
130 135 140

Lys Phe Gln Glu Glu Glu Lys Ser Leu Leu His Leu Lys Thr Ile Arg
145 150 155 160

His Lys Leu Leu Pro Ser Val Asn Asp Ile Val Ala Val Gly Pro Glu
165 170 175

His Phe Tyr Ala Thr Asn Asp His Tyr Phe Ala Asp Pro Tyr Leu Lys
180 185 190

Ser Trp Glu Met His Leu Gly Leu Ala Trp Ser Phe Val Thr Tyr Tyr
195 200 205

Ser Pro Asn Asp Val Arg Val Val Ala Glu Gly Phe Asp Ser Ala Asn
210 215 220

Gly Ile Asn Ile Ser Pro Asp Gly Lys Tyr Val Tyr Val Ala Glu Leu
225 230 235 240

Leu Ala His Lys Ile His Val Tyr Glu Lys His Ala Asn Trp Thr Leu
245 250 255

Thr Pro Leu Lys Ser Phe Asp Phe Asp Thr Leu Val Asp Asn Ile Ser
260 265 270

Val Asp Pro Val Thr Gly Asp Leu Trp Val Gly Cys His Pro Asn Gly
275 280 285

Met Arg Ile Phe Tyr Tyr Asp Pro Lys Asn Pro Pro Gly Ser Glu Val
290 295 300

Leu Arg Ile Gln Asp Ile Leu Ser Glu Glu Pro Lys Val Thr Val Val
305 310 315 320

Tyr Ala Glu Asn Gly Thr Val Leu Gln Gly Ser Thr Val Ala Ala Val
325 330 335

Tyr Lys Gly Lys Leu Leu Ile Gly Thr Val Phe His Lys Ala Leu Tyr
340 345 350

Cys Glu Leu His His His His His His His His
355 360

<210> SEQ ID NO 49
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 49

Met Ala Lys Leu Thr Ala Leu Thr Leu Leu Gly Leu Gly Leu Ala Leu
1 5 10 15

Phe Asp Gly Gln Lys Ser Ser Phe Gln Thr Arg Phe Asn Val His Arg
20 25 30

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Ala Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Ala Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 50
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 50

Met Ala Lys Leu Thr Ala Leu Thr Leu Ser Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn Lys Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360


<210> SEQ ID NO 51
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 51

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

<210> SEQ ID NO 52
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 52

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu His His His His His His His His
        355                 360


<210> SEQ ID NO 53
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 53

Met Ala Lys Leu Thr Ala Leu Thr Leu Leu Gly Leu Gly Met Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Thr Phe
            100                 105                 110

Asn Pro Trp Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

<210> SEQ ID NO 54
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 54

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30
```

```
Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu His His His His His His His His
        355                 360
```

<210> SEQ ID NO 55
<211> LENGTH: 1065
<212> TYPE: DNA
<213> ORGANISM: Artificial sequence
<220> FEATURE:
<223> OTHER INFORMATION: Serum paraoxonase (PON1) Variant coding
      sequence

<400> SEQUENCE: 55

```
atggcgaaac tgaccgcgct gaccctgctg ggcctgggcc tggcgctgtt tgatggccag      60

aaaagcagct ttcagacccg ctttaacgtg catcgcgaag tgaccccggt ggaactgccg     120

aactgcaacc tggtgaaagg cgtggataac ggcagcgaag atctggaaat tctgccgaac     180
```

```
ggcctggcgt ttattagcag cggcctgaaa tatccgggca ttatgagctt tgatccggat    240
aaaagcggca aaattctgct gatggatctg aacgaagaag atccggtggt gctggaactg    300
ggcattaccg gcaacaccct ggatattagc agctttaacc cgcatggcat tagcaccttt    360
accgatgaag ataacaccgt gtatctgctg gtggtgaacc atccggatag cagcagcacc    420
gtggaagtgt ttaaatttca ggaagaagaa aaaagcctgc tgcatctgaa aaccattcgc    480
cataaactgc tgccgagcgt gaacgatatt gtggcggtgg gcccggaaca tttttatgcg    540
accaacgatc attattttgc ggatccgtat ctgaaaagct gggaaatgca tctgggcctg    600
gcgtggagct ttgtgaccta ttatagcccg aacgatgtgc gcgtggtggc ggaaggcttt    660
gattttgcga acggcattaa cattagcccg gatggcaaat atgtgtatat tgcggaactg    720
ctggcgcata aaattcatgt gtatgaaaaa catgcgaact ggaccctgac cccgctgaaa    780
agcctggatt ttgataccct ggtggataac attagcgtgg atccggtgac cggcgatctg    840
tgggtgggct gccatccgaa cggcatgcgc atttttttatt atgatccgaa aaacccgccg    900
ggcagcgaag tgctgcgcat tcaggatatt ctgagcgaag aaccgaaagt gaccgtggtg    960
tatgcggaaa acggcaccgt gctgcagggc agcaccgtgg cggcggtgta taaaggcaaa   1020
ctgctgattg gcaccgtgtt tcataaagcg ctgtattgcg aactg                   1065
```

<210> SEQ ID NO 56
<211> LENGTH: 1098
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 56

```
atggcgaaac tgaccgcgct gaccctgctg ggcctgggcc tggcgctgtt tgatggccag     60
aaaagcagct ttcagacccg ctttaacgtg catcgcgaag tgaccccggt ggaactgccg    120
aactgcaacc tggtgaaagg cgtggataac ggcagcgaag atctggaaat tctgccgaac    180
ggcctggcgt ttattagcag cggcggcaaa tatccgggca ttatgagctt tgatccggat    240
aaaagcggca aaattctgct gatggatctg aacgaagaag atccggtggt gctggaactg    300
ggcattaccg gcaacaccct ggatattagc agctttaacc cgtggggcat tagcaccttt    360
accgatgaag ataacaccgt gtatctgctg gtggtgaacc gcccggatag cagcagcacc    420
gtggaagtgt ttaaatttca ggaagaagaa aaaagcctgc tgcatctgaa aaccattcgc    480
cataaactgc tgccgagcgt gaacgatatt gtggcggtgg gcccggaaca tttttatgcg    540
accaacgatc attattttgc ggatccgtat ctgaaaagct gggaaatgca tctgggcctg    600
gcgtggagct ttgtgaccta ttatagcccg aacgatgtgc gcgtggtggc ggaaggcttt    660
gatagcgcga acggcattaa cattagcccg gatggcaaat atgtgtatat tgcggaactg    720
ctggcgcata aaattcatgt gtatgaaaaa catgcgaact ggaccctgac cccgctgaaa    780
agcctggatt ttgataccct ggtggataac attagcgtgg atccggtgac cggcgatctg    840
tgggtgggct gccatccgaa cggcatgcgc atttttttatt atgatccgaa aaacccgccg    900
ggcagcgaag tgctgcgcat tcaggatatt ctgagcgaag aaccgaaagt gaccgtggtg    960
tatgcggaaa acggcaccgt gctgcagggc agcagcgtgg cggcggtgta taaaggcaaa   1020
ctgctgattg gcaccgtgtt tcataaagcg ctgtattgcg aactggcggc ggcgctggaa   1080
catcatcatc atcatcat                                                 1098
```

<210> SEQ ID NO 57
<211> LENGTH: 1098
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 57

```
atggcgaaac tgaccgcgct gaccctgctg ggcctgggcc tggcgctgtt tgatggccag      60

aaaagcagct ttcagacccg ctttaacgtg catcgcgaag tgaccccggt ggaactgccg     120

aactgcaacc tggtgaaagg cgtggataac ggcagcgaag atctggaaat tctgccgaac     180

ggcctggcgt ttattagcag cggcgtgaaa tatccgggca ttatgagctt tgatccggat     240

aaaagcggca aaattctgct gatggatctg aacgaagaag atccggtggt gctggaactg     300

ggcattaccg gcaacaccct ggatattagc agctttaacc cgctgggcat tagcaccttt     360

accgatgaag ataacaccgt gtatctgctg gtggtgaacc gcccggatag cagcagcacc     420

gtggaagtgt ttaaatttca ggaagaagaa aaaagcctgc tgcatctgaa aaccattcgc     480

cataaactgc tgccgagcgt gaacgatatt gtggcggtgg gcccggaaca tttttatgcg     540

accaacgatc attattttgc ggatccgtat ctgaaaagct gggaaatgca tctgggcctg     600

gcgtggagct ttgtgaccta ttatagcccg aacgatgtgc gcgtggtggc ggaaggcttt     660

gatagcgcga acggcattaa cattagcccg gatggcaaat atgtgtatat tgcggaactg     720

ctggcgcata aaattcatgt gtatgaaaaa catgcgaact ggaccctgac cccgctgaaa     780

agcctggatt ttgataccct ggtggataac attagcgtgg atccggtgac cggcgatctg     840

tgggtgggct gccatccgaa cggcatgcgc attctgtatt atgatccgaa aaacccgccg     900

ggcagcgaag tgctgcgcat tcaggatatt ctgagcgaag aaccgaaagt gaccgtggtg     960

tatgcggaaa acggcaccgt gctgcagggc agcagcgtgg cggcggtgta taaaggcaaa    1020

ctgctgattg gcaccgtgtt tcataaagcg ctgtattgcg aactggcggc ggcgctggaa    1080

catcatcatc atcatcat                                                  1098
```

<210> SEQ ID NO 58
<211> LENGTH: 1098
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 58

```
atggcgaaac tgaccgcgct gaccctgctg ggcctgggcc tggcgctgtt tgatggccag      60

aaaagcagct ttcagacccg ctttaacgtg catcgcgaag tgaccccggt ggaactgccg     120

aactgcaacc tggtgaaagg cgtggataac ggcagcgaag atctggaaat tctgccgaac     180

ggcctggcgt ttattagcag cggcggcaaa tatccgggca ttatgagctt tgatccggat     240

aaaagcggca aaattctgct gatggatctg aacgaagaag atccggtggt gctggaactg     300

ggcattaccg gcaacaccct ggatattagc acctttaacc cgtggggcat tagcaccttt     360

accgatgaag ataacaccgt gtatctgctg gtggtgaacc gcccggatag cagcagcacc     420

gtggaagtgt ttaaatttca ggaagaagaa aaaagcctgc tgccgctgaa aaccattcgc     480

cataaactgc tgccgagcgt gaacgatatt gtggcggtgg gcccggaaca tttttatgcg     540

accaacgatc attattttgc ggatccgtat ctgaaaagct gggaaatgca tctgggcctg     600
```

-continued

```
gcgtggagct ttgtgaccta ttatagcccg aacgatgtgc gcgtggtggc ggaaggcttt    660

gatagcgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc attttttatt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcagcgtgg cggcggtgta taaaggcaaa   1020

ctgctgattg gcaccgtgtt tcataaagcg ctgtattgcg aactggcggc ggcgctggaa   1080

catcatcatc atcatcat                                                  1098
```

<210> SEQ ID NO 59
<211> LENGTH: 1098
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 59

```
atggcgaaac tgaccgcgct gaccctgctg ggcctgggcc tggcgctgtt tgatggccag     60

aaaagcagct ttcagacccg ctttaacgtg catcgcgaag tgaccccggt ggaactgccg    120

aactgcaacc tggtgaaagg cgtggataac ggcagcgaag atctggaaat tctgccgaac    180

ggcctggcgt ttattagcag cggcgtgaaa tttccgggca ttatgagctt tgatccggat    240

aaaagcggca aaattctgct gatggatctg aacgaagaag atccggtggt gctggaactg    300

ggcattaccg gcaacaccct ggatattagc agctttaacc cgctgggcat tagcaccttt    360

accgatgaag ataacaccgt gtatctgctg gtggtgaacc gcccggatag cagcagcacc    420

gtggaagtgt ttaaatttca ggaagaagaa aaaagcctgc tgcatctgaa aaccattcgc    480

cataaactgc tgccgagcgt gaacgatatt gtggcggtgg gcccggaaca tttttatgcg    540

accaacgatc attattttgc ggatccgtat ctgaaaagct gggaatttca tctgggcctg    600

gcgtggagct ttgtgaccta ttatagcccg aacgatgtgc gcgtggtggc ggaaggcttt    660

gatagcgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc attttttatt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcagcgtgg cggcggtgta taaaggcaaa   1020

ctgctgattg gcaccgtgtt tcataaagcg ctgtattgcg aactggcggc ggcgctggaa   1080

catcatcatc atcatcat                                                  1098
```

<210> SEQ ID NO 60
<211> LENGTH: 1098
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 60

```
atggcgaaac tgaccgcgct gaccctgctg ggcctgggcc tggcgctgtt tgatggccag     60
```

```
aaaagcagct ttcagacccg ctttaacgtg catcgcgaag tgaccccggt ggaactgccg    120

aactgcaacc tggtgaaagg cgtggataac ggcagcgaag atctggaaat tctgccgaac    180

ggcctggcgt ttattagcag cggcgtgaaa tttccgggca ttatgagctt tgatccggat    240

aaaagcggca aaattctgct gatggatctg aacgaagaag atccggtggt gctggaactg    300

ggcattaccg gcaacaccct ggatattagc agctttaacc cgctgggcat tagcaccttt    360

accgatgaag ataacaccgt gtatctgctg gtggtgaacc gcccggatag cagcagcacc    420

gtggaagtgt ttaaatttca ggaagaagaa aaaagcctgc tgcatctgaa aaccattcgc    480

cataaactgc tgccgagcgt gaacgatatt gtggcggtgg gcccggaaca tttttatgcg    540

accaacgatc attattttgc ggatccgtat ctgaaaagct gggaaatgca tctgggcctg    600

gcgtggagct ttgtgaccta ttatagcccg aacgatgtgc gcgtggtggc ggaaggcttt    660

gatagcgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc atttttttatt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcagcgtgg cggcggtgta taaaggcaaa   1020

ctgctgattg gcaccgtgtt tcataaagcg ctgtattgcg aactggcggc ggcgctggaa   1080

catcatcatc atcatcat                                                  1098
```

<210> SEQ ID NO 61
<211> LENGTH: 1098
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 61

```
atggcgaaac tgaccgcgct gaccctgctg ggcctgggcc tggcgctgtt tgatggccag     60

aaaagcagct ttcagacccg ctttaacgtg catcgcgaag tgaccccggt ggaactgccg    120

aactgcaacc tggtgaaagg cgtggataac ggcagcgaag atctggaaat tctgccgaac    180

ggcctggcgt ttattagcag cggcgtgaaa tatccgggca ttatgagctt tgatccggat    240

aaaagcggca aaattctgct gatggatctg aacgaagaag atccggtggt gctggaactg    300

ggcattaccg gcaacaccct ggatattagc agctttaacc cggtgggcat tagcaccttt    360

accgatgaag ataacaccgt gtatctgctg gtggtgaacc gcccggatag cagcagcacc    420

gtggaagtgt ttaaatttca ggaagaagaa aaaagcctgc tgcatctgaa aaccattcgc    480

cataaactgc tgccgagcgt gaacgatatt gtggcggtgg gcccggaaca tttttatgcg    540

accaacgatc attattttgc ggatccgtat ctgaaaagct gggaaatgca tctgggcctg    600

gcgtggagct ttgtgaccta ttatagcccg aacgatgtgc gcgtggtggc ggaaggcttt    660

gatagcgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc atttttttatt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcagcgtgg cggcggtgta taaaggcaaa   1020
```

ctgctgattg gcaccgtgtt tcataaagcg ctgtattgcg aactggcggc ggcgctggaa 1080
catcatcatc atcatcat 1098

<210> SEQ ID NO 62
<211> LENGTH: 1098
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 62
atggcgaaac tgaccgcgct gaccctgagc ggcctgggcc tggcgctgtt tgatggccag 60
aaaagcagct ttcagacccg ctttaacgtg catcgcgaag tgagcccggt ggaactgccg 120
aactgcaacc tggtgaaagg cgtggataac ggcagcgaag atctggaaat tctgccgaac 180
ggcctggcgt ttattagcag cggcggcaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc gcccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gatagcgcga acggcattaa cattagcccg gatggcaaat atgtgtatat tgcggaactg 720
ctggcgcata aaattcatgt gtatgaaaaa catgcgaacc gcaccctgac cccgatgaaa 780
agcctggatt ttgataccct ggtggataac attagcgtgg atccggtgac cggcgatctg 840
tgggtgggct gccatccgaa cggcatgcgc atttttattt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcagcgtgg cggcggtgta taaaggcaaa 1020
ctgctgattg gcaccgtgtt tcataaagcg ctgtattgcg aactggcggc ggcgctggaa 1080
catcatcatc atcatcat 1098

<210> SEQ ID NO 63
<211> LENGTH: 1098
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 63
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcgtgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc gcccggatag cagcagcacc 420
gtggaagtgt ttaaatttca ggaagaagaa aaaagcctgc tgcatctgaa aaccattcgc 480

```
cataaactgc tgccgagcgt gaacgatatt gtggcggtgg gcccggaaca tttttatgcg    540

accaacgatc attattttgc ggatccgtat ctgaaaagct gggaaatgca tctgggcctg    600

gcgtggagct ttgtgaccta ttatagcccg aacgatgtgc gcgtggtggc ggaaggcttt    660

gatagcgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc atttttattt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcagcgtgg cggcggtgta taaaggcaaa   1020

ctgctgattg gcaccgtgtt tcataaagcg ctgtattgcg aactggcggc ggcgctggaa   1080

catcatcatc atcatcat                                                 1098
```

<210> SEQ ID NO 64
<211> LENGTH: 1098
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 64

```
atggcgaaac tgaccgcgct gaccctgctg ggcctgggcc tggcgctgtt tgatggccag     60

aaaagcagct ttcagacccg ctttaacgtg catcgcgaag tgaccccggt ggaactgccg    120

aactgcaacc tggtgaaagg cgtggataac ggcagcgaag atctggaaat tctgccgaac    180

ggcctggcgt ttattagcag cggcgtgaaa tatccgggca ttatgagctt tgatccggat    240

aaaagcggca aaattctgct gatggatctg aacgaagaag atccggtggt gctggaactg    300

ggcattaccg gcaacaccct ggatattagc agctttaacc cgctgggcat tagcaccttt    360

accgatgaag ataacaccgt gtatctgctg gtggtgaaca acccggatag cagcagcacc    420

gtggaagtgt ttaaatttca ggaagaagaa aaaagcctgc tgcatctgaa aaccattcgc    480

cataaactgc tgccgagcgt gaacgatatt gtggcggtgg gcccggaaca tttttatgcg    540

accaacgatc attattttgc ggatccgtat ctgaaaagct gggaactgca tctgggcctg    600

gcgtggagct ttgtgaccta ttatagcccg aacgatgtgc gcgtggtggc ggaaggcttt    660

gatagcgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc atttttattt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcagcgtgg cggcggtgta taaaggcaaa   1020

ctgctgattg gcaccgtgtt tcataaagcg ctgtattgcg aactggcggc ggcgctggaa   1080

catcatcatc atcatcat                                                 1098
```

<210> SEQ ID NO 65
<211> LENGTH: 1098
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 65
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgcatggcat tagcaccttt 360
accgatgaag ataacaccgt gtatctgctg gtggtgaacc atccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gattttgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc attttttatt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgtgtt tcataaagcg ctgtattgcg aactggcggc ggcgctggaa 1080
catcatcatc atcatcat 1098

<210> SEQ ID NO 66
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 66
atggcgaaac tgaccgaact gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcggcaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc gcccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gatagcgcga acggcattaa cattagcccg gatggcgaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840

```
tgggtgggct gccatccgaa cggcatgcgc attttttatt atgatccgaa aaacccgccg    900

ggcagcgaag tgctgcgcat tcaggatatt ctgagcgaag aaccgaaagt gaccgtggtg    960

tatgcggaaa acggcagcgt gctgcagggc agcagcgtgg cggcggtgta taaaggcaaa   1020

ctgctgattg gcaccgtgtt tcataaagcg ctgtattgcg aactgcatca tcatcatcat   1080

catcatcat                                                           1089
```

<210> SEQ ID NO 67
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 67

```
atggcgaaac tgaccgcgct gaccctgctg ggcctgggcc tggcgctgtt tgatggccag     60

aaaagcagct ttcagacccg ctttaacgtg catcgcgaag tgaccccggt ggaactgccg    120

aactgcaacc tggtgaaagg cgtggataac ggcagcgaag atctggaaat tctgccgaac    180

ggcctggcgt ttattagcag cggcggcaaa tatccgggca ttatgagctt tgatccggat    240

aaaagcggca aaattctgct gatggatctg aacgaagaag atccggtggt gctggaactg    300

ggcattaccg gcaacaccct ggatattagc agctttaacc cgtggggcat tagcaccttt    360

accgatgaag ataacaccgt gtatctgctg gtggtgaacc gcccggatag cagcagcacc    420

gtggaagtgt ttaaatttca ggaagaagaa aaaagcctgc tgcatctgaa aaccattcgc    480

cataaactgc tgccgagcgt gaacgatatt gtggcggtgg gcccggaaca tttttatgcg    540

accaacgatc attattttgc ggatccgtat ctgaaaagct gggaaatgca tctgggcctg    600

gcgtggagct ttgtgaccta ttatagcccg aacgatgtgc gcgtggtggc ggaaggcttt    660

gattgcgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc attttttatt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcaccgtgg cggcggtgta taaaggcaaa   1020

ctgctgattg gcaccgtgtt tcataaagcg ctgtattgcg aactgcatca tcatcatcat   1080

catcatcat                                                           1089
```

<210> SEQ ID NO 68
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 68

```
atggcgaaac cgaccgcgct gaccctgctg ggcctgggcc tggcgctgtt tgatggccag     60

aaaagcagct ttcagacccg ctttaacgtg catcgcgaag tgaccccggt ggaactgccg    120

aactgcaacc tggtgaaagg cgtggataac ggcagcgaag atctggaaat tctgccgaac    180

ggcctggcgt ttattagcag cggcctgaaa tatccgggca ttatgagctt tgatccggat    240

aaaagcggca aaattctgct gatggatctg aacgaagaag atccggtggc gctggaactg    300
```

```
ggcattaccg gcaacaccct ggatattagc agctttaacc cgtggggcat tagcaccttt    360

accgatgaag ataacaccgt gtatctgctg gtggtgaacc atgcggatag cagcagcacc    420

gtggaagtgt ttaaatttca ggaagaagaa aaaagcctgc tgcatctgaa aaccattcgc    480

cataaactgc tgccgagcgt gaacgatatt gtggcggtgg gcccggaaca tttttatgcg    540

accaacgatc attattttgc ggatccgtat ctgaaaagct gggaagtgca tctgggcctg    600

gcgtggagct ttgtgaccta ttatagcccg aacgatgtgc gcgtggtggc ggaaggcttt    660

gatagcgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc atttttattt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcaccgtgg cggcggtgta taaaggcaaa   1020

ctgctgattg gcaccgtgtt tcataaagcg ctgtattgcg aactgcatca tcatcatcat   1080

catcatcat                                                           1089
```

```
<210> SEQ ID NO 69
<211> LENGTH: 1089
<212> TYPE: DNA
<213> ORGANISM: Artificial sequence
<220> FEATURE:
<223> OTHER INFORMATION: Serum paraoxonase (PON1) Variant coding
      sequence

<400> SEQUENCE: 69

atggcgaaac tgaccgcgct gaccctgctg ggcctgggcc tggcgctgtt tgatggccag     60

aaaagcagct ttcagacccg ctttaacgtg catcgcgaag tgaccccggt ggaactgccg    120

aactgcaacc tggtgaaagg cgtggataac ggcagcgaag atctggaaat tctgccgaac    180

ggcctggcgt ttattagcag cggcggcaaa tatccgggca ttatgagctt tgatccggat    240

aaaagcggca aaattctgct gatggatctg aacgaagaag atccggtggt gctggaactg    300

ggcattaccg gcaacaccct ggatattagc agctttaacc cgtggggcat tagcaccttt    360

accgatgaag ataacaccgt gtatctgctg gtggtgaaca ccccggatag cagcagcacc    420

gtggaagtgt ttaaatttca ggaagaagaa aaaagcctgc tgcatctgaa aaccattcgc    480

cataaactgc tgccgagcgt gaacgatatt gtggcggtgg gcccggaaca tttttatgcg    540

accaacgatc attattttgc ggatccgtat ctgaaaagct gggaaatgca tctgggcctg    600

gcgtggagct ttgtgaccta ttatagcccg aacgatgtgc gcgtggtggc ggaaggcttt    660

gatctggcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc atttttattt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcaccgtgg cggcggtgta taaaggcaaa   1020

ctgctgattg gcaccgtgtt tcataaagcg ctgtattgcg aactgcatca tcatcatcat   1080

catcatcat                                                           1089
```

```
<210> SEQ ID NO 70
<211> LENGTH: 1089
```

<212> TYPE: DNA
<213> ORGANISM: Artificial sequence
<220> FEATURE:
<223> OTHER INFORMATION: Serum paraoxonase (PON1) Variant coding sequence

<400> SEQUENCE: 70

```
atggcgaaac tgaccaccct gaccctgctg ggcctgggcc tggcgctgtt tgatggccag     60
aaaagcagct ttcagacccg ctttaacgtg catcgcgaag tgaccccggt ggaactgccg    120
aactgcaacc tggtgaaagg cgtggataac ggcagcgaag atctggaaat tctgccgaac    180
ggcctggcgt ttattagcag cggcctgaaa tatccgggca ttatgagctt tgatccggat    240
aaaagcggca aaattctgct gatggatctg aacgaagaag atccggtggc gctggaactg    300
ggcattaccg gcaacaccct ggatattagc agctttaacc cgtggggcat tagcaccttt    360
accgatgaag ataacaccgt gtatctgctg gtggtgaacc atgcggatag cagcagcacc    420
gtggaagtgt ttaaatttca ggaagaagaa aaaagcctgc tgcatctgaa aaccattcgc    480
cataaactgc tgccgagcgt gaacgatatt gtggcggtgg gcccggaaca tttttatgcg    540
accaacgatc attattttgc ggatccgtat ctgaaaagct gggaaatgca tctgggcctg    600
gcgtggagct ttgtgaccta ttatagcccg aacaacgtgc gcgtggtggc ggaaggcttt    660
gatagcgcga acggcattaa cattagcccg gatggcaaat atgtgtatat tgcggaactg    720
ctggcgcata aaattcatgt gtatgaaaaa catgcgaact ggaccctgac cccgctgaaa    780
agcctggatt ttgataccct ggtggataac attagcgtgg atccggtgac cggcgatctg    840
tgggtgggct gccatccgaa cggcattcgc atttttattt atgatccgaa aaacccgccg    900
ggcagcgaag tgctgcgcat tcaggatatt ctgagcgaag aaccgaaagt gaccgtggtg    960
tatgcggaaa acggcaccgt gctgcagggc agcaccgtgg cggcggtgta taaaggcaaa   1020
ctgctgattg gcaccgtgtt tcataaagcg ctgtattgcg aactgcatca tcatcatcat   1080
catcatcat                                                          1089
```

<210> SEQ ID NO 71
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 71

```
atggcgaaac tgaccgcgct gaccctgctg ggcctgggcc tggcgctgtt tgatggccag     60
aaaagcagct ttcagacccg ctttaacgtg catcgcgaag tgaccccggt ggaactgccg    120
aactgcaacc tggtgaaagg cgtggataac ggcagcgaag atctggaaat tctgccgaac    180
ggcctggcgt ttattagcag cggcctgaaa tatccgggca ttatgagctt tgatccggat    240
aaaagcggca aaattctgct gatggatctg aacgaagaag atccggtggt gctggaactg    300
ggcattaccg gcaacaccct ggatattagc agctttaacc cgtggggcat tagcaccttt    360
accgatgaag ataacaccgt gtatctgctg gtggtgaacc atgcggatag cagcagcacc    420
gtggaagtgt ttaaatttca ggaagaagaa aaaagcctgc tgcatctgaa aaccattcgc    480
cataaactgc tgccgagcgt gaacgatatt gtggcggtgg gcccggaaca tttttatgcg    540
accaacgatc attattttgc ggatccgtat ctgaaaagct gggaaatgca tctgggcctg    600
gcgtggagct ttgtgaccta ttatagcccg aacgatgtgc gcgtggtggc ggaaggcttt    660
gattttgcga acggcattaa cattagcccg gatggcaaat atgtgtatat tgcggaactg    720
```

ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttattt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgcgtt tcataaagcg ctgtattgcg aactgcatca tcatcatcat 1080
catcatcat 1089

<210> SEQ ID NO 72
<211> LENGTH: 1089
<212> TYPE: DNA
<213> ORGANISM: Artificial sequence
<220> FEATURE:
<223> OTHER INFORMATION: Serum paraoxonase (PON1) Variant coding
sequence

<400> SEQUENCE: 72
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgcatggcat tagcaccttt 360
accgatgaag ataacaccgt gtatctgctg gtggtgaacc atccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gattttgcga acggcattaa cattagcccg gatggcaaat atgtgtatat tgcggaaagc 720
ctggcgcata aaattcatgt gtatgaaaaa catgcgaact ggaccctgac cccgctgaaa 780
agcctggatt ttgataccct ggtggataac attagcgtgg atccggcgac cggcgatctg 840
tgggtgggct gccgcccgaa cggcatgcgc atttttattt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcagcgtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 73
<211> LENGTH: 1089
<212> TYPE: DNA
<213> ORGANISM: Artificial sequence
<220> FEATURE:
<223> OTHER INFORMATION: Serum paraoxonase (PON1) Variant coding
sequence

<400> SEQUENCE: 73
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggataccagc agctttaacc cgtggggcat tagcaccttt 360
accgatgaag ataacaccgt gtatctgctg gtggtgaacc atccggatag cagcccgacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gattttgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttattt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgcgtt tcataaagcg ctgtattgcg aactgcatca tcatcatcat 1080
catcatcat 1089

<210> SEQ ID NO 74
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 74
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcggcaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc gcccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gatagcgcga acggcattaa cattagcccg gatggcgaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttattt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 75
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 75
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgcatggcat tagcaccttt 360
accgatgaag ataacaccgt gtatctgctg gtggtgaacc atccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gattttgcga acggcattaa cattagcccg gatggcaaat atgtgtatat tgcggaaagc 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccgcccgaa cggcatgcgc atttttagct atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 76
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 76
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
gattgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgcatggcat tagcaccttt 360
accgatgaag ataacaccgt gtatctgctg gtggtgaacc atccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540

```
accaacgatc attattttgc ggatccgtat ctgaaaagct gggaaatgca tctgggcctg    600

gcgtggagct ttgtgaccta ttatagcccg aacgatgtgc gcgtggtggc ggaaggcttt    660

gattttgcga acggcattaa cattagcccg gatggcaaat atgtgtatat tgcggaaagc    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccgcccgaa cggcatgcgc atttttagct atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcagcgtgg cggcggtgta taaaggcaaa   1020

ctgctgattg gcaccgtgtt tcataaagcg ctgtattgcg aactgcatca tcatcatcat   1080

catcatcat                                                           1089
```

```
<210> SEQ ID NO 77
<211> LENGTH: 1089
<212> TYPE: DNA
<213> ORGANISM: Artificial sequence
<220> FEATURE:
<223> OTHER INFORMATION: Serum paraoxonase (PON1) Variant coding
      sequence

<400> SEQUENCE: 77

atggcgaaac tgaccgcgct gaccctgctg ggcctgggcc tggcgctgtt tgatggccag     60

aaaagcagct ttcagacccg ctttaacgtg catcgcgaag tgaccccggt ggaactgccg    120

aactgcaacc tggtgaaagg cgtggataac ggcagcgaag atctggaaat tctgccgaac    180

ggcctggcgt ttattagcag cggcctgaaa tatccgggca ttatgagctt tgatccggat    240

aaaagcggca aaattctgct gatggatctg aacgaagaag atccggtggt gctggaactg    300

ggcattaccg gcaacaccct ggatattagc agctttaacc cgcatggcat tagcaccttt    360

accgatgaag ataacaccgt gtatctgctg gtggtgaacc atccggatag cagcagcacc    420

gtggaagtgt ttaaatttca ggaagaagaa aaaagcctgc tgcatctgaa aaccattcgc    480

cataaactgc tgccgagcgt gaacgatatt gtggcggtgg gcccggaaca tttttatgcg    540

accaacgatc attattttgc ggatccgtat ctgaaaagct gggaaatgca tctgggcctg    600

gcgtggagct ttgtgaccta ttatagcccg accgatgtgc gcgtggtggc ggaaggcttt    660

gattttgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccgcccgaa cggcatgcgc atttttagct atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcagcgtgg cggcggtgta taaaggcaaa   1020

ctgctgattg gcaccgtgtt tcataaagcg ctgtattgcg aactgcatca tcatcatcat   1080

catcatcat                                                           1089
```

```
<210> SEQ ID NO 78
<211> LENGTH: 1089
<212> TYPE: DNA
<213> ORGANISM: Artificial sequence
<220> FEATURE:
<223> OTHER INFORMATION: Serum paraoxonase (PON1) Variant coding
      sequence

<400> SEQUENCE: 78
```

-continued

```
atggcgaaac tgaccgcgct gaccctgagc ggcctgggcc tggcgctgtt tgatggccag      60

aaaagcagct ttcagacccg ctttaacgtg catcgcgaag tgaccccggt ggaactgccg     120

aactgcaacc tggtgaaagg cgtggataac ggcagcgaag atctggaaat tctgccgaac     180

ggcctggcgt ttattagcag cggcggcaaa tatccgggca ttatgagctt tgatccggat     240

aaaagcggca aaattctgct gatggatctg aacgaagaag atccggtggt gctggaactg     300

ggcattaccg gcaacaccct ggatattagc agctttaacc cgtggggcat tagcaccttt     360

accgatgaag ataacaccgt gtatctgctg gtggtgaacc atgcggatag cagcagcacc     420

gtggaagtgt ttaaatttca ggaagaagaa aaaagcctgc tgcatctgaa aaccattcgc     480

cataaactgc tgccgagcgt gaacgatatt gtggcggtgg gcccggaaca tttttatgcg     540

accaacgatc attattttgc ggatccgtat ctgaaaagct gggaaatgca tctgggcctg     600

gcgtggagct ttgtgaccta ttatagcccg aacgatgtgc gcgtggtggc ggaaggcttt     660

gatagcgcga acggcattaa cattagcccg gatggcaaat atgtgtatat tgcggaactg     720

ctggcgcata aaattcatgt gtatgaaaaa catgcgaact ggaccctgac cccgctgaaa     780

agcctggatt ttgataccct ggtggataac attagcgtgg atccggtgac cggcgatctg     840

tgggtgggct gccatccgaa cggcatgcgc atttttttatt atgatccgaa aaacccgccg     900

ggcagcgaag tgctgcgcat tcaggatatt ctgagcgaag aaccgaaagt gaccgtggtg     960

tatgcggaaa acggcaccgt gctgcagggc agcaccgtgg cggcggtgta taaaggcaaa    1020

ctgctgattg gcaccgtgtt tcataaagcg ctgtattgcg aactgcatca tcatcatcat    1080

catcatcat                                                            1089
```

<210> SEQ ID NO 79
<211> LENGTH: 1089
<212> TYPE: DNA
<213> ORGANISM: Artificial sequence
<220> FEATURE:
<223> OTHER INFORMATION: Serum paraoxonase (PON1) Variant coding
      sequence

<400> SEQUENCE: 79

```
atggcgaaac tgaccgcgct gaccctgagc ggcctgggcc tggcgctgtt tgatggccag      60

aaaagcagct ttcagacccg ctttaacgtg catcgcgaag tgaccccggt ggaactgccg     120

aactgcaacc tggtgaaagg cgtggataac ggcagcgaag atctggaaat tctgccgaac     180

ggcctggcgt ttattagcag cggcgcgaaa tatccgggca ttatgagctt tgatccggat     240

aaaagcggca aaattctgct gatggatctg aacgaagaag atccggtggt gctggaactg     300

ggcattaccg gcaacaccct ggatattagc agctttaacc cgtggggcat tagcaccttt     360

accgatgaag ataacaccgt gtatctgctg gtggtgaacc gcccggatag cagcagcacc     420

gtggaagtgt ttaaatttca ggaagaagaa aaaagcctgc tgcatctgaa aaccattcgc     480

cataaactgc tgccgagcgt gaacgatatt gtggcggtgg gcccggaaca tttttatgcg     540

accaacgatc attattttgc ggatccgtat ctgaaaagct gggaaatgca tctgggcctg     600

gcgtggagct ttgtgaccta ttatagcccg aacgatgtgc gcgtggtggc ggaaggcttt     660

gatagcgcga acggcattaa cattagcccg gatggcaaat atgtgtatat tgcggaactg     720

ctggcgcata aaattcatgt gtatgaaaaa catgcgaact ggaccctgac cccgctgaaa     780

agcctggatt ttgataccct ggtggataac attagcgtgg atccggtgac cggcgatctg     840

tgggtgggct gccatccgaa cggcatgcgc atttttttatt atgatccgaa aaacccgccg     900

ggcagcgaag tgctgcgcat tcaggatatt ctgagcgaag aaccgaaagt gaccgtggtg     960
```

```
tatgcggaaa acggcaccgt gctgcagggc agcaccgtgg cggcggtgta taaaggcaaa   1020

ctgctgattg gcaccgtgtt tcataaagcg ctgtattgcg aactgcatca tcatcatcat   1080

catcatcat                                                            1089
```

<210> SEQ ID NO 80
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 80

```
atggcgaaac tgaccgcgct gaccctgctg ggcctgggcc tggcgctgtt tgatggccag     60

aaaagcagct ttcagacccg ctttaacgtg catcgcgaag tgaccccggt ggaactgccg    120

aactgcaacc tggtgaaagg cgtggataac ggcagcgaag atctggaaat tctgccgaac    180

ggcctggcgt ttattagcag cggcctgaaa tatccgggca ttatgagctt tgatccggat    240

aaaagcggca aaattctgct gatggatctg aacgaagaag atccggtggc gctggaactg    300

ggcattaccg gcaacaccct ggatattagc agctttaacc cgtggggcat tagcaccttt    360

accgatgaag ataacaccgt gtatctgctg gtggtgaacc atgcggatag cagcagcacc    420

gtggaagtgt ttaaatttca ggaagaagaa aaaagcctgc tgcatctgaa aaccattcgc    480

cataaactgc tgccgagcgt gaacgatatt gtggcggtgg gcccggaaca tttttatgcg    540

accaacgatc attattttgc ggatccgtat ctgaaaagct gggaaatgca tctgggcctg    600

gcgtggagct ttgtgaccta ttatagcccg aacgatgtgc gcgtggtggc ggaaggcttt    660

gatagcgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcattcgc atttttattt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcaccgtgg cggcggtgta taaaggcaaa   1020

ctgctgattg gcaccgtgtt tcataaagcg ctgtattgcg aactgcatca tcatcatcat   1080

catcatcat                                                            1089
```

<210> SEQ ID NO 81
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 81

```
atggcgaaac tgaccgcgct gaccctgctg ggcctgggcc tggcgctgtt tgatggccag     60

aaaagcagct ttcagacccg ctttaacgtg catcgcgaag tgaccccggt ggaactgccg    120

gattgcaacc tggtgaaagg cgtggataac ggcagcgaag atctggaaat tctgccgaac    180

ggcctggcgt ttattagcag cggcctgaaa tatccgggca ttatgagctt tgatccggat    240

aaaagcggca aaattctgct gatggatctg aacgaagaag atccggtggt gctggaactg    300

ggcattaccg gcaacaccct ggatattccg agctttaacc cgcatggcat tagcaccttt    360

accgatgaag ataacaccgt gtatctgctg gtggtgaacc atccggatag cagcagcacc    420
```

-continued gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gattttgcga acggcattaa cattagcccg gatggcaaat atgtgtatat tgcggaaagc 720
ctggcgcgca aaattcatgt gtatgaaaaa catgcgaact ggaccctgac cccgctgaaa 780
agcctggatc tggataccct ggtggataac attagcgtgg atccggtgac cggcgatctg 840
tgggtgggct gccatccgaa cggcatgcgc atttttatt atgatccgaa aaacccgccg 900
ggcagcgaag tgctgcgcat tcaggatatt ctgagcgaag aaccgaaagt gaccgtggtg 960
tatgcggaag atggcaccgt gctgcagggc agcgcggtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 82
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 82
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcggcaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc gcccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaagtgca tctgggcctg 600
gcgtggagct ttgtgaccta ttatagcccg aacgatgtgc gcgtggtggc ggaaggcttt 660
gatagcgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttatt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcagcgtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 83
<211> LENGTH: 1089
<212> TYPE: DNA
<213> ORGANISM: Artificial sequence
<220> FEATURE:

<223> OTHER INFORMATION: Serum paraoxonase (PON1) Variant coding sequence

<400> SEQUENCE: 83

```
atggcgaaac tgaccgcgct gaccctgctg ggcctgggcc tggcgctgag cgatggccag      60
aaaagcagct ttcagacccg ctttaacgtg catcgcgaag tgaccccggt ggaactgccg     120
aactgcaacc tggtgaaagg cgtggataac ggcagcgaag atctggaaat tctgccgaac     180
ggcctggcgt ttattagcag cggcctgaaa tatccgggca ttatgagctt tgatccggat     240
aaaagcggca aaattctgct gatggatctg aacgaagaag atccggtggt gctggaactg     300
ggcattaccg gcaacaccct ggatattagc agctttaacc cgtggggcat tagcaccttt     360
accgatgaag ataacaccgt gtatctgctg gtggtgaacc atccggatag cagcagcacc     420
gtggaagtgt ttaaatttca ggaagaagaa aaaagcctgc tgcatctgaa aaccattcgc     480
cataaactgc tgccgagcgt gaacgatatt gtggcggtgg gcccggaaca tttttatgcg     540
accaacgatc attattttgc ggatccgtat ctgaaaagct gggaaatgca tctgggcctg     600
gcgtggagct ttgtgaccta ttatagcccg aacgatgtgc gcgtggtggc ggaaggcttt     660
gattttgcga acggcattaa cattagcccg gatggcaaat atgtgtatat tgcggaactg     720
ctggcgcata aaattcatgt gtatgaaaaa catgcgaact ggaccctgac cccgctgaaa     780
agcctggatt ttgataccct ggtggataac attagcgtgg atccggtgac cggcgatctg     840
tgggtgggct gccatccgaa cggcatgcgc atttttatt atgatccgaa aaacccgccg     900
ggcagcgaag tgctgcgcat tcaggatatt ctgagcgaag aaccgaaagt gaccgtggtg     960
tatgcggaaa acggcaccgt gctgcagggc agcaccgtgg cggcggtgta taaaggcaaa    1020
ctgctgattg gcaccgcgtt tcataaagcg ctgtattgcg aactgcatca tcatcatcat    1080
catcatcat                                                            1089
```

<210> SEQ ID NO 84
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 84

```
atggcgaaac tgaccgcgct gaccctgctg ggcctgggcc tggcgctgtt tgatggccag      60
aaaagcagct ttcagacccg ctttaacgtg catcgcgaag tgaccccggt ggaactgccg     120
aactgcaacc tggtgaaagg cgtggataac ggcagcgaag atctggaaat tctgccgaac     180
ggcctggcgt ttattagcag cggcggcaaa tatccgggca ttatgagctt tgatccggat     240
aaaagcggca aaattctgct gatggatctg aacgaagaag atccggtggt gctggaactg     300
ggcattaccg gcaacaccct ggatattagc agctttaacc cgtggggcat tagcaccttt     360
accgatgaag ataacaccgt gtatctgctg gtggtgaacc atccggatag cagcagcacc     420
gtggaagtgt ttaaatttca ggaagaagaa aaaagcctgc tgcatctgaa aaccattcgc     480
cataaactgc tgccgagcgt gaacgatatt gtggcggtgg gcccggaaca tttttatgcg     540
accaacgatc attattttgc ggatccgtat ctgaaaagct gggaaatgca tctgggcctg     600
gcgtggagct ttgtgaccta ttatagcccg aacgatgtgc gcgtggtggc ggaaggcttt     660
gatctggcga acggcattaa cattagcccg gatggcaaat atgtgtatat tgcggaactg     720
ctggcgcata aaattcatgt gtatgaaaaa catgcgaact ggaccctgac cccgctgaaa     780
```

agcctggatt ttgataccct ggtggataac attagcgtgg atccggtgac cggcgatctg 840
tgggtgggct gccatccgaa cggcatgcgc attttttatt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 85
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 85
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcagcaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc atgcggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gatagcgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc attttttatt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 86
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 86
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc atccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gattttgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttttatt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgcgtt tcataaagcg ctgtattgcg aactgcatca tcatcatcat 1080
catcatcat 1089

<210> SEQ ID NO 87
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 87
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc atccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gattttgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttttatt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgtgat tcataaagcg ctgtattgcg aactgcatca tcatcatcat 1080
catcatcat 1089

<210> SEQ ID NO 88
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 88
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc atccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gatctggcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttattt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgcgtt tcataaagcg ctgtattgcg aactgcatca tcatcatcat 1080
catcatcat 1089

<210> SEQ ID NO 89
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 89
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc atccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gattttgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcattcgc attttttatt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgcgtt tcataaagcg ctgtattgcg aactgcatca tcatcatcat 1080
catcatcat 1089

<210> SEQ ID NO 90
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 90
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc atccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gatctggcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc attttttatt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgcgtt tcataaagcg ctgtattgcg aactgcatca tcatcatcat 1080
catcatcat 1089

<210> SEQ ID NO 91
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 91
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc atccggatag cagcccgacc 420
gtggaagtgt ttaaatttca ggaagaagaa aaaagcctgc tgcatctgaa aaccattcgc 480
cataaactgc tgccgagcat gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gattttgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttttatt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgcgtt tcataaagcg ctgtattgcg aactgcatca tcatcatcat 1080
catcatcat 1089

<210> SEQ ID NO 92
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 92
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc atccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gattttgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttttatt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgcgtt tcataaagcg ctgtattgcg aactgcatca tcatcatcat 1080
catcatcat 1089

<210> SEQ ID NO 93
<211> LENGTH: 1089
<212> TYPE: DNA
<213> ORGANISM: Artificial sequence
<220> FEATURE:
<223> OTHER INFORMATION: Serum paraoxonase (PON1) Variant coding
sequence

<400> SEQUENCE: 93
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcggcaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc atccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gatagcgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttttatt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 94
<211> LENGTH: 1089
<212> TYPE: DNA
<213> ORGANISM: Artificial sequence
<220> FEATURE:
<223> OTHER INFORMATION: Serum paraoxonase (PON1) Variant coding
sequence

<400> SEQUENCE: 94
atggcgaaac tgaccgcgct gaccctgagc ggcctgggcc tggcgctgtt tgatggccag 60
aaaagcagct ttcagacccg ctataacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcggcaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc gcccggatag cagcagcacc 420
gtggaagtgt ttaaatttca ggaagaagaa aaaagcctgc tgcatctgaa aaccattcgc 480

```
cataaactgc tgccgagcgt gaacgatatt gtggcggtgg gcccggaaca tttttatgcg    540

accaacgatc attattttgc ggatccgtat ctgaaaagct gggaaatgca tctgggcctg    600

gcgtggagct ttgtgaccta ttatagcccg aacgatgtgc gcgtggtggc ggaaggcttt    660

gatagcgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc attttttatt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcagcgtgg cggcggtgta taaaggcaaa   1020

ctgctgattg gcaccgtgtt tcataaagcg ctgtattgcg aactgcatca tcatcatcat   1080

catcatcat                                                           1089
```

<210> SEQ ID NO 95
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 95

```
atggcgaaac tgaccgcgct gaccctgctg ggcctgggcc tggcgctgtt tgatggccag     60

aaaagcagct ttcagacccg ctttaacgtg catcgcgaag tgaccccggt ggaactgccg    120

aactgcaacc tggtgaaagg cgtggataac ggcagcgaag atctggaaat tctgccgaac    180

ggcctggcgt ttattagcag cggcctgaaa tatccgggca ttatgagctt tgatccggat    240

aaaagcggca aaattctgct gatggatctg aacgaagaag atccggtggt gctggaactg    300

ggcattaccg gcaacaccct ggatattagc agctttaacc cgtggggcat tagcaccttt    360

accgatgaag ataacaccgt gtatctgctg gtggtgaacc atccggatag cagcagcacc    420

gtggaagtgt ttaaatttca ggaagaagaa aaaagcctgc tgcatctgaa aaccattcgc    480

cataaactgc tgccgagcgt gaacgatatt gtggcggtgg gcccggaaca tttttatgcg    540

accaacgatc attattttgc ggatccgtat ctgaaaagct gggaaatgca tctgggcctg    600

gcgtggagct ttgtgaccta ttatagcccg aacgatgtgc gcgtggtggc ggaaggcttt    660

gatgtggcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc attttttatt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcaccgtgg cggcggtgta taaaggcaaa   1020

ctgctgattg gcaccgtgtt tcataaagcg ctgtattgcg aactgcatca tcatcatcat   1080

catcatcat                                                           1089
```

<210> SEQ ID NO 96
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 96

```
atggcgaaac tgaccgcgct gaccctgctg ggcctgggcc tggcgctgtt tgatggccag     60
aaaagcagct ttcagacccg ctttaacgtg catcgcgaag tgaccccggt ggaactgccg    120
aactgcaacc tggtgaaagg cgtggataac ggcagcgaag atctggaaat tctgccgaac    180
ggcctggcgt ttattagcag cggcctgaaa tatccgggca ttatgagctt tgatccggat    240
aaaagcggca aaattctgct gatggatctg aacgaagaag atccggtggc gctggaactg    300
ggcattaccg gcaacaccct ggatattagc agctttaacc cgtggggcat tagcaccttt    360
accgatgaag ataacaccgt gtatctgctg gtggtgaacc atgcggatag cagcagcacc    420
gtggaagtgt ttaaatttca ggaagaagaa aaaagcctgc tgcatctgaa aaccattcgc    480
cataaactgc tgccgagcgt gaacgatatt gtggcggtgg gcccggaaca tttttatgcg    540
accaacgatc attattttgc ggatccgtat ctgaaaagct gggaagtgca tctgggcctg    600
gcgtggagct ttgtgaccta ttatagcccg aacgatgtgc gcgtggtggc ggaaggcttt    660
gatagcgcga acggcattaa cattagcccg gatggcaaat atgtgtatat tgcggaactg    720
ctggcgcata aaattcatgt gtatgaaaaa catgcgaact ggaccctgac cccgctgaaa    780
agcctggatt ttgataccct ggtggataac attagcgtgg atccggtgac cggcgatctg    840
tgggtgggct gccatccgaa cggcattcgc atttttattt atgatccgaa aaacccgccg    900
ggcagcgaag tgctgcgcat tcaggatatt ctgagcgaag aaccgaaagt gaccgtggtg    960
tatgcggaaa acggcaccgt gctgcagggc agcaccgtgg cggcggtgta taaaggcaaa   1020
ctgctgattg gcaccgtgtt tcataaagcg ctgtattgcg aactgcatca tcatcatcat   1080
catcatcat                                                          1089
```

<210> SEQ ID NO 97
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 97

```
atggcgaaac tgaccgcgct gaccctgagc ggcctgggcc tggcgctgtt tgatggccag     60
aaaagcagct ttcagacccg ctttaacgtg catcgcgaag tgaccccggt ggaactgccg    120
aactgcaacc tggtgaaagg cgtggataac ggcagcgaag atctggaaat tctgccgaac    180
ggcctggcgt ttattagcag cggcagcaaa tatccgggca ttatgagctt tgatccggat    240
aaaagcggca aaattctgct gatggatctg aacgaagaag atccggtggt gctggaactg    300
ggcattaccg gcaacaccct ggatattagc agctttaacc cgtggggcat tagcaccttt    360
accgatgaag ataacaccgt gtatctgctg gtggtgaacc atgcggatag cagcagcacc    420
gtggaagtgt ttaaatttca ggaagaagaa aaaagcctgc tgcatctgaa aaccattcgc    480
cataaactgc tgccgagcgt gaacgatatt gtggcggtgg gcccggaaca tttttatgcg    540
accaacgatc attattttgc ggatccgtat ctgaaaagct gggaaatgca tctgggcctg    600
gcgtggagct ttgtgaccta ttatagcccg aacgatgtgc gcgtggtggc ggaaggcttt    660
gatagcgcga acggcattaa cattagcccg gatggcaaat atgtgtatat tgcggaactg    720
ctggcgcata aaattcatgt gtatgaaaaa catgcgaact ggaccctgac cccgctgaaa    780
agcctggatt ttgataccct ggtggataac attagcgtgg atccggtgac cggcgatctg    840
tgggtgggct gccatccgaa cggcatgcgc atttttattt atgatccgaa aaacccgccg    900
```

ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 98
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 98
atggcgaaac tgaccgcgct gaccctgagc ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc atgcggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gatagcgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttattt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 99
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 99
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360

```
accgatgaag ataacaccgt gtatctgctg gtggtgaacc atccggatag cagcagcacc    420

gtggaagtgt ttaaatttca ggaagaagaa aaaagcctgc tgcatctgaa aaccattcgc    480

cataaactgc tgccgagcgt gaacgatatt gtggcggtgg gcccggaaca tttttatgcg    540

accaacgatc attattttgc ggatccgtat ctgaaaagct gggaaatgca tctgggcctg    600

gcgtggagct ttgtgaccta ttatagcccg aacgatgtgc gcgtggtggc ggaaggcttt    660

gatagcgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc atttttatt atgatccgaa aaacccgccg    900

ggcagcgaag tgctgcgcat tcagaacatt ctgagcgaag aaccgaaagt gaccgtggtg    960

tatgcggaaa acggcaccgt gctgcagggc agcaccgtgg cggcggtgta taaaggcaaa   1020

ctgctgattg gcaccgcgtt tcataaagcg ctgtattgcg aactgcatca tcatcatcat   1080

catcatcat                                                           1089
```

<210> SEQ ID NO 100
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 100

```
atggcgaaac tgaccgcgct gaccctgagc ggcctgggcc tggcgctgtt tgatggccag     60

aaaagcagct ttcagacccg ctttaacgtg catcgcgaag tgaccccggt ggaactgccg    120

aactgcaacc tggtgaaagg cgtggataac ggcagcgaag atctggaaat tctgccgaac    180

ggcctggcgt ttattagcag cggcctgaaa tatccgggca ttatgagctt tgatccggat    240

aaaagcggca aaattctgct gatggatctg aacgaagaag atccggtggt gctggaactg    300

ggcattaccg gcaacaccct ggatattagc agctttaacc cgtggggcat tagcaccttt    360

accgatgaag ataacaccgt gtatctgctg gtggtgaacc atccggatag cagcagcacc    420

gtggaagtgt ttaaatttca ggaagaagaa aaaagcctgc tgcatctgaa aaccattcgc    480

cataaactgc tgccgagcgt gaacgatatt gtggcggtgg gcccggaaca tttttatgcg    540

accaacgatc attattttgc ggatccgtat ctgaaaagct gggaaatgca tctgggcctg    600

gcgtggagct ttgtgaccta ttatagcccg aacgatgtgc gcgtggtggc ggaaggcttt    660

gatagcgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcattcgc atttttatt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcaccgtgg cggcggtgta taaaggcaaa   1020

ctgctgattg gcaccgcgtt tcataaagcg ctgtattgcg aactgcatca tcatcatcat   1080

catcatcat                                                           1089
```

<210> SEQ ID NO 101
<211> LENGTH: 1089
<212> TYPE: DNA

<213> ORGANISM: Artificial sequence
<220> FEATURE:
<223> OTHER INFORMATION: Serum paraoxonase (PON1) Variant coding sequence

<400> SEQUENCE: 101

```
atggcgaaac tgaccgcgct gaccctgctg ggcctgggcc tggcgctgtt tgatggccag      60
aaaagcagct ttcagacccg ctttaacgtg catcgcgaag tgaccccggt ggaactgccg     120
aactgcaacc tggtgaaagg cgtggataac ggcagcgaag atctggaaat tctgccgaac     180
ggcctggcgt ttattagcag cggcagcaaa tatccgggca ttatgagctt tgatccggat     240
aaaagcggca aaattctgct gatggatctg aacgaagaag atccggtggc gctggaactg     300
ggcattaccg gcaacaccct ggatattagc agctttaacc cgtggggcat tagcaccttt     360
accgatgaag ataacaccgt gtatctgctg gtggtgaacc atgcggatag cagcagcacc     420
gtggaagtgt ttaaatttca ggaagaagaa aaaagcctgc tgcatctgaa aaccattcgc     480
cataaactgc tgccgagcgt gaacgatatt gtggcggtgg gcccggaaca tttttatgcg     540
accaacgatc attattttgc ggatccgtat ctgaaaagct gggaaatgca tctgggcctg     600
gcgtggagct ttgtgaccta ttatagcccg aacgatgtgc gcgtggtggc ggaaggcttt     660
gatagcgcga acggcattaa cattagcccg gatggcaaat atgtgtatat tgcggaactg     720
ctggcgcata aaattcatgt gtatgaaaaa catgcgaact ggaccctgac cccgctgaaa     780
agcctggatt ttgataccct ggtggataac attagcgtgg atccggtgac cggcgatctg     840
tgggtgggct gccatccgaa cggcatgcgc atttttttatt atgatccgaa aaacccgccg     900
ggcagcgaag tgctgcgcat tcaggatatt ctgagcgaag aaccgaaagt gaccgtggtg     960
tatgcggaaa acggcaccgt gctgcagggc agcaccgtgg cggcggtgta taaaggcaaa    1020
ctgctgattg gcaccgtgtt tcataaagcg ctgtattgcg aactgcatca tcatcatcat    1080
catcatcat                                                            1089
```

<210> SEQ ID NO 102
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 102

```
atggcgaaac tgaccgcgct gaccctgctg ggcctgggcc tggcgctgtt tgatggccag      60
aaaagcagct ttcagacccg ctttaacgtg catcgcgaag tgaccccggt ggaactgccg     120
aactgcaacc tggtgaaagg cgtggataac ggcagcgaag atctggaaat tctgccgaac     180
ggcctggcgt ttattagcag cggcctgaaa tatccgggca ttatgagctt tgatccggat     240
aaaagcggca aaattctgct gatggatctg aacgaagaag atccggtggc gctggaactg     300
ggcattaccg gcaacaccct ggatattagc agctttaacc cgtggggcat tagcaccttt     360
accgatgaag ataacaccgt gtatctgctg gtggtgaacc atgcggatag cagcagcacc     420
gtggaagtgt ttaaatttca ggaagaagaa aaaagcctgc tgcatctgaa aaccattcgc     480
cataaactgc tgccgagcgt gaacgatatt gtggcggtgg gcccggaaca tttttatgcg     540
accaacgatc attattttgc ggatccgtat ctgaaaagct gggaaatgca tctgggcctg     600
gcgtggagct ttgtgaccta ttatagcccg aacgatgtgc gcgtggtggc ggaaggcttt     660
gatagcgcga acggcattaa cattagcccg gatggcaaat atgtgtatgt ggcggaactg     720
```

-continued ctggcgcata aaattcatgt gtatgaaaaa catgcgaact ggaccctgac cccgctgaaa 780
agctttgatt ttgataccct ggtggataac attagcgtgg atccggtgac cggcgatctg 840
tgggtgggct gccatccgaa cggcatgcgc atttttttatt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 103
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 103
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggc gctggaactg 300
ggcattaccg gcaacaccct ggatattagc agctttaacc cgtggggcat tagcaccttt 360
accgatgaag ataacaccgt gtatctgctg gtggtgaacc atgcggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gatagcgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttttatt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 104
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 104
atggcgaaac tgaccgcgct gaccctgagc ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcggcaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaaca aaccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gatagcgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttattt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 105
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 105
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc atccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gattttgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttattt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgtgtt tcataaagcg ctgtattgcg aactgcatca tcatcatcat 1080
catcatcat 1089

<210> SEQ ID NO 106
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 106
atggcgaaac tgaccgcgct gaccctgctg ggcctgggcc tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcctgaaa tatccgggca ttatgagctt tgatccggat 240
aaaagcggca aaattctgct gatggatctg aacgaagaag atccggtggt gctggaactg 300
ggcattaccg gcaacaccct ggatattagc agctttaacc cgtggggcat tagcaccttt 360
accgatgaag ataacaccgt gtatctgctg gtggtgaacc atccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600
gcgtggagct ttgtgaccta ttatagcccg aacgatgtgc gcgtggtggc ggaaggcttt 660
gattttgcga acggcattaa cattagcccg gatggcaaat atgtgtatat tgcggaactg 720
ctggcgcata aaattcatgt gtatgaaaaa catgcgaact ggaccctgac cccgctgaaa 780
agcctggatt ttgataccct ggtggataac attagcgtgg atccggtgac cggcgatctg 840
tgggtgggct gccatccgaa cggcatgcgc atttttattt atgatccgaa aaacccgccg 900
ggcagcgaag tgctgcgcat tcaggatatt ctgagcgaag aaccgaaagt gaccgtggtg 960
tatgcggaaa acggcaccgt gctgcagggc agcaccgtgg cggcggtgta taaaggcaaa 1020
ctgctgattg gcaccgcgtt tcataaagcg ctgtattgcg aactgcatca tcatcatcat 1080
catcatcat 1089

<210> SEQ ID NO 107
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 107
atggcgaaac tgaccgcgct gaccctgctg ggcctgggca tggcgctgtt tgatggccag 60
aaaagcagct ttcagacccg ctttaacgtg catcgcgaag tgaccccggt ggaactgccg 120
aactgcaacc tggtgaaagg cgtggataac ggcagcgaag atctggaaat tctgccgaac 180
ggcctggcgt ttattagcag cggcggcaaa tatccgggca ttatgagctt tgatccggat 240
aaaagcggca aaattctgct gatggatctg aacgaagaag atccggtggt gctggaactg 300
ggcattaccg gcaacaccct ggatattagc acctttaacc cgtggggcat tagcaccttt 360
accgatgaag ataacaccgt gtatctgctg gtggtgaacc gcccggatag cagcagcacc 420
gtggaagtgt ttaaatttca ggaagaagaa aaaagcctgc tgcatctgaa aaccattcgc 480
cataaactgc tgccgagcgt gaacgatatt gtggcggtgg gcccggaaca tttttatgcg 540
accaacgatc attattttgc ggatccgtat ctgaaaagct gggaaatgca tctgggcctg 600

```
gcgtggagct ttgtgaccta ttatagcccg aacgatgtgc gcgtggtggc ggaaggcttt    660

gatagcgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc atttttttatt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcagcgtgg cggcggtgta taaaggcaaa   1020

ctgctgattg gcaccgtgtt tcataaagcg ctgtattgcg aactgcatca tcatcatcat   1080

catcatcat                                                            1089
```

<210> SEQ ID NO 108
<211> LENGTH: 1089
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 108

```
atggcgaaac tgaccgcgct gaccctgctg ggcctgggcc tggcgctgtt tgatggccag     60

aaaagcagct ttcagacccg ctttaacgtg catcgcgaag tgaccccggt ggaactgccg    120

aactgcaacc tggtgaaagg cgtggataac ggcagcgaag atctggaaat tctgccgaac    180

ggcctggcgt ttattagcag cggcctgaaa tatccgggca ttatgagctt tgatccggat    240

aaaagcggca aaattctgct gatggatctg aacgaagaag atccggtggt gctggaactg    300

ggcattaccg gcaacaccct ggatattagc agctttaacc cgcatggcat tagcaccttt    360

accgatgaag ataacaccgt gtatctgctg gtggtgaacc atccggatag cagcagcacc    420

gtggaagtgt ttaaatttca ggaagaagaa aaaagcctgc tgcatctgaa aaccattcgc    480

cataaactgc tgccgagcgt gaacgatatt gtggcggtgg gcccggaaca tttttatgcg    540

accaacgatc attattttgc ggatccgtat ctgaaaagct gggaaatgca tctgggcctg    600

gcgtggagct ttgtgaccta ttatagcccg aacgatgtgc gcgtggtggc ggaaggcttt    660

gattttgcga acggcattaa cattagcccg gatggcaaat atgtgtatat tgcggaactg    720

ctggcgcata aaattcatgt gtatgaaaaa catgcgaact ggaccctgac cccgctgaaa    780

agcctggatt ttgataccct ggtggataac attagcgtgg atccggtgac cggcgatctg    840

tgggtgggct gccatccgaa cggcatgcgc attttttatt atgatccgaa aaacccgccg    900

ggcagcgaag tgctgcgcat tcaggatatt ctgagcgaag aaccgaaagt gaccgtggtg    960

tatgcggaaa acggcaccgt gctgcagggc agcaccgtgg cggcggtgta taaaggcaaa   1020

ctgctgattg gcaccgcgtt tcataaagcg ctgtattgcg aactgcatca tcatcatcat   1080

catcatcat                                                            1089
```

<210> SEQ ID NO 109
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 109

```
gatggcgccc aacagtcc                                                   18
```

<210> SEQ ID NO 110
<211> LENGTH: 15
<212> TYPE: DNA
<213> ORGANISM: Artificial sequence
<220> FEATURE:
<223> OTHER INFORMATION: Single strand DNA oligonucleotide

<400> SEQUENCE: 110
gcgcgtccca ttcgc 15

<210> SEQ ID NO 111
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 111
tgatctagtg cggccgccag ctcacagtaa agagctttgt gaaacac 47

<210> SEQ ID NO 112
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 112
gtccggcgta gaggatcg 18

<210> SEQ ID NO 113
<211> LENGTH: 43
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (20)..(21)
<223> OTHER INFORMATION: n is a, c, g, or t

<400> SEQUENCE: 113
ggctttcatc agctccggan nsaagtatcc tggaataatg agc 43

<210> SEQ ID NO 114
<211> LENGTH: 32
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (15)..(16)
<223> OTHER INFORMATION: n is a, c, g, or t

<400> SEQUENCE: 114
cttcatttaa ccctnnsggg attagcacat tc 32

<210> SEQ ID NO 115
<211> LENGTH: 33
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (16)..(17)
<223> OTHER INFORMATION: n is a, c, g, or t

<400> SEQUENCE: 115
ctactggtgg taaacnnscc agactcctcg tcc 33

<210> SEQ ID NO 116
<211> LENGTH: 33
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (17)..(18)
<223> OTHER INFORMATION: n is a, c, g, or t

<400> SEQUENCE: 116
gttgattccg ttagcsnnat caaatccttc tgc 33

<210> SEQ ID NO 117
<211> LENGTH: 31
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (15)..(16)
<223> OTHER INFORMATION: n is a, c, g, or t

<400> SEQUENCE: 117
gagctttgtg aaasnntgtg ccaatcagca g 31

<210> SEQ ID NO 118
<211> LENGTH: 33
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (17)..(18)
<223> OTHER INFORMATION: n is a, c, g, or t

<400> SEQUENCE: 118
gtaaagagct ttgtgsnnca ctgtgccaat cag 33

<210> SEQ ID NO 119
<211> LENGTH: 33
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (16)..(17)
<223> OTHER INFORMATION: n is a, c, g, or t

<400> SEQUENCE: 119
cagtaaagag ctttsnnaaa cactgtgcca atc 33

<210> SEQ ID NO 120
<211> LENGTH: 363
<212> TYPE: PRT
<213> ORGANISM: Artificial sequence
<220> FEATURE:
<223> OTHER INFORMATION: Serum paraoxonase (PON1) Variant amino acid
sequence

<400> SEQUENCE: 120

Met Ala Lys Leu Thr Glu Leu Thr Leu Leu Gly Leu Gly Leu Ala Leu

-continued

```
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Gly Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Trp Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Ser Ala Asn
    210                 215                 220

Gly Ile Asn Ile Ser Pro Asp Gly Glu Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Ser Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu His His His His His His His His
        355                 360
```

```
<210> SEQ ID NO 121
<211> LENGTH: 366
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 121

Met Ala Lys Leu Thr Ala Leu Thr Leu Leu Gly Leu Gly Leu Ala Leu
```

-continued

```
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Leu Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Met Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365
```

<210> SEQ ID NO 122
<211> LENGTH: 366
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 122

```
Met Ala Lys Leu Thr Ala Leu Thr Leu Leu Gly Leu Gly Leu Ala Leu
```

-continued

```
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Ala Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Met Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Gly Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365
```

<210> SEQ ID NO 123
<211> LENGTH: 366
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 123

```
Met Ala Lys Leu Thr Ala Leu Thr Leu Leu Gly Leu Gly Leu Ala Leu
```

-continued 1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Leu
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Val Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Met Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365

<210> SEQ ID NO 124
<211> LENGTH: 366
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 124

Met Ala Lys Leu Thr Ala Leu Thr Leu Leu Gly Leu Gly Leu Ala Leu

-continued

```
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Val Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Val Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365


<210> SEQ ID NO 125
<211> LENGTH: 366
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 125

Met Ala Lys Leu Thr Ala Leu Thr Leu Leu Gly Leu Gly Leu Ala Leu
```

-continued

```
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Ala Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Met Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Gly Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365
```

<210> SEQ ID NO 126
<211> LENGTH: 366
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 126

```
Met Ala Lys Leu Thr Ala Leu Thr Leu Leu Gly Leu Gly Leu Ala Leu
```

-continued

```
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Asn Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Leu Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Met Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365


<210> SEQ ID NO 127
<211> LENGTH: 366
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 127

Met Ala Lys Leu Thr Ala Leu Thr Leu Leu Gly Leu Gly Leu Ala Leu
```

```
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Ile Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Ala Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Met Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Phe Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365
```

<210> SEQ ID NO 128
<211> LENGTH: 366
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 128

```
Met Ala Lys Leu Thr Ala Leu Thr Leu Leu Gly Leu Gly Leu Ala Leu
```

```
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Ile Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Leu Gly Ile Ser Thr Phe Thr Asp Glu Asp Asn Thr Val Tyr
        115                 120                 125

Leu Leu Val Val Asn Arg Pro His Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Met Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Leu Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365
```

<210> SEQ ID NO 129
<211> LENGTH: 366
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 129

```
Met Ala Lys Leu Thr Ala Leu Thr Leu Leu Gly Leu Gly Leu Ala Leu
```

-continued

```
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Met Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Ala Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Met Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Leu Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350

Cys Glu Leu Ala Ala Ala Leu Glu His His His His His His
        355                 360                 365
```

<210> SEQ ID NO 130
<211> LENGTH: 1101
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 130

```
atggctaaac tgacagcgct cacactcttg ggctgggat tggcactctt cgatggacag     60
```

```
aagtcttctt tccaaacacg atttaatgtt caccgtgaag taactccagt ggaacttcct    120

aactgtaatt tagttaaagg ggttgacaat ggttctgaag acttggaaat actgcccaat    180

ggactggctt tcatcagctc cggagtgaag tatcctggaa taatgagctt tgaccctgat    240

aagtctggaa agatacttct aatggacctg aatgaggaag acccagtagt gttggaactg    300

ggcattactg gaaatacatt ggatatatct tcatttaacc ctgcggggat tagcacattc    360

acagatgaag ataacactgt gtacctactg gtggtaaaca ggccagactc ctcgtccacc    420

gtggaggtgt ttaaatttca agaagaagaa aaatcacttt tgcatctgaa aaccatcaga    480

cacaagcttc tgcctagtgt gaatgacatt gtcgctgtgg gacctgaaca cttttatgcc    540

acaaatgatc actattttgc tgacccttac ttaaaatcat gggaaatgca tttgggatta    600

gcgtggtcat ttgttactta ttatagtccc aatgatgttc gagtagtggc agaaggattt    660

gatatggcta acggaatcaa catctcacca gacggcaagt atgtctatat agctgagttg    720

ctggctcata agatccatgt gtatgaaaag cacgctaatt ggactttaac tccattgaag    780

tccctcgact ttgacaccct tgtggataac atctctgtgg atcctgtgac aggggacctc    840

tgggtgggat gccatcccaa cggaatgcga atcttctact atgacccaaa gaatcctccc    900

ggctcagagg tgcttcgaat ccaggacatt ttatccgaag agcccaaagt gacagtggtt    960

tatgcagaaa atggcactgt attacagggc agctcggtgg ccgctgtgta caaagggaaa   1020

ctgctgattg gcacagtgtt tcacaaagct ctttactgtg agctggcggc cgcactcgag   1080

caccaccacc accaccactg a                                             1101
```

<210> SEQ ID NO 131
<211> LENGTH: 1101
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 131

```
atggctaaac tgacagcgct cacactcttg gggctgggat tggcactctt cgatggacag     60

aagtcttctt tccaaacacg atttaatgtt caccgtgaag taactccagt ggaacttcct    120

aactgtaatt tagttaaagg ggttgacaat ggttctgaag acttggaaat actgcccaat    180

ggactggctt tcatcagctc cggagtgaag tatcctggaa taatgagctt tgaccctgat    240

aagtctggaa agatacttct aatggacctg aatgaggaag acccagtagt gttggaactg    300

ggcattactg gaaatacatt ggatatatct tcatttaacc ctctggggat tagcacattc    360

acagatgaag ataacactgt gtacctactg gtggtaaaca ggccagactc ctcgtccacc    420

gtggaggtgt ttaaatttca agaagaagaa aaatcacttt tgcatctgaa aaccatcaga    480

cacaagcttc tgcctagtgt gaatgacatt gtcgctgtgg gacctgaaca cttttatgcc    540

acaaatgatc actattttgc tgacccttac ttaaaatcat gggaaatgca tttgggatta    600

gcgtggtcat ttgttactta ttatagtccc aatgatgttc gagtagtggc agaaggattt    660

gatatggcta acggaatcaa catctcacca gacggcaagt atgtctatat agctgagttg    720

ctggctcata agatccatgt gtatgaaaag cacgctaatt ggactttaac tccattgaag    780

tccctcgact ttgacaccct tgtggataac atctctgtgg atcctgtgac aggggacctc    840

tgggtgggat gccatcccaa cggaatgcga atcttctact atgacccaaa gaatcctccc    900

ggctcagagg tgcttcgaat ccaggacatt ttatccgaag agcccaaagt gacagtggtt    960
```

```
tatgcagaaa atggcactgt attacagggc agctcggtgg ccgctgtgta caaagggaaa   1020

ctgctgattg gcacagtgtt tcacaaagct ctttactgtg agctggcggc cgcactcgag   1080

caccaccacc accaccactg a                                             1101
```

<210> SEQ ID NO 132
<211> LENGTH: 1101
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 132

```
atggctaaac tgacagcgct cacactcttg gggctgggat tggcactctt cgatggacag     60

aagtcttctt tccaaacacg atttaatgtt caccgtgaag taactccagt ggaacttcct    120

aactgtaatt tagttaaagg ggttgacaat ggttctgaag acttggaaat actgcccaat    180

ggactggctt tcatcagctc cggagtgaag tatcctggaa taatgagctt tgaccctgat    240

aagtctggaa agatacttct aatggacctg aatgaggaag acccagtagt gttggaactg    300

ggcattactg gaaatacatt ggatatatct tcatttaacc ctgcggggat tagcacattc    360

acagatgaag ataacactgt gtacctactg gtggtaaaca ggccagactc ctcgtccacc    420

gtggaggtgt ttaaatttca agaagaagaa aaatcacttt tgcatctgaa aaccatcaga    480

cacaagcttc tgcctagtgt gaatgacatt gtcgctgtgg gacctgaaca cttttatgcc    540

acaaatgatc actattttgc tgacccttac ttaaaatcat gggaactgca tttgggatta    600

gcgtggtcat ttgttactta ttatagtccc aatgatgttc gagtagtggc agaaggattt    660

gatatggcta acggaatcaa catctcacca gacggcaagt atgtctatat agctgagttg    720

ctggctcata agatccatgt gtatgaaaag cacgctaatt ggactttaac tccattgaag    780

tccctcgact ttgacaccct tgtggataac atctctgtgg atcctgtgac aggggacctc    840

tgggtgggat gccatcccaa cggaatgcga atcttctact atgacccaaa gaatcctccc    900

ggctcagagg tgcttcgaat ccaggacatt ttatccgaag agcccaaagt gacagtggtt    960

tatgcagaaa atggcactgt attacagggc agctcggtgg ccgctgtgta caaagggaaa   1020

ctgctgattg gcacagtgtt tcacaaagct ctttactgtg agctggcggc cgcactcgag   1080

caccaccacc accaccactg a                                             1101
```

<210> SEQ ID NO 133
<211> LENGTH: 1101
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 133

```
atggctaaac tgacagcgct cacactcttg gggctgggat tggcactctt cgatggacag     60

aagtcttctt tccaaacacg atttaatgtt caccgtgaag taactccagt ggaacttcct    120

aactgtaatt tagttaaagg ggttgacaat ggttctgaag acttggaaat actgcccaat    180

ggactggctc tcatcagctc cggagtgaag tatcctggaa taatgagctt tgaccctgat    240

aagtctggaa agatacttct aatggacctg aatgaggaag acccagtagt gttggaactg    300

ggcattactg gaaatacatt ggatatatct tcatttaacc ctgtggggat tagcacattc    360

acagatgaag ataacactgt gtacctactg gtggtaaaca ggccagactc ctcgtccacc    420
```

gtggaggtgt ttaaatttca agaagaagaa aaatcacttt tgcatctgaa aaccatcaga 480
cacaagcttc tgcctagtgt gaatgacatt gtcgctgtgg gacctgaaca cttttatgcc 540
acaaatgatc actattttgc tgacccttac ttaaaatcat gggaaatgca tttgggatta 600
gcgtggtcat ttgttactta ttatagtccc aatgatgttc gagtagtggc agaaggattt 660
gatatggcta acggaatcaa catctcacca gacggcaagt atgtctatat agctgagttg 720
ctggctcata agatccatgt gtatgaaaag cacgctaatt ggactttaac tccattgaag 780
tccctcgact ttgacaccct tgtggataac atctctgtgg atcctgtgac aggggacctc 840
tgggtgggat gccatcccaa cggaatgcga atcttctact atgacccaaa gaatcctccc 900
ggctcagagg tgcttcgaat ccaggacatt ttatccgaag agcccaaagt gacagtggtt 960
tatgcagaaa atggcactgt attacagggc agctcggtgg ccgctgtgta caaagggaaa 1020
ctgctgattg gcacagtgtt tcacaaagct ctttactgtg agctggcggc cgcactcgag 1080
caccaccacc accaccactg a 1101

<210> SEQ ID NO 134
<211> LENGTH: 1101
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 134
atggctaaac tgacagcgct cacactcttg ggctgggat tggcactctt cgatggacag 60
aagtcttctt tccaaacacg atttaatgtt caccgtgaag taactccagt ggaacttcct 120
aactgtaatt tagttaaagg ggttgacaat ggttctgaag acttggaaat actgcccaat 180
ggactggctt tcatcagctc cggagtgaag tatcctggaa taatgagctt tgaccctgat 240
aagtctggaa agatacttct aatggacctg aatgaggaag acccagtagt gttggaactg 300
ggcattactg gaaatacatt ggatatatct tcatttaacc ctgtggggat tagcacattc 360
acagatgaag ataacactgt gtacctactg gtggtaaaca ggccagactc ctcgtccacc 420
gtggaggtgt ttaaatttca agaagaagaa aaatcacttt tgcatctgaa aaccatcaga 480
cacaagcttc tgcctagtgt gaatgacatt gtcgctgtgg gacctgaaca cttttatgcc 540
acaaatgatc actattttgc tgacccttac ttaaaatcat gggaaatgca tttgggatta 600
gcgtggtcat ttgttactta ttatagtccc aatgatgttc gagtagtggc agaaggattt 660
gatgtggcta acggaatcaa catctcacca gacggcaagt atgtctatat agctgagttg 720
ctggctcata agatccatgt gtatgaaaag cacgctaatt ggactttaac tccattgaag 780
tccctcgact ttgacaccct tgtggataac atctctgtgg atcctgtgac aggggacctc 840
tgggtgggat gccatcccaa cggaatgcga atcttctact atgacccaaa gaatcctccc 900
ggctcagagg tgcttcgaat ccaggacatt ttatccgaag agcccaaagt gacagtggtt 960
tatgcagaaa atggcactgt attacagggc agctcggtgg ccgctgtgta caaagggaaa 1020
ctgctgattg gcacagtgtt tcacaaagct ctttactgtg agctggcggc cgcactcgag 1080
caccaccacc accaccactg a 1101

<210> SEQ ID NO 135
<211> LENGTH: 1101
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 135

```
atggctaaac tgacagcgct cacactcttg gggctgggat tggcactctt cgatggacag      60
aagtcttctt tccaaacacg atttaatgtt caccgtgaag taactccagt ggaacttcct     120
aactgtaatt tagttaaagg ggttgacaat ggttctgaag acttggaaat actgcccaat     180
ggactggctt tcatcagctc cggagtgaag tatcctggaa taatgagctt tgaccctgat     240
aagtctggaa agatacttct aatggacctg aatgaggaag acccagtagt gttggaactg     300
ggcattactg gaaatacatt ggatatatct tcatttaacc ctgcggggat tagcacattc     360
acagatgaag ataacactgt gtacctactg gtggtaaaca ggccagactc ctcgtccacc     420
gtggaggtgt ttaaatttca agaagaagaa aaatcacttt tgcatctgaa aaccatcaga     480
cacaagcttc tgcctagtgt gaatgacatt gtcgctgtgg gacctgaaca cttttatgcc     540
acaaatgatc actattttgc tgacccttac ttaaaatcat gggaaatgca tttgggatta     600
gcgtggtcat ttgttactta ttatagtccc aatgatgttc gagtagtggc agaaggattt     660
gatatggcta acggaatcaa catctcacca gacggcaagt atgtctatat agctgagttg     720
ctggctcata agatccatgt gtatgaaaag cacgctaatt ggactttaac tccattgaag     780
tccctcgact ttgacaccct tgtggataac atctctgtgg atcctgtgac aggggacctc     840
tgggtgggat gccatcccaa cggaatgcga atcttctact atgacccaaa gaatcctccc     900
ggctcagagg tgcttcgaat ccagggcatt ttatccgaag agcccaaagt gacagtggtt     960
tatgcagaaa atggcactgt attacagggc agctcggtgg ccgctgtgta caaagggaaa    1020
ctgctgattg gcacagtgtt tcacaaagct ctttactgtg agctggcggc cgcactcgag    1080
caccaccacc accaccactg a                                              1101
```

<210> SEQ ID NO 136
<211> LENGTH: 1101
<212> TYPE: DNA
<213> ORGANISM: Artificial sequence
<220> FEATURE:
<223> OTHER INFORMATION: Serum paraoxonase (PON1) Variant coding
sequence

<400> SEQUENCE: 136

```
atggctaaac tgacagcgct cacactcttg gggctgggat tggcactctt cgatggacag      60
aagtcttctt tccaaacacg atttaatgtt caccgtgaag taactccagt ggaacttcct     120
aactgtaatt tagttaaagg ggttgacaat ggttctgaag acttggaaat actgcccaat     180
ggactggctt tcatcagctc cggactgaac tatcctggaa taatgagctt tgaccctgat     240
aagtctggaa agatacttct aatggacctg aatgaggaag acccagtagt gttggaactg     300
ggcattactg gaaatacatt ggatatatct tcatttaacc ctctggggat tagcacattc     360
acagatgaag ataacactgt gtacctactg gtggtaaaca ggccagactc ctcgtccacc     420
gtggaggtgt ttaaatttca agaagaagaa aaatcacttt tgcatctgaa aaccatcaga     480
cacaagcttc tgcctagtgt gaatgacatt gtcgctgtgg gacctgaaca cttttatgcc     540
acaaatgatc actattttgc tgacccttac ttaaaatcat gggaaatgca tttgggatta     600
gcgtggtcat ttgttactta ttatagtccc aatgatgttc gagtagtggc agaaggattt     660
gatatggcta acggaatcaa catctcacca gacggcaagt atgtctatat agctgagttg     720
ctggctcata agatccatgt gtatgaaaag cacgctaatt ggactttaac tccattgaag     780
tccctcgact ttgacaccct tgtggataac atctctgtgg atcctgtgac aggggacctc     840
```

tgggtgggat gccatcccaa cggaatgcga atcttctact atgacccaaa gaatcctccc 900
ggctcagagg tgcttcgaat ccaggacatt ttatccgaag agcccaaagt gacagtggtt 960
tatgcagaaa atggcactgt attacagggc agctcggtgg ccgctgtgta caaagggaaa 1020
ctgctgattg gcacagtgtt tcacaaagct ctttactgtg agctggcggc cgcactcgag 1080
caccaccacc accaccactg a 1101

<210> SEQ ID NO 137
<211> LENGTH: 1101
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 137
atggctaaac tgacagcgct cacactcttg ggctgggat tggcactctt cgatggacag 60
aagtcttctt tccaaacacg atttaatgtt caccgtgaag taactccagt ggaacttcct 120
aactgtaatt tagttaaagg ggttgacaat ggttctgaag acattgaaat actgcccaat 180
ggactggctt tcatcagctc cggagtgaag tatcctggaa taatgagctt tgaccctgat 240
aagtctggaa agatacttct aatggacctg aatgaggaag acccagtagt gttggaactt 300
ggcattactg gaaatacatt ggatatatct tcatttaacc ctgcggggat tagcacattc 360
acagatgaag ataacactgt gtacctactg gtggtaaaca ggccagactc ctcgtccacc 420
gtggaggtgt ttaaatttca agaagaagaa aaatcacttt tgcatctgaa aaccatcaga 480
cacaagcttc tgcctagtgt gaatgacatt gtcgctgtgg gacctgaaca cttttatgcc 540
acaaatgatc actattttgc tgacccttac ttaaaatcat gggaaatgca tttgggatta 600
gcgtggtcat ttgttactta ttatagtccc aatgatgttc gagtagtggc agaaggattt 660
gatatggcta acggaatcaa catctcacca gacggcaagt atgtctatat agctgagttg 720
ctggctcata agatccatgt gtatgaaaag cacgctaatt ggactttaac tccattgaag 780
tccctcgact ttgacaccct tgtggataac atctctgtgg atcctgtgac aggggacctc 840
tgggtgggat gccatcccaa cggaatgcga tttttctact atgacccaaa gaatcctccc 900
ggctcagagg tgcttcgaat ccaggacatt ttatccgaag agcccaaagt gacagtggtt 960
tatgcagaaa atggcactgt attacagggc agctcggtgg ccgctgtgta caaagggaaa 1020
ctgctgattg gcacagtgtt tcacaaagct ctttactgtg agctggcggc cgcactcgag 1080
caccaccacc accaccactg a 1101

<210> SEQ ID NO 138
<211> LENGTH: 1101
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 138
atggctaaac tgacagcgct cacactcttg ggctgggat tggcactctt cgatggacag 60
aagtcttctt tccaaacacg atttaatgtt caccgtgaag taactccagt ggaacttcct 120
aactgtaatt tagttaaagg ggttgacaat ggttctgaag acattgaaat actgcccaat 180
ggactggctt tcatcagctc cggagtgaag tatcctggaa taatgagctt tgaccctgat 240
aagtctggaa agatacttct aatggacctg aatgaggaag acccagtagt gttggaactg 300

```
ggcattactg gaaatacatt ggatatatct tcatttaacc ctctggggat tagcacattc    360

acagatgaag ataacactgt gtacctactg gtggtaaaca ggccacattc ctcgtccacc    420

gtggaggtgt ttaaatttca agaagaagaa aaatcacttt tgcatctgaa aaccatcaga    480

cacaagcttc tgcctagtgt gaatgacatt gtcgctgtgg gacctgaaca cttttatgcc    540

acaaatgatc actattttgc tgacccttac ttaaaatcat gggaaatgca tttgggatta    600

gcgtggtcat ttgttactta ttatagtccc aatgatgttc gagtagtggc agaaggattt    660

gatatggcta acggaatcaa catctcacca gacggcaagt atgtctatat agctgagttg    720

ctggctcata agatccatgt gtatgaaaag cacgctaatt ggactttaac tccattgaag    780

tccctcgact ttgacaccct tgtggataac atctctgtgg atcctgtgac aggggacctc    840

tgggtgggat gccatcccaa cggaatgcga ctgttctact atgacccaaa gaatcctccc    900

ggctcagagg tgcttcgaat ccaggacatt ttatccgaag agcccaaagt gacagtggtt    960

tatgcagaaa atggcactgt attacagggc agctcggtgg ccgctgtgta caaagggaaa   1020

ctgctgattg gcacagtgtt tcacaaagct ctttactgtg agctggcggc cgcactcgag   1080

caccaccacc accaccactg a                                             1101
```

<210> SEQ ID NO 139
<211> LENGTH: 1101
<212> TYPE: DNA
<213> ORGANISM: Artificial sequence
<220> FEATURE:
<223> OTHER INFORMATION: Serum paraoxonase (PON1) Variant coding sequence

<400> SEQUENCE: 139

```
atggctaaac tgacagcgct cacactcttg ggcctgggat tggcactctt cgatggacag     60

aagtcttctt tccaaacacg atttaatgtt caccgtgaag taactccagt ggaacttcct    120

aactgtaatt tagttaaagg ggttgacaat ggttctgaag acatggaaat actgcccaat    180

ggactggctt tcatcagctc cggagtgaag tatcctggaa taatgagctt tgaccctgat    240

aagtctggaa agatacttct aatggacctg aatgaggaag acccagtagt gttggaactg    300

ggcattactg gaaatacatt ggatatatct tcatttaacc ctgcggggat tagcacattc    360

acagatgaag ataacactgt gtacctactg gtggtaaaca ggccagactc ctcgtccacc    420

gtggaggtgt ttaaatttca agaagaagaa aaatcacttt tgcatctgaa aaccatcaga    480

cacaagcttc tgcctagtgt gaatgacatt gtcgctgtgg gacctgaaca cttttatgcc    540

acaaatgatc actattttgc tgacccttac ttaaaatcat gggaaatgca tttgggatta    600

gcgtggtcat ttgttactta ttatagtccc aatgatgttc gagtagtggc agaaggattt    660

gatatggcta acggaatcaa catctcacca gacggcaagt atgtctatat agctgagttg    720

ctggctcata agatccatgt gtatgaaaag cacgctaatt ggactttaac tccattgaag    780

tccctcgact ttgacaccct tgtggataac atctctgtgg atcctgtgac aggggacctc    840

tgggtgggat gccatcccaa cggaatgcga ctgttctact atgacccaaa gaatcctccc    900

ggctcagagg tgcttcgaat ccaggacatt ttatccgaag agcccaaagt gacagtggtt    960

tatgcagaaa atggcactgt attacagggc agctcggtgg ccgctgtgta caaagggaaa   1020

ctgctgattg gcacagtgtt tcacaaagct ctttactgtg agctggcggc cgcactcgag   1080

caccaccacc accaccactg a                                             1101
```

<210> SEQ ID NO 140
<211> LENGTH: 363
<212> TYPE: PRT
<213> ORGANISM: Artificial sequence
<220> FEATURE:
<223> OTHER INFORMATION: Serum paraoxonase (PON1) Variant amino acid sequence

<400> SEQUENCE: 140

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Ala Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Met Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Leu Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350
```

```
Cys Glu Leu His His His His His His His His
        355                 360


<210> SEQ ID NO 141
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 141

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Ile Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Ala Gly Ile Ser Thr Phe Thr Asp Glu Asp Asn Thr Val Tyr
        115                 120                 125

Leu Leu Val Val Asn Arg Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met Arg Leu Gly Leu Ala Trp Ser Phe Val Thr Tyr Tyr
        195                 200                 205

Ser Pro Asn Asp Val Arg Val Val Ala Glu Gly Phe Asp Met Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Leu Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
            340                 345                 350
```

```
Cys Glu Leu His His His His His His His His
        355                 360


<210> SEQ ID NO 142
<211> LENGTH: 363
<212> TYPE: PRT
<213> ORGANISM: Artificial sequence
<220> FEATURE:
<223> OTHER INFORMATION: Serum paraoxonase (PON1) Variant amino acid
      sequence

<400> SEQUENCE: 142

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Ile Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro Ala Gly Ile Ser Thr Phe Thr Asp Glu Asp Asn Thr Val Tyr
        115                 120                 125

Leu Leu Val Val Asn Arg Pro Gln Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Met Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Leu Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335
```

-continued

```
Tyr Lys Gly Lys Leu Leu Ile Gly Thr Val Phe His Lys Ala Leu Tyr
            340                 345                 350

Cys Glu Leu His His His His His His His His
        355                 360
```